US010590082B2

(12) United States Patent
Overkleeft et al.

(10) Patent No.: US 10,590,082 B2
(45) Date of Patent: *Mar. 17, 2020

(54) N-(5-((ARYL OR HETEROARYL)METHYLOXY)PENTYL)-SUBSTITUTED IMINOSUGARS AS INHIBITORS OF GLUCOSYLCERAMIDE SYNTHASE

(71) Applicants: Academisch Medisch Centrum, Amsterdam (NL); Universiteit Leiden, Leiden (NL)

(72) Inventors: Herman Steven Overkleeft, Leiden (NL); Stan Van Boeckel, Leiden (NL); Johannes Maria Franciscus Gerardus Aerts, Amsterdam (NL); Amar Ghisaidoobe, Leiden (NL); Richard Van Den Berg, Leiden (NL)

(73) Assignees: Academisch Medisch Centrum, Amsterdam Zuidoost (NL); Universiteit Leiden, Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/241,705

(22) Filed: Jan. 7, 2019

(65) Prior Publication Data

US 2019/0144388 A1 May 16, 2019

Related U.S. Application Data

(63) Continuation of application No. 15/129,815, filed as application No. PCT/NL2015/050188 on Mar. 23, 2015, now Pat. No. 10,189,784.

(30) Foreign Application Priority Data

Mar. 27, 2014 (EP) ..................................... 14162104

(51) Int. Cl.
| | |
|---|---|
| A61K 31/445 | (2006.01) |
| A61K 31/4545 | (2006.01) |
| A61P 3/00 | (2006.01) |
| A61P 25/16 | (2006.01) |
| A61P 9/10 | (2006.01) |
| C07D 211/40 | (2006.01) |
| C07D 211/46 | (2006.01) |

(52) U.S. Cl.
CPC .............. *C07D 211/40* (2013.01); *A61P 3/00* (2018.01); *C07D 211/46* (2013.01)

(58) Field of Classification Search
CPC ..... A61K 31/445; A61K 31/4545; A61P 3/00; A61P 25/16; A61P 9/10
See application file for complete search history.

(56) References Cited

U.S. PATENT DOCUMENTS 6,177,447 B1  1/2001  Aerts et al.

FOREIGN PATENT DOCUMENTS

WO  1998002161  1/1998

OTHER PUBLICATIONS

Extended European Search Report dated Dec. 20, 2018, Appl. No. EP18191316.1, 7 pp.
Ghisaidoobe et al. (2014) "Identification and Development of Biphenyl Substituted Iminosugars as Imroved Dual Glucosylceramide Sythase/Neutral Glucosylceramidase Inhibitors" J. of Med. Chem. 57(21):9096-9104.
Schitter et al. (2010) "Flourous Iminoalditols: A New Family of Glycosidase Inhibitors and Pharmacological Chaperones" ChemBioChem., 11(14):2026-2033.
Wennekes et al. (2010) "Dual-Action Lipophilic Iminosugar Improves Glycemic Control in Obese Rodents by Reduction of Visceral Glycosphingolipids and Buffering of Carbohydrate Assimilation" J. of Med. Chem., 53 (2):689-698.
Yu et al. (2012) "Design, Synthesis, and Biological Evaluation of N-Alkylated Deoxynojirimycin (DNJ) Derivatives for the Treatment of Dengue Virus Infection" J. of Med. Chem. 55(13):6061-6075.
Zhou et al. (2008) "Hybrid angiogenesis inhibitors: Synthesis and biological evaluation of bifunctional compounds based on 1-deoxynojirimycin and aryl-1,2,3-triazoles" Bioorganic & Medicinal Chem. Letters, 18(3):954-958.
Ashe et al. (2011) "Iminosugar-Based Inhibitors of Glucosylceramide Synthase Increase Brain Glycosphingolipids and Survival in a Mouse Model of Sandhoff Disease" PLoS ONE, 6(6):e21758, 11pgs.
Guérard et al. (2017) "Lucerastat, an Iminosugar for Substrate Reduction Therapy: Tolerability, Pharmacodynamics, and Pharmacokinetics in Patients with Fabry Disease on Enzyme Replacement" ASCPT, 28pgs.

(Continued)

*Primary Examiner* — Bruck Kifle
(74) *Attorney, Agent, or Firm* — Brian E. Davy; Bozicevic, Field & Francis LLP

(57) ABSTRACT

Deoxynojirimycin and deoxygalactonojirimycin derivatives according to the present invention are N-alkylated D-galacto, D-gluco- or L-ido-deoxynojirimycin with a linear methyloxypentyl group bearing various sidegroups and a non-fused bicyclic aromatic group ("X") on the methyloxycarbon. Formula (I), Formula (Ia). These compounds display an increased inhibitory potency towards GCS, and/or an increased inhibitory potency towards GBA2, and/or a decreased inhibitory potency towards GBA1, relative to known deoxynojirimycin derivatives of the same (D-gluco, L-ido or D-galacto) configuration. Therefore, compounds of the present invention are effective in the treatment of diseases which are associated with an irregular level of cytosolic or lysosomal glucosylceramide and/or higher glycosphingolipids, such as a lysosomal storage disorder, such as Gaucher disease, Fabry disease, Tay-Sachs disease, Sandhoff disease, GM1 gangliosidosis, Sialidosis, Niemann Pick disease type C and AMRF, or a symptom of one of the diseases collectively classed as metabolic syndrome, such as obesity, insulin resistance, hyperlipidemia, hypercholesterolemia, polycystic kidney disease, type II diabetes and chronic inflammation, or a neurodenegerative disorder, such as Parkinson disease or Lewy-body dementia.

25 Claims, 2 Drawing Sheets

(56) References Cited

OTHER PUBLICATIONS

Kodama et al. (2011) "Lyso-GM2 Ganglioside: A Possible Biomarker of Tay-Sachs Disease and Sandhoff Disease" PLoS ONE, 6(12):e29074, 6pgs.
Lyseng-Williamson (2014) "Miglustat: A Review of Its Use in Niemann-Pick Disease Type C" Drugs, 74:61-74.
Marques et al. (2015) "Reducing GBA2 Activity Ameliorates Neuropathology in Niemann-Pick Type C Mice" PLoS ONE, 10(8):e0135889, 18pgs.

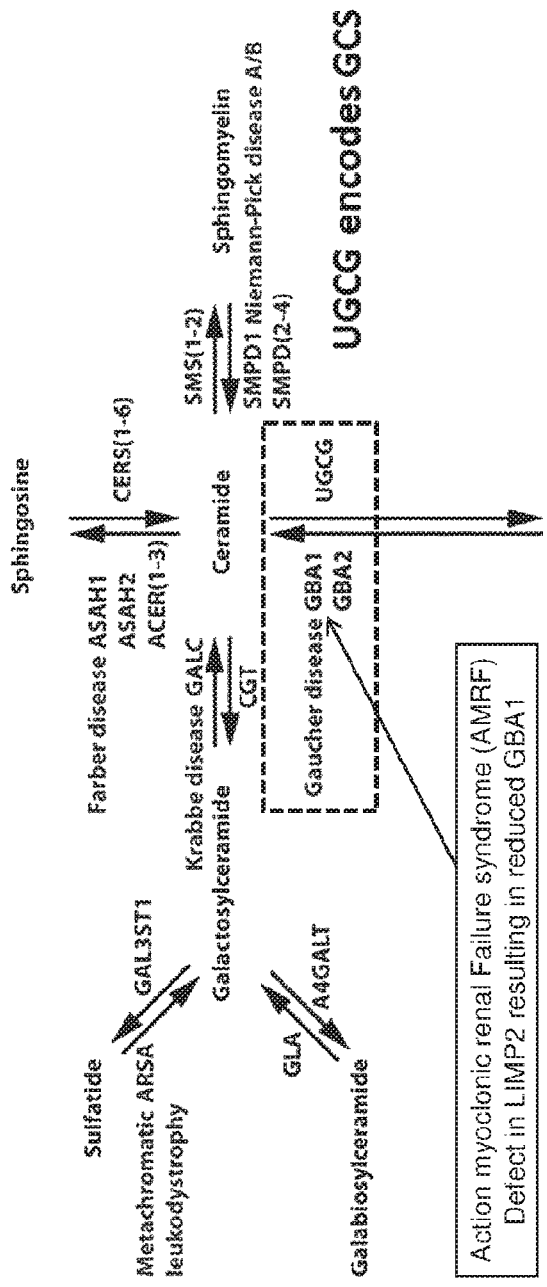

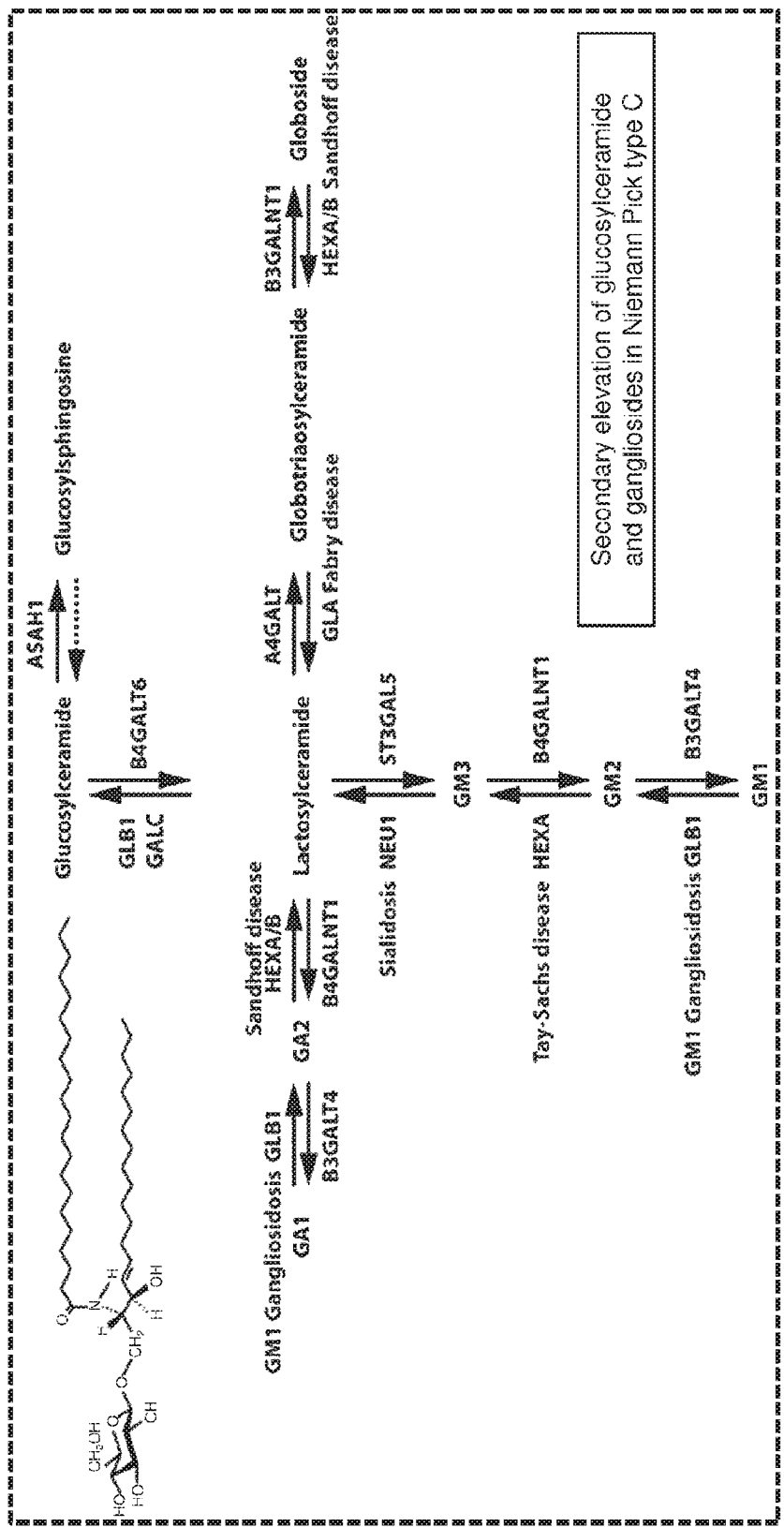

N-(5-((ARYL OR HETEROARYL)METHYLOXY)PENTYL)-SUBSTITUTED IMINOSUGARS AS INHIBITORS OF GLUCOSYLCERAMIDE SYNTHASE

INTRODUCTION

Glucosylceramide is the condensation product of UDP-glucose and ceramide and its formation is catalysed by glucosylceramide synthase (GCS, EC 2.4.1.80).

The enzymes involved in ceramide biosynthesis are localized on the cytosolic leaflet of the endoplasmic reticulum. The biosynthesis starts with the condensation of the amino acid serine with a palmitoyl coenzyme A by serine palmitoyl transferase to yield 3-ketosphinganine. Next, this is reduced to D-erythro-sphinganine by 3-ketosphinganine reductase and subsequently acylated to dihydroceramide by a N-acyl-transferase. Dihydroceramide is largely desaturated to ceramide by the action of dihydroceramide desaturase.

Glucosylceramide is formed by glucosylceramide synthase (GCS) that is located on the cytosolic leaflet of the Golgi apparatus. The enzyme uses UDP-glucose as co-substrate and catalyzes the β-glycosidic linkage of glucose to the 1-position of ceramide. Glucosylceramide subsequently translocates through the Golgi membrane to reach the inner leaflet. From here, it can reach the plasma membrane or can be modified by further glycosylation in the Golgi apparatus.

Glucosylceramide is simplest in the family of glycosphingolipids, and forms the starting point for the biosynthesis of a multitude of more complex glycosphingolipids, by sequentially adding various sugars to the basic glycosylceramide molecule. Degradation of glycosphingolipids also occurs sequentially, by enzymatic removal of the various sugars, until returning the most basic variant, glucosylceramide. As these are all lysosomal processes, irregularities in the biosynthesis and biodegradation of glycosphingolipids, including glucosylceramide, are called lysosomal storage disorders.

Under normal circumstances, the core glycosphingolipid, glucosylceramide, is degraded in lysosomes by acid glucosylceramidase (also called glucocerebrosidase or GBA1, EC 3.2.1.45). In case of lysosomal storage disorders, defects in glycosphingolipid biosynthesis or degradation occurs, resulting in irregular levels of glucosylceramide and/or other glycosphingolipids.

In Gaucher disease, Action Myoclonus Renal Failure Syndrome and Niemann-Pick type C disease, caused by primary inherited and secondary deficiency in GBA1, accumulation of lysosomal glucosylceramide levels leads ultimately also to increased glucosylceramide in the cytosol. Recently, it has been found that this cytosolic glucosylceramide can be degraded by the neutral glucosylceramidase (GBA2, family GH116, as yet no EC-number assigned), which resides in the cytosol. Although its physiological role remains unclear, GBA2 is involved in neuropathological effects observed in several lysosomal storage disorders.

N-substituted deoxynojirimycin derivatives are an important class of molecules in medicinal chemistry and drug discovery with an inhibitory effect on glycosidases. N-(Hydroxyethyl)-deoxynojirimycin

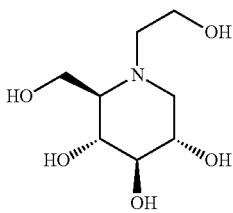

is marketed as Miglitol as an anti-diabetic agent (type 2 diabetes) and acts as a broad-spectrum inhibitor of several intestinal glycosidases (maltase, sucrase, lactase). A severe drawback of Miglitol is that inhibiting intestinal glycosidases results in severe physical discomfort, inherent to their inhibitory action.

N-butyl-deoxynojirimycin (Zavesca)

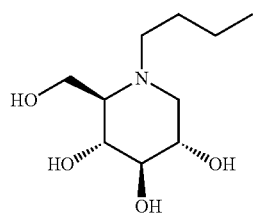

was developed as a glucosylceramide synthase inhibitor (GCS inhibitor) and is used clinically to treat the lysosomal storage disorder Gaucher disease. A disadvantage of this drug is that also intestinal glycosidases are inhibited, which leads to a considerable level of adverse side-effects. Several reports on deoxynojirimycin derivatives bearing various other N-substituents have appeared in recent years, see for instance Yu, W.; Gill, T.; Du, Y.; Ye, H.; Qu, X.; Guo, J.-T.; Cuconati, A.; Zhao, K.; Block, T. M.; Xu. X.; Chang, J. Design, synthesis and biological evaluation of N-alkylated deoxynojirimycin (DNJ) derivatives for the treatment of dengue virus infection. *J. Med. Chem.* 2012, 55, 6061-6075; or Aedes-Guisot, N.; Alonzi, D. S.; Reinkensmeier, G.; Butters, T. D.; Norez, C.; Becq, F.; Shimada, Y.; Nakagawa, S.; Kato, A.; Bleriot, Y.; Sollogoub, M.; Vauzeilles, B. Selection of the biological activity of DNJ neoglycoconjugates through click length variation of the side chain. *Org. Biomol. Chem.* 2011, 9, 5373-5388.

AMP-DNM (compound 1)

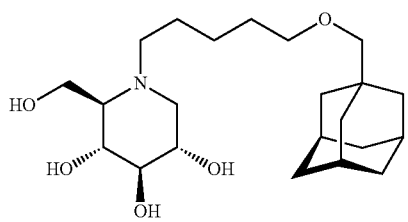

is a superior GCS inhibitor compared to Zavesca. However, AMP-DNM also inhibits GBA1, GBA2, and intestinal glycosidases such as for example lactase, sucrase and isomaltase; inhibition of in particular GBA1 and the intestinal glycosidases is associated with adverse side effects as described above. Also, the potency of AMP-DNM should be increased for therapeutically more effective application.

The C5-epimer of AMP-DNM, (adamantanemethyloxy-pentyl)-L-ido-deoxynojirimycin (ido-AMP-DNM, compound 2)

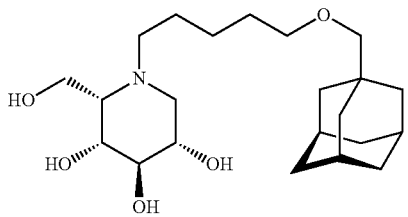

inhibits GCS and GBA2 with about equal potency as compound 1 but with little to no inhibitory activity against the intestinal glycosidases. However, also for ido-AMP-DNM the inhibitory potency is considered low.

Replacing the adamantane group in compound 2, but not in compound 1, with linear alkane substituents (propyl up to nonyl, exemplified by hexyl-substituted deoxynojirimycin derivatives

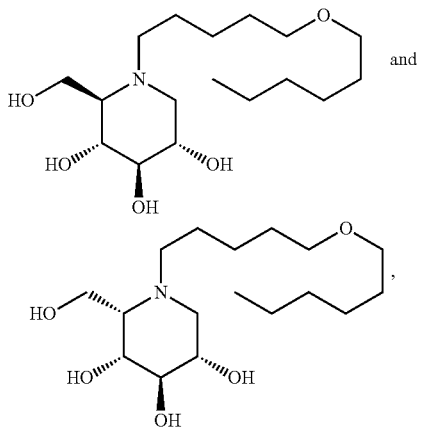

leads to a considerably improved therapeutic window. Whereas GCS activity of both D-gluco and L-ido congeners remains essentially the same, activity against GBA1 drops significantly for the L-ido-compound, but not in the D-gluco-series (see Ghisaidoobe, A.; Bikker, P.; de Bruijn, A. C. J.; Godschalk, F. D.; Rogaar, E.; Guijt, M. C.; Hagens, P.; Halma, J. M.; van't Hart, S. M.; Luitjens, S. B.; van Rixel, V. H. S.; Wijzenbroek, M.; Zweegers, T.; Donker-Koopman, W. E.; Strijland, A.; Boot, R.; van der Marel, G.; Overkleeft, H. S.; Aerts, J. M. F. G.; van den Berg, R. J. B. H. N. Identification of potent and selective glucosylceramide synthase inhibitors from a library of N-alkylated iminosugars, *ACS Med. Chem. Lett.* 2011, 2, 119-123).

Previously, deoxynojirimycin derivatives substituted with adamantane, cholesterol, phenanthrene and cholestanol have been described (see WO2005/040118). A drawback of these compounds is that the inhibitory potency is low, and that their specificity is not sufficiently improved compared with N-alkylated deoxynojirimycins.

SUMMARY OF THE INVENTION

The present invention is directed to novel deoxynojirimycin and deoxygalactonojirimycin derivatives substituted with an non-fused bicyclic aromatic group, or a pharmaceutically acceptable salt, ester, hydrate, and/or solvate thereof. A non-fused bicyclic aromatic group in this context is a group in which two aromatic rings are connected through a single C—C bond, and wherein no other bonds directly or indirectly connect the two aromatic rings.

Deoxynojirimycin and deoxygalactonojirimycin derivatives according to the present invention are N-alkylated D-gluco- or L-ido-deoxynojirimycin or D-deoxygalactonojirimycin with a linear methyloxypentyl group bearing various sidegroups and a non-fused bicyclic aromatic group ("X") on the methyloxy-carbon. Side-groups on the linear pentyl-moiety may be H, F, methyl ("Me") or ethyl ("Et"), and sidegroups on the methyloxy-carbon other than the non-fused bicyclic aromatic group may be H, F, $CF_3$, or $C_1$-$C_8$ linear or branched alkyl.

In particular, deoxynojirimycin derivatives according to the present invention are compounds of general structure I:

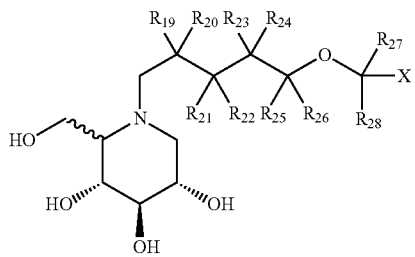

and D-deoxygalactonojirimycin derivatives according to the present invention are compounds of general structure Ia

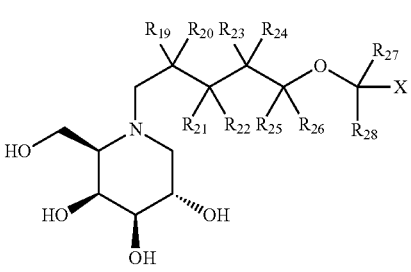

Wherein (for both general structure I and Ia):

each of $R_{19}$-$R_{26}$ is independently selected from H, F, Me or Et;

$R_{27}$ and $R_{28}$ is independently selected from the group consisting of H, F, $CF_3$ and $C_1$-$C_8$ linear or branched alkyl;

X is

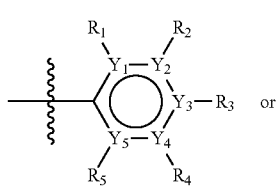

or

-continued

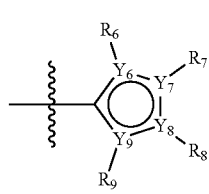
III wherein
  $Y_1$-$Y_5$ are independently selected from the group of C and N-atoms provided that not more than two of $Y_1$-$Y_5$ are a N-atom, and provided that if one or two of $Y_1$-$Y_5$ is a N-atom, the R-group attached to that N-atom is void;
  $Y_6$-$Y_9$ are independently selected from the group of C-, S-, N- and O-atoms and comprise at least one of an S-, N- or O-atom provided that $Y_6$-$Y_9$ comprises at most one S-atom, at most one N-atom and/or at most one O-atom, and provided that if one of $Y_6$-$Y_9$ is a S- or O-atom, the R-group attached to any S-, N- and/or O-atom is void, and provided that if none of $Y_6$-$Y_9$ is a S- or O-atom, the R-group attached to any N-atom is selected from the group consisting of H, $C_1$-$C_8$ linear or branched alkyl, IV and V, and provided that O and S-atoms are not concomitantly present;
  one of $R_1$-$R_9$ is

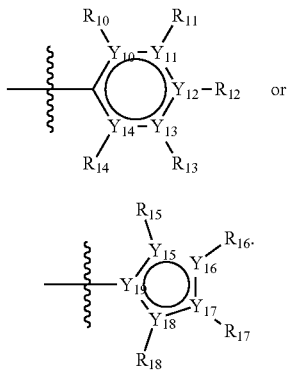

and the remaining of $R_1$-$R_9$ are independently selected from the group consisting of H, F, Cl, Br, I, CN, $CF_3$, $C_1$-$C_8$ linear or branched alkyl, and $C_1$-$C_8$ linear or branched oxyalkyl;
wherein
  $Y_{10}$-$Y_{14}$ are independently selected from the group of C- and N-atoms provided that not more than two of $Y_{10}$-$Y_{14}$ are a N-atom, and provided that if one or two of $Y_{10}$-$Y_{14}$ is a N-atom, the R-group attached to that N-atom is void;
  $Y_{15}$-$Y_{18}$ are independently selected from the group of C-, S-, N- and O-atoms and $Y_{19}$ is selected from the group consisting of a C-atom and a N-atom, provided that $Y_{15}$-$Y_{19}$ comprises at most one S-atom, at most one N-atom and/or at most one O-atom, provided that if one of $Y_{15}$-$Y_{19}$ is a S- or O-atom, the group attached to any S-, N and/or O-atom is void, and provided that if none of $Y_{15}$-$Y_{19}$ is a S- or O-atom, the group attached to any N-atom is selected from the group consisting of H and $C_1$-$C_8$ linear or branched alkyl, and provided that O and S-atoms are not concomitantly present;

$R_{10}$-$R_{18}$ are independently selected from the group consisting of H, F, Cl, Br, I, CN, $CF_3$, $C_1$-$C_8$ linear or branched alkyl or $C_1$-$C_8$ linear or branched oxyalkyl, and/or wherein two of $R_{10}$-$R_{18}$ form a fused alkylene or alkylenedioxy ring on two adjacent atoms of $Y_{10}$-$Y_{18}$;
or a pharmaceutically acceptable salt, ester, hydrate, and/or solvate thereof.

The substitution of a deoxynojirimycin or deoxygalactonojirimycin derivative with a non-fused bicyclic aromatic group has an unexpected effect on the level of cytosolic or lysosomal glucosylceramide and/or higher glycosphingolipids, relative to known deoxynojirimycin derivatives, such as deoxynojirimycin derivatives substituted with a linear alkyl, cholesterol, phenanthrene or adamantylgroup group. The group of glycosphingolipids, for the scope of the present invention, consists of the simplest glycosphingolipid, glycosylceramide, and the higher glycosphingolipids, which are further glycosylated variants of glucosylceramide.

The cellular level of cytosolic or lysosomal glucosylceramide and/or higher glycosphingolipids, for the scope of the present invention, is determined by the collective action of the human cytosolic glucosylceramide synthesizing enzyme glucosylceramide synthase ("GCS", EC 2.4.1.80), the human lysosomal glucosylceramide degrading enzyme acid glucosylceramidase (glucocerebrosidase, "GBA1", EC 3.2.1.45) and the human cytosolic glucosylceramide degrading enzyme neutral glucosylceramidase ("GBA2"), as well as by the action of the enzymes for the biosynthesis and -degradation of higher glycosphingolipids.

The level of cytosolic or lysosomal glucosylceramide and/or higher glycosphingolipids is altered by the compounds of the present invention, because these compounds display an increased inhibitory potency towards GCS, and/or an increased inhibitory potency towards GBA2, and/or a decreased inhibitory potency towards GBA1, relative to known deoxynojirimycin derivatives of the same (D-gluco, L-ido or D-galacto) configuration. Because GCS-mediated formation of glucosylceramide is the key first step in formation of glycosphingolipids (see FIG. 1), any disease associated with irregular levels of cytosolic or lysosomal glucosylceramide and/or higher glycosphingolipids is a suitable target for the compounds of the present invention.

This change in inhibitory potency is beneficial for the treatment of diseases which are associated with an irregular level of cytosolic or lysosomal glucosylceramide and/or higher glycosphingolipids. Such diseases are often associated with increased relative activity of GCS and/or GBA2, either by a decreased activity of GBA1 or by increased presence of ceramide through other biochemical routes, as is summarized in FIG. 1. Diseases which are associated with an irregular level of cytosolic or lysosomal glucosylceramide and/or other glycosphingolipids can be classified in four groups:

1) Lysosomal storage disorders, among which Gaucher disease, Fabry disease, Tay-Sachs disease, Sandhoff disease, GM1 gangliosidosis, Sialidosis, Niemann Pick disease type C and AMRF ("Action Myoclonic Renal Failure Syndrome"), display glycosphingolipid accumulation and are therefore suitably treated with the compounds of the present invention.

2) The symptoms of diseases collectively classed as metabolic syndrome (obesity, insulin resistance, hyperlipidemia, hypercholesterolemia, polycystic kidney disease and chronic inflammation) are associated with increased levels cytosolic or lysosomal glucosylceramide and/or other glycosphingolipids, because excessive interaction of the insulin receptor with sialylated glycosphingolipids, so-called gangliosides, inhibits insulin signalling. This is associated with diabetes type II, for which reason the compounds of the present invention are suitable to treat symptoms of metabolic syndrome and/or prevent diabetes type II.

3) Neurodenegerative disorders, such as Parkinson disease and Lewy-body dementia are viable targets for compounds of the present invention, because these diseases are associated with impairment of GBA1.

4) Atherosclerosis

The change in inhibitory potency of the compounds of the present invention is beneficial for the treatment of the collection of diseases defined above because the increased inhibition of GCS reduces glucosylceramide production, which decreases the level of glycosphingolipids, including glucosylceramide, in the lysosomes or the cytosol.

Alternatively or additionally, the compounds of the present invention display inhibition of non-lysosomal GBA2, whose over-activity during impaired lysosomal degradation of glucosylceramide is pathogenic in neurons.

These separate effects individually contribute in a compound-dependent, varying degree to a single and general effect of all compounds according to the present invention on the level of cytosolic or lysosomal glucosylceramide and/or higher sphingolipids. Therefore these compounds have a beneficial effect in the treatment of diseases associated with irregular levels of cytosolic or lysosomal glucosylceramide and/or higher glycosphingolipids.

BRIEF DESCRIPTION OF THE FIGURES

FIG. 1. Schematic overview of glycosphingolipid biosynthesis and biodegradation, and a selection of lysosomal storage disorders associated with enzyme defects in this biochemical system.

DETAILED DESCRIPTION

According to the present invention, compounds with increased beneficial effect on an irregular level of cytosolic or lysosomal glucosylceramide and/or higher glycosphingolipids, which can suitably be used in the treatment of diseases, are compounds of general structure I or Ia, preferably I:

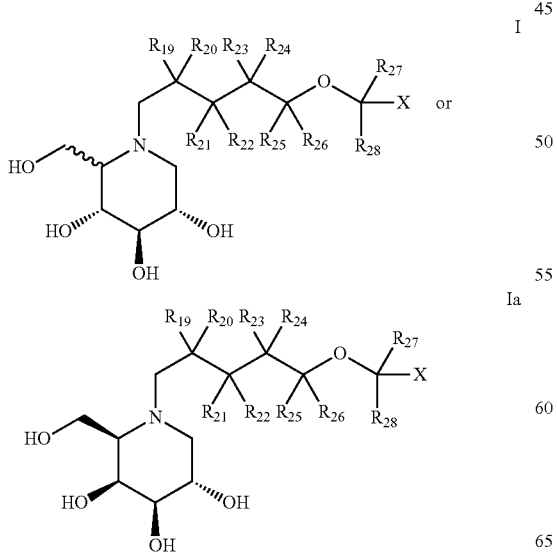

wherein:
each of $R_{19}$-$R_{26}$ is independently selected from H, F, Me or Et;
$R_{27}$ and $R_{28}$ is independently selected from the group consisting of H, F, $CF_3$ and $C_1$-$C_8$ linear or branched alkyl;
X is

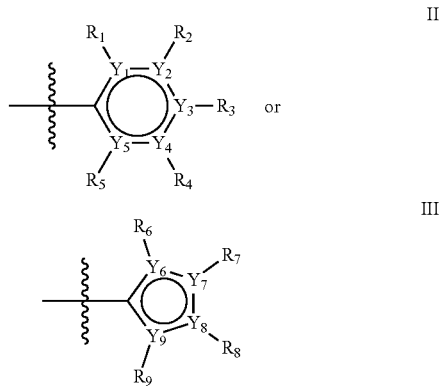

wherein
$Y_1$-$Y_5$ are independently selected from the group of C and N-atoms provided that not more than two of $Y_1$-$Y_5$ are a N-atom, and provided that if one or two of $Y_1$-$Y_5$ is a N-atom, the R-group attached to that N-atom is void;
$Y_6$-$Y_9$ are independently selected from the group of C-, S-, N- and O-atoms and comprise at least one of an S-, N- or O-atom provided that $Y_6$-$Y_9$ comprises at most one S-atom, at most one N-atom and/or at most one O-atom, and provided that if one of $Y_6$-$Y_9$ is a S- or O-atom, the R-group attached to any S-, N- and/or O-atom is void, and provided that if none of $Y_6$-$Y_9$ is a S- or O-atom, the R-group attached to any N-atom is selected from the group consisting of H, $C_1$-$C_8$ linear or branched alkyl, IV and V, and provided that O and S-atoms are not concomitantly present;
one of $R_1$-$R_9$ is

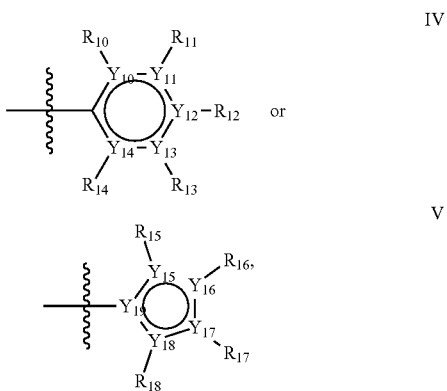

and the remaining of $R_1$-$R_9$ are independently selected from the group consisting of H, F, Cl, Br, I, CN, $CF_3$, $C_1$-$C_8$ linear or branched alkyl, and $C_1$-$C_8$ linear or branched oxyalkyl;
wherein
$Y_{10}$-$Y_{14}$ are independently selected from the group of C- and N-atoms provided that not more than two of $Y_{10}$-$Y_{14}$ are a N-atom, and provided that if one or two of $Y_{10}$-$Y_{14}$ is a N-atom, the R-group attached to that N-atom is void;

$Y_{15}$-$Y_{18}$ are independently selected from the group of C-, S-, N- and O-atoms and $Y_{19}$ is selected from the group consisting of a C-atom and a N-atom, provided that $Y_{15}$-$Y_{19}$ comprises at most one S-atom, at most one N-atom and/or at most one O-atom, provided that if one of $Y_{15}$-$Y_{19}$ is a S- or O-atom, the group attached to any S-, N and/or O-atom is void, and provided that if none of $Y_{15}$-$Y_{19}$ is a S- or O-atom, the group attached to any N-atom is selected from the group consisting of H or $C_1$-$C_8$ linear or branched alkyl, and provided that O and S-atoms are not concomitantly present;

$R_{10}$-$R_{18}$ are independently selected from the group consisting of H, F, Cl, Br, I, CN, $CF_3$, $C_1$-$C_8$ linear or branched alkyl or $C_1$-$C_8$ linear or branched oxyalkyl, and/or wherein two of $R_{10}$-$R_{18}$ form a linear or branched fused alkylene or alkylenedioxy ring on two adjacent atoms of $Y_{10}$-$Y_{18}$;

or a pharmaceutically acceptable salt, ester, hydrate, and/or solvate thereof.

In this definition, "Me" stands for methyl, "Et" stands for ethyl, and $C_1$-$C_8$ linear or branched alkyl defines groups consisting of at most 8 C-atoms, which may be connected linearly, or branched, including cyclically branched, and the appropriate number of hydrogen atoms to attain a saturated group. A group is designated "void" when this group is absent, such as in the case when an R-groups attached to a variably defined atom "Y" is absent for a certain "Y" as defined above. "Independently selected" is applicable to the situation where multiple alternatives exist for more than one choice, and bears the meaning that each choice from the list of alternatives for a group in one position is not influenced in any way by a choice from the same list of alternatives for a group in another position.

$C_1$-$C_8$ alkyl or oxyalkyl in all cases may be either linear or branched, even if not expressly stated such, and are saturated groups unless otherwise mentioned. Examples of $C_1$-$C_8$ linear or branched alkylgroups are methyl ("Me" or $CH_3$), ethyl ("Et" or $CH_2CH_3$), iso-propyl (iPr or $CH(CH_3)_2$), and other saturated linear or branched alkylgroups known in the art.

Oxyalkyl denotes an alkyl group comprising one or more C—O—C ether bonds, wherein at least one of the C atoms is part of a saturated alkyl group, and wherein the other C-atom is either part of a saturated alkyl group, or forms part of the atom onto which the group is substituted. Examples of $C_1$-$C_8$ linear or branched oxyalkylgroups are methoxy (—OMe), ethoxy (—OEt), n-propyloxy (—OnPr), iso-propyloxy (—OiPr), —$OCH_2OCH_a$, O-t-butyl (—OtBu) and other linear or branched saturated groups comprising ether bonds as known in the art.

For the purpose of clarity and a concise description features are described herein as part of the same or separate embodiments, however, it will be appreciated that the scope of the invention may include embodiments having combinations of all or some of the features described. This applies to both the definition of the compound and to the definition of disease groups, pharmacological excipients and compositions, and their combinations, unless explicitly otherwise mentioned. In particular, the general compound definitions I and Ia entail as embodiments many alternatives or groups of alternatives. In the context of the present invention, all possible combinations can be made of the alternatives or groups of alternatives defined for separate parts of general structure I and Ia, for the simple reason that the number of permutations is such that not all combinations can be described explicitly.

Between compounds of general structure I and of general structure Ia, compounds of general structure I are preferred. Alternatively, the invention is directed to compounds of general structure Ia.

The general compound definition I pertains to deoxynojirimycin derivatives of either the L-ido configuration IX:

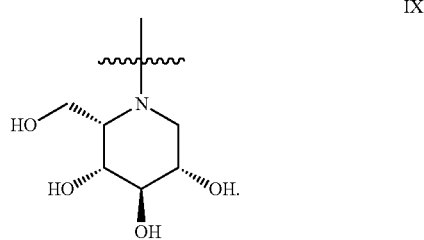 [SMILES: *N1C[C@H](O)[C@@H](O)[C@H](O)[C@@H]1CO]

IX or the D-gluco configuration XI:

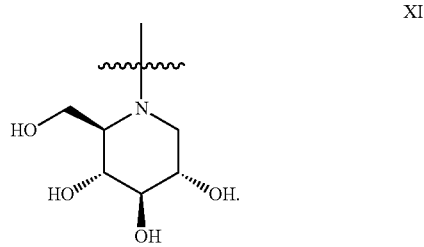 [SMILES: *N1C[C@H](O)[C@@H](O)[C@H](O)[C@H]1CO]

XI

Preferred deoxynojirimycin derivatives (general structure I) are deoxynojirimycin derivatives of the L-ido configuration.

The linear methyloxypentyl group bearing various sidegroups is situated at the nitrogen atom of the deoxynojirimycin or deoxygalactonojirimycin moiety as defined in general structures I and Ia. The various, independently selected sidegroups $R_{19}$-$R_{26}$ may be H, F, methyl ("Me") or ethyl ("Et"). Preferably, the sidegroups are either H or F or Me, and most preferably, the sidegroups are either H or F.

The various and independently selected side groups on the methyloxy-carbon, $R_{27}$ and $R_{28}$, are selected the group consisting of H, F, $CF_3$ and $C_1$-$C_8$ linear or branched alkyl. Preferably, $R_{27}$ and $R_{28}$ are independently selected from the group consisting of H, F and $C_1$-$C_8$ linear or branched alkyl, more preferably from the group consisting of H and $C_1$-$C_8$ linear or branched alkyl, and even more preferably from the group consisting of H and $C_1$-$C_4$ linear or branched alkyl, and most preferably from the group consisting of H, methyl, ethyl, propyl, and iso-propyl. In a much preferred embodiment, $R_{27}$ and $R_{28}$ are different, resulting in a chiral methyloxy carbon of either R or S configuration.

The group "X" is a non-fused bicyclic aromatic group with various and independently selected sidegroups. The group "X" comprises two aromatic or heteroaromatic rings, the first of which is located on the methyloxycarbon together with the side groups $R_{27}$ and $R_{28}$. The second aromatic ring of group "X" is coupled through a single bond to the first ring, resulting in a non-fused bicyclic aromatic group.

The first ring of group X may be a six-ring of general structure II

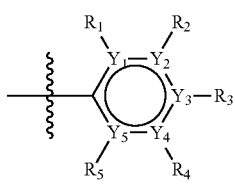

wherein Y₁-Y₅ are independently selected from the group of C and N-atoms provided that not more than two of Y₁-Y₅ are a N-atom, and provided that if one or two of Y₁-Y₅ is a N-atom, the R-group attached to that N-atom is void. Thus, general structure II may be any of the group consisting of

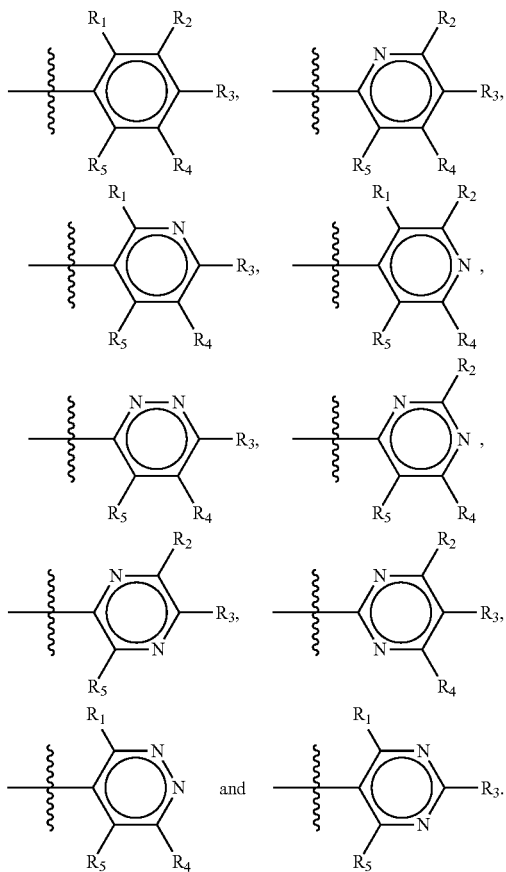

Preferably however, in general structure II not more than one of Y₁-Y₅ are a N-atom, provided that if one of Y₁-Y₅ is a N-atom, the R-group attached to that N-atom is void, so that a preferred first aromatic ring is one of the group consisting of

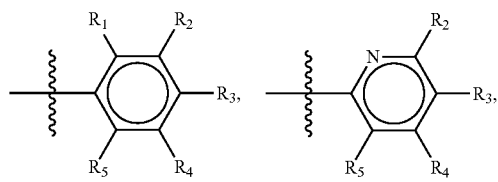

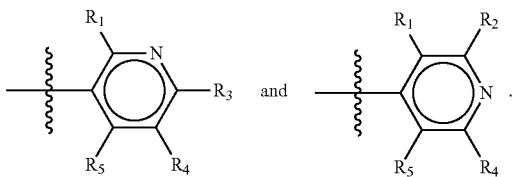

Most preferred however is a first aromatic ring of general structure II which is a benzene ring,

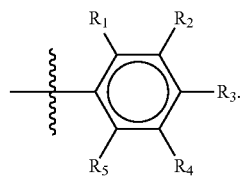

Alternatively, the first aromatic ring of group X may be a five-ring of general structure III

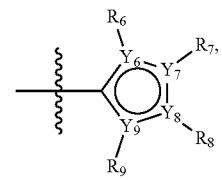

wherein Y₆-Y₉ are independently selected from the group of C-, S-, N- and O-atoms and comprise at least one of an S-, N- or O-atom provided that Y₆-Y₉ comprises at most one S-atom, at most one N-atom and/or at most one O-atom, and provided that if one of Y₆-Y₉ is a S- or O-atom, the R-group attached to any S-, N- and/or O-atom is void, and provided that if none of Y₆-Y₉ is a S- or O-atom, the R-group attached to any N-atom is selected from the group consisting of H, C₁-C₈ linear or branched alkyl, IV and V, and provided that O and S-atoms are not concomitantly present.

Not concomitantly present in this context means that O and S atoms are not present in the same aromatic ring (III or V, see below) at the same time. This definition amounts to aromatic five-ring systems in which one or two heteroatoms S, N or O are present, but with the proviso that if two heteroatoms are present, the heteroatoms must be different, so either one S-atom and one N-atom, or one O-atom and one N-atom. It follows that an aromatic ring of general structure III may be any of the group consisting of

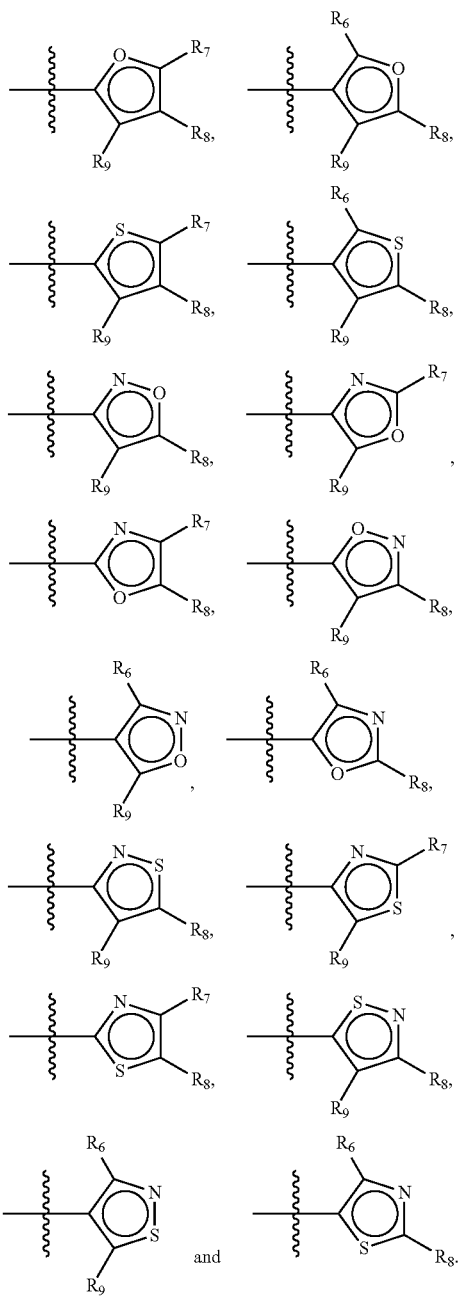
Preferably, if the first ring of group X is a structure of general structure III, it is preferably one of the group consisting of
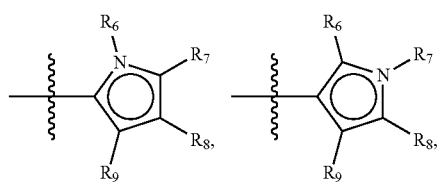
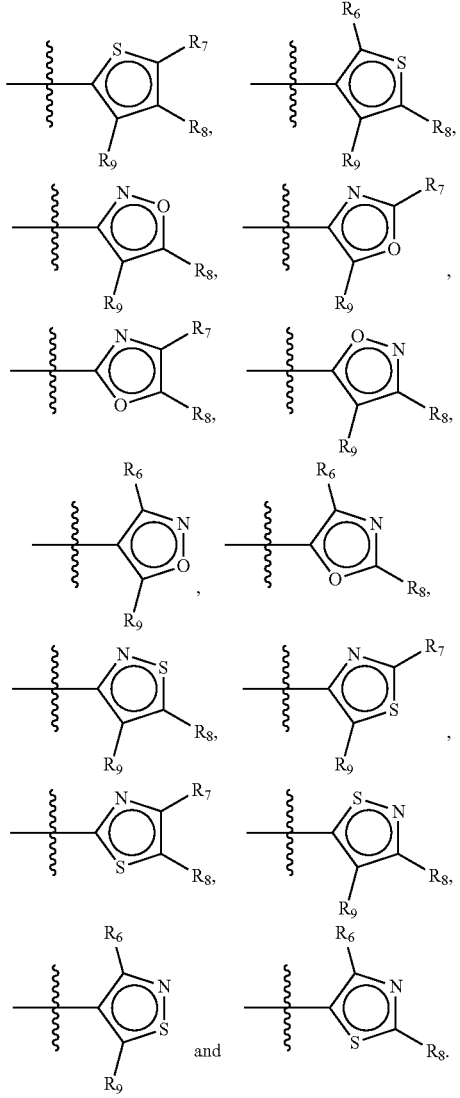
More preferably, if the first ring of group X is a structure of general structure III, it is preferably one of the group consisting of
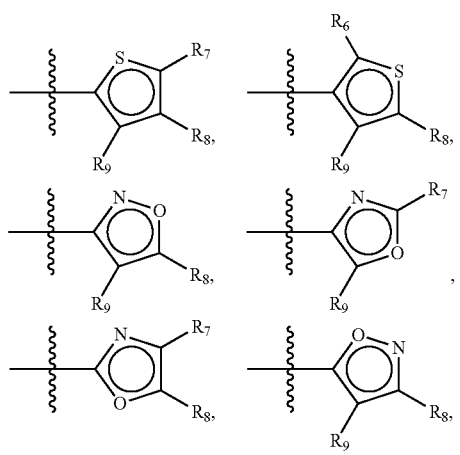

-continued

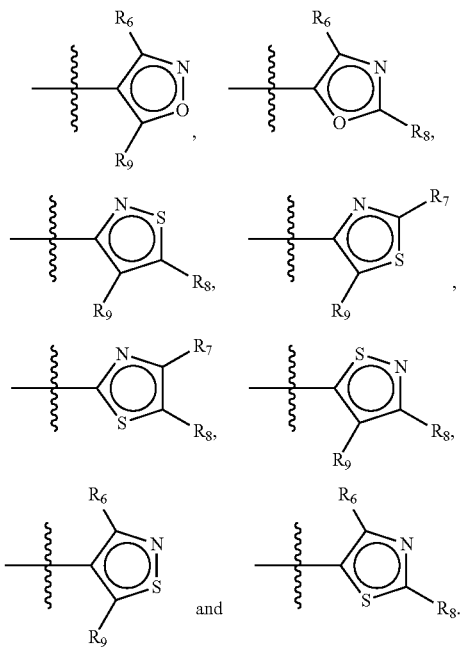

Most preferably however, if the first ring of group X is a structure of general structure III, it is preferably one of the group consisting of

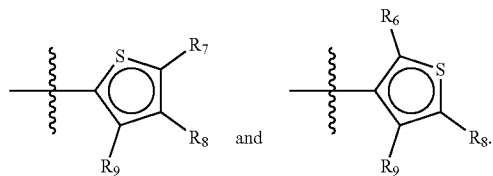

For the first ring of group X, groups of the group consisting of

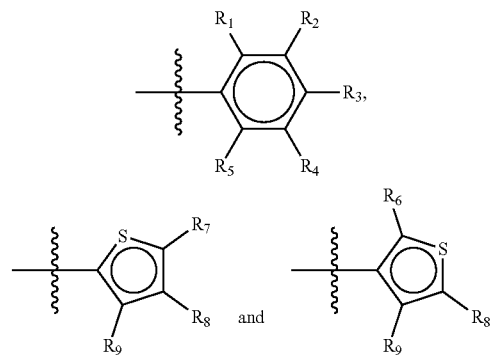

are highly preferred.

Groups $R_1$-$R_9$ ($R_1$-$R_5$ in case of a first aromatic ring of general structure II and $R_6$-$R_9$ in case of a first aromatic ring of general structure III) are selected such that one of $R_1$-$R_9$ is the second ring of group X, which is either a ring of general structure IV, or a ring of general structure V:

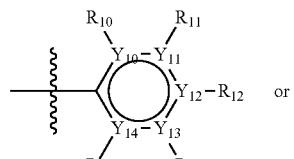

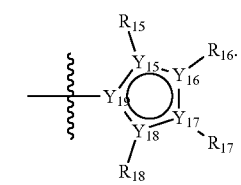

The remaining of $R_1$-$R_9$, which are all groups which are not general structure IV or V, are independently selected from the group consisting of H, F, Cl, Br, I, CN, $CF_3$, $C_1$-$C_8$ linear or branched alkyl, and $C_1$-$C_8$ linear or branched oxyalkyl.

Preferably, the remaining of $R_1$-$R_9$ are independently selected from the group consisting of H, F, $CF_3$, $C_1$-$C_8$ linear or branched alkyl, and $C_1$-$C_8$ linear or branched oxyalkyl, even more preferably the remaining of $R_1$-$R_9$ are independently selected from the group consisting of H, F, $CF_3$, methyl, ethyl, iso-propyl, tert-butyl, methoxy, ethoxy, iso-propyloxy and tert-butyloxy, and most preferably the remaining of $R_1$-$R_9$ are independently selected from the group consisting of H, F and $CF_3$.

In one alternative, the second ring of group X is selected from the group represented by general structure IV, in which $Y_{10}$-$Y_{14}$ are independently selected from the group of C- and N-atoms provided that not more than two of $Y_{10}$-$Y_{14}$ are a N-atom, and provided that if one or two of $Y_{10}$-$Y_{14}$ is a N-atom, the R-group attached to that N-atom is void.

Thus, general structure IV may be any of the group consisting of

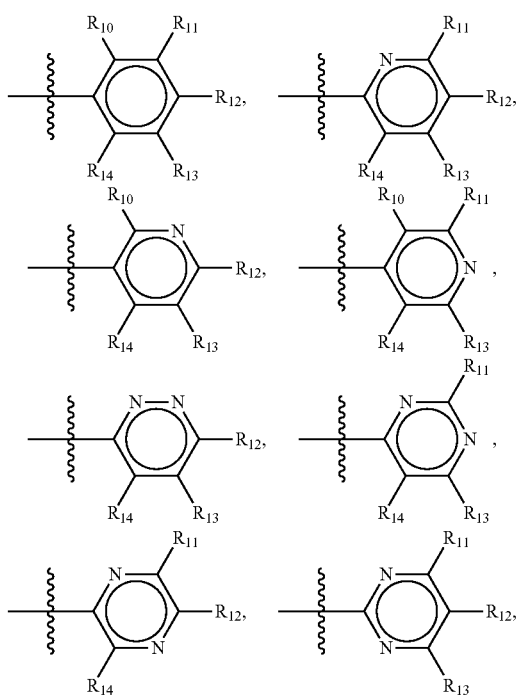

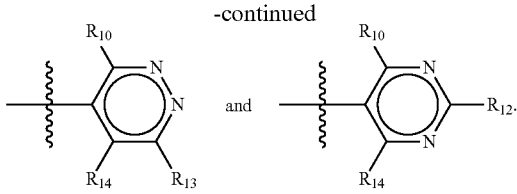

Preferably however, in general structure IV not more than one of $Y_1$-$Y_5$ are a N-atom, provided that if one of $Y_1$-$Y_5$ is a N-atom, the R-group attached to that N-atom is void, so that a preferred second aromatic ring in group X, in case of a group of general structure IV, is one of the group consisting of

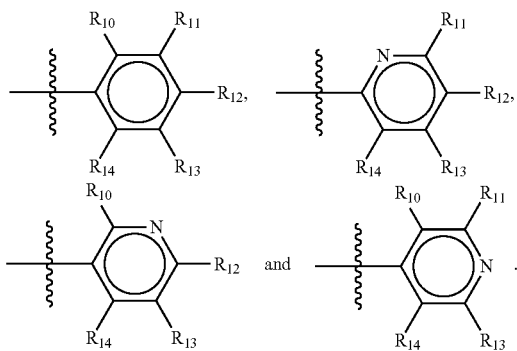

Most preferred however in case of a group of general structure IV is a second aromatic ring which is a benzene ring,

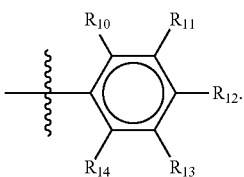

In another alternative, the second ring of group X is selected from the group represented by general structure V, wherein $Y_{15}$-$Y_{18}$ are independently selected from the group of C-, S-, N- and O-atoms and $Y_{19}$ is selected from the group consisting of a C-atom and a N-atom, provided that $Y_{15}$-$Y_{19}$ comprises at most one S-atom, at most one N-atom and/or at most one O-atom, provided that if one of $Y_{15}$-$Y_{19}$ is a S- or O-atom, the group attached to any S-, N and/or O-atom is void, and provided that if none of $Y_{15}$-$Y_{19}$ is a S- or O-atom, the group attached to any N-atom is selected from the group consisting of H or $C_1$-$C_8$ linear or branched alkyl, and provided that O and S-atoms are not concomitantly present.

Not concomitantly present in this context as well means that O and S atoms are not present in the same aromatic ring (III or V) at the same time. This definition amounts to aromatic five-ring systems in which one or two heteroatoms S, N or O are present, but with the proviso that if two heteroatoms are present, the heteroatoms must be different, so either one S-atom and one N-atom, or one O-atom and one N-atom. It follows that aromatic rings of general structure V may be any of the group consisting of

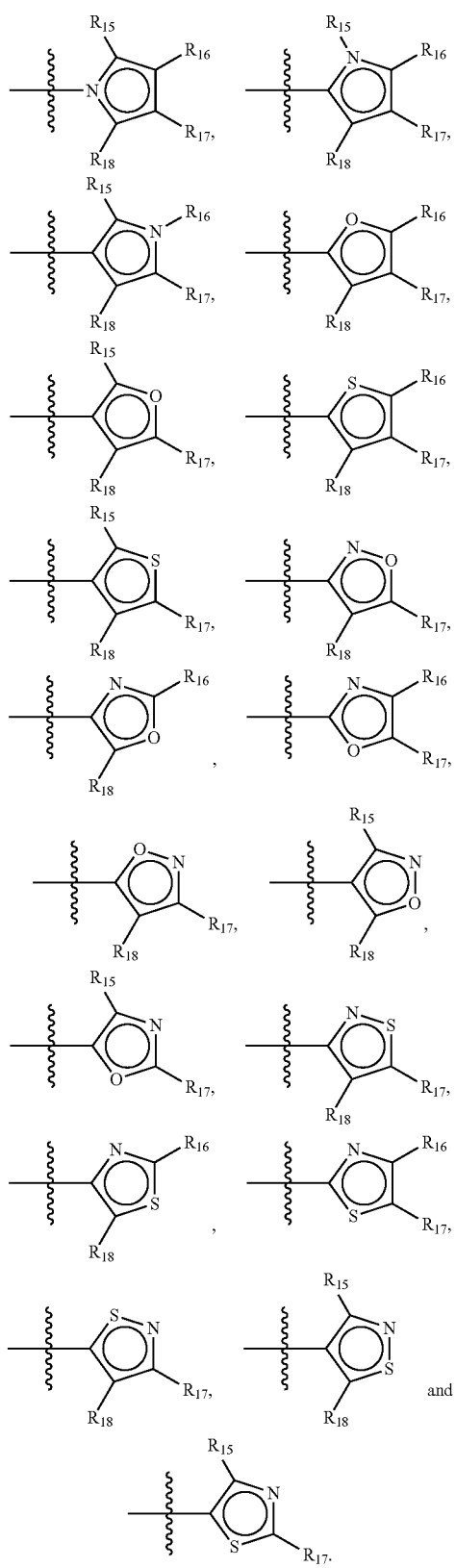

Preferably, if the second ring of group X is a structure of general structure V, it is preferably one of the group consisting of

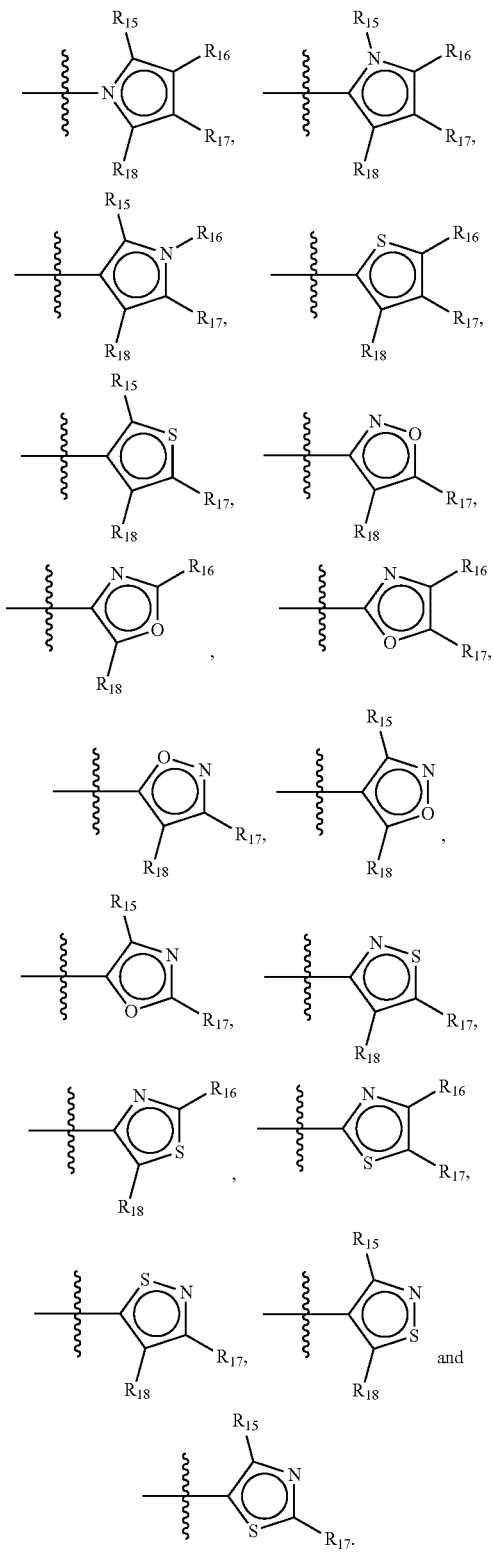

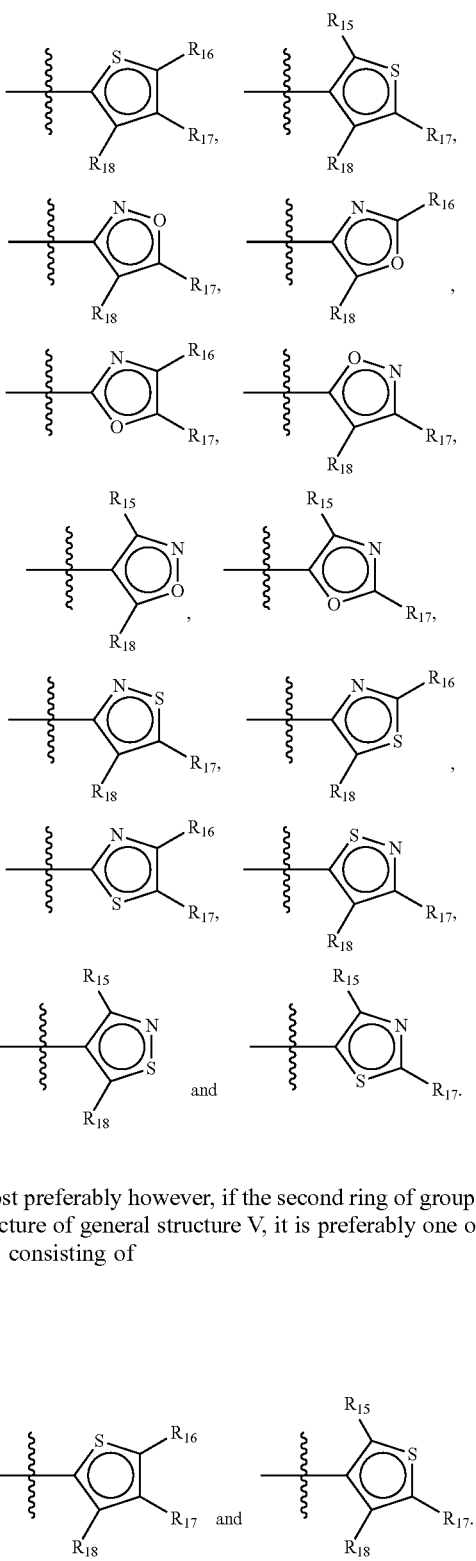

More preferably, if the second ring of group X is a structure of general structure V, it is preferably one of the group consisting of Most preferably however, if the second ring of group X is a structure of general structure V, it is preferably one of the group consisting of For the second aromatic ring of group X, it is highly preferred if the aromatic ring is one of the group consisting of

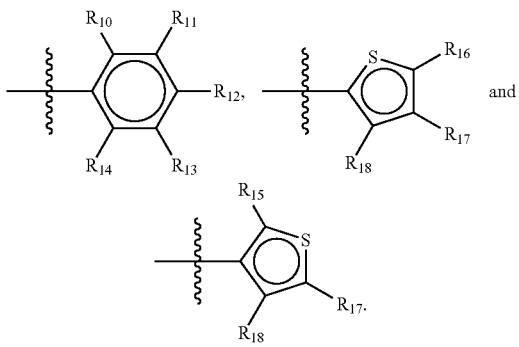

Groups $R_{10}$-$R_{18}$ ($R_{10}$-$R_{14}$ in case of a second aromatic ring of general structure IV and $R_{15}$-$R_{18}$ in case of a second aromatic ring of general structure V) are selected such $R_{10}$-$R_{18}$ are independently selected from the group consisting of H, F, Cl, Br, I, CN, $CF_3$, $C_1$-$C_8$ linear or branched alkyl or $C_1$-$C_8$ linear or branched oxyalkyl, and/or wherein two of $R_{10}$-$R_{18}$ form a fused alkylene or alkylenedioxy ring on two adjacent atoms of $Y_{10}$-$Y_{18}$.

A linear or branched fused alkylene or alkylenedioxy ring on two adjacent atoms is understood to mean a cyclic exterior ring fused onto the second aromatic ring by two adjacent atoms $Y_{10}$-$Y_{11}$, $Y_{11}$-$Y_{12}$, $Y_{12}$-$Y_{13}$, $Y_{13}$-$Y_{14}$, $Y_{15}$-$Y_{16}$, $Y_{16}$-$Y_{17}$ or $Y_{17}$-$Y_{18}$. This cyclic group can be a four- five- six or seven-ring structure, which is either fused through two O-atoms on the adjacent atoms $Y_n$-$Y_{n+1}$, or through C-atoms. The C-atoms in the cyclic exterior rings may be branched by further $C_1$-$C_8$ alkyl, branched alkyl or cycloalkyl portion, as is known in the art. Without limiting the invention to only these structures, a few examples of a linear or branched fused alkylene or alkylenedioxy ring on two adjacent atoms $Y_n$-$Y_{n+1}$ are:

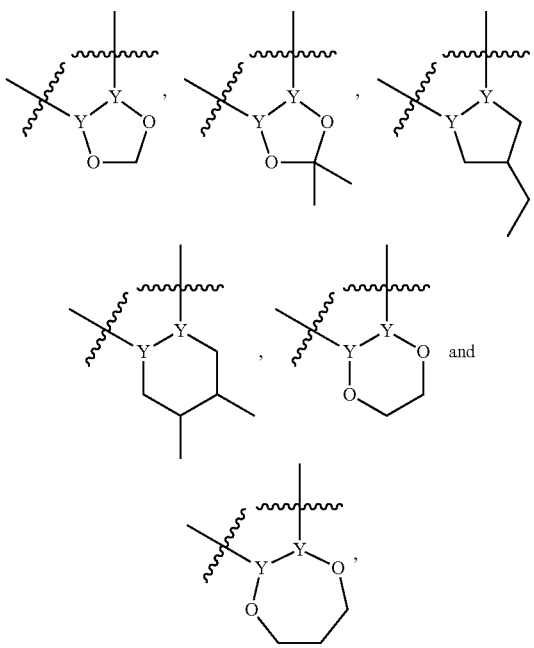

wherein Y represents two adjacent atoms of $Y_{10}$-$Y_{18}$ as defined above. Preferably, a linear or branched fused alkylene or alkylenedioxy ring is one of the group consisting of

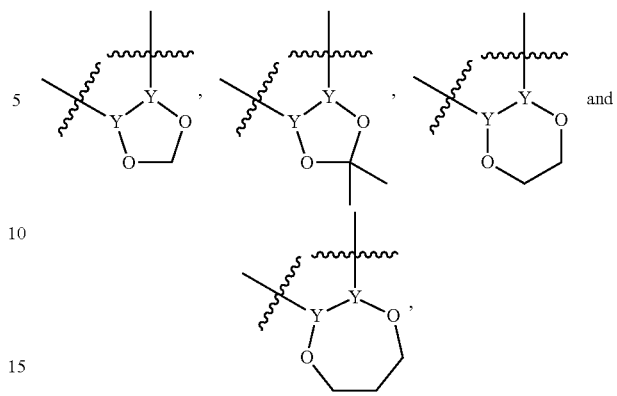

Further preferably, the remaining of $R_{10}$-$R_{18}$ which are not a linear or branched fused alkylene or alkylenedioxy ring are independently selected from the group consisting of H, F, $CF_3$, $C_1$-$C_8$ linear or branched alkyl, and $C_1$-$C_8$ linear or branched oxyalkyl. Even more preferably $R_{10}$-$R_{18}$ are independently selected from the group consisting of H, F, $CF_3$, methyl, ethyl, iso-propyl, tert-butyl, methoxy, ethoxy, iso-propyloxy and tert-butyloxy.

Most preferably however, $R_{10}$-$R_{18}$ are independently selected from the group consisting of H, F and $CF_3$.

For all compounds of general structure I and general structure Ia according to the present invention, a pharmaceutically acceptable salt, ester, hydrate, and/or solvate must generally be considered equally applicable as the general structure I or Ia. The selection of an appropriate salt, ester, hydrate or solvate, as is known in the art, may be an opportunity to modulate the pharmaceutical properties of compounds of general structure I or Ia, for instance by improving bioavailability, stability, manufacturability, and/or patient compliance. Pharmaceutically acceptable salts, esters, hydrates, and/or solvates are known in the art.

Pharmaceutically acceptable salts are salts, comprising a positively and a negatively charged ion, wherein one of the positively and negatively charged ions is a ionic form of general structure I or Ia, and wherein the other of the positively and negatively charged ions is a pharmaceutically acceptable counterion. A pharmaceutically acceptable counterion is a ionic organic or inorganic species, which has no substantial effect on the body when administered in the form of a pharmaceutical. A pharmaceutically acceptable counterion may be for example acetate, bromide, camsylate, chloride, formate, fumarate, maleate, mesylate, nitrate, oxalate, phosphate, sulfate, tartrate, thiocyanate, tosylate, ammonium, arginate, diethylammonium, protonated ethylenediamine, or piperazinium.

Pharmaceutically acceptable salts may also be based on a complex of a compound of general structure I or Ia with a pharmaceutically acceptable acid or base, such as for example acetic acid, adipic acid, 4-amino salicylic acid, arachidic acid, ascorbic acid, aspartic acid, behenic acid, benzoic acid, butyric acid, camphoric acid, camphorsulfonic acid, capric acid, caproic acid, caprylic acid, cerotic acid, cinnamic acid (trans), citric acid, formic acid, fumaric acid, gentisic acid, glutamic acid, glutaric acid, hydrobromic acid, hydrochloric acid, isobutyric acid, lauric acid, lignoceric acid, maleic acid, malic acid, malonic acid, mandelic acid, methane sulfonic acid, myristic acid, nitric acid, oxalic acid, palmitic acid, phosphoric acid, pivalic acid, propionic acid, p-toluene sulfonic acid, pyroglutamic acid, salicylic acid, sebacic acid, stearic acid, succinic acid, sulfuric acid or tartaric acid, ammonia, betaine, choline, diolamine, diethylamine, ethanolamine, ethylenediamine, 1H-imidazole, piperazine or trolamine.

A pharmaceutically acceptable salt is preferably a solid, but may also occur in solution.

Pharmaceutically acceptable esters are compounds of general structure I or Ia, wherein at least one free hydroxyl group has been esterified with a pharmaceutically acceptable acid, as is known in the art. Suitable pharmaceutically acceptable acids are for instance acetic acid, adipic acid, 4-amino salicylic acid, arachidic acid, ascorbic acid, aspartic acid, behenic acid, benzoic acid, butyric acid, camphoric acid, camphorsulfonic acid, capric acid, caproic acid, caprylic acid, cerotic acid, cinnamic acid (trans), citric acid, formic acid, fumaric acid, gentisic acid, glutamic acid, glutaric acid, hydrobromic acid, hydrochloric acid, isobutyric acid, lauric acid, lignoceric acid, maleic acid, malic acid, malonic acid, mandelic acid, methane sulfonic acid, myristic acid, nitric acid, oxalic acid, palmitic acid, phosphoric acid, pivalic acid, propionic acid, p-toluene sulfonic acid, pyroglutamic acid, salicylic acid, sebacic acid, stearic acid, succinic acid, sulfuric acid or tartaric acid.

Pharmaceutically acceptable hydrates are crystals comprising compounds of general structure I or Ia that incorporate water into the crystalline structure without chemical alteration of compounds of general structure I or Ia. Suitable hydrates can be hydrates in which the molar ratio of compounds of general structure I or Ia to water is 1:1-1:20, preferably 1:1-1:10, more preferably 1:1-1:6. Thus, a preferred hydrate may be for instance a monohydrate, dihydrate, trihydrate, tetrahydrate, pentahydrate, hexahydrate, heptahydrate, octahydrate, nonahydrate or decahydrate.

Pharmaceutically acceptable solvates are compounds of general structure I or Ia as a solute in a pharmaceutically acceptable solution, which are complexed to one or more solvent molecules. Suitable pharmaceutically acceptable solvents to form solvates are for instance acetic acid, acetone, anisole, 1-butanol, 2-butanol, butyl acetate, tert-butylmethyl ether, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate or water.

Suitable examples of a group X which is suitable in the context of the present invention are

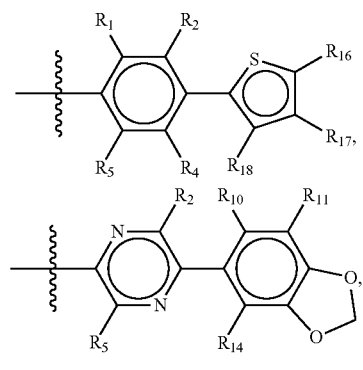

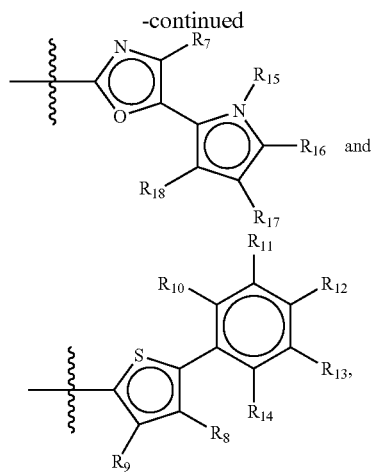

but it is to be understood that all possible permutations of the groups II and III, and IV and V, as defined above for general structure I and Ia, are considered as part of the invention.

Preferred compounds of the present invention are compounds according to general formula I and Ia defined above, wherein X is a biphenyl according to general structures VI, VII or VIII as in:

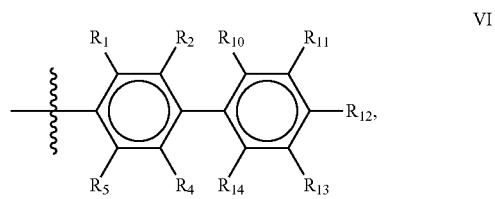

VI

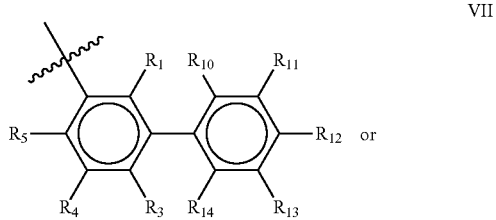

VII

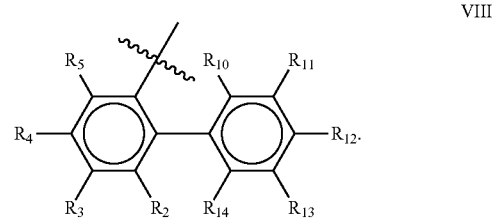

VIII wherein each of the group consisting of $R_1$-$R_4$ are independently selected from the group consisting of H, F, Cl, Br, I, CN, $CF_3$, and $C_1$-$C_8$ linear or branched alkyl, and $R_{10}$-$R_{14}$ are independently selected from the group consisting of H, F, Cl, Br, I, CN, $CF_3$, and $C_1$-$C_8$ linear or branched alkyl and/or wherein two of the group consisting of $R_{10}$-$R_{14}$ form a linear or branched fused alkylene or alkylenedioxy ring on two adjacent atoms.

Preferably for the biphenyls VI, VII and VIII, either all of $R_1$-$R_4$ or all of $R_{10}$-$R_{14}$ are selected from the group consisting of C, H and $CF_3$, and most preferably, all of $R_1$-$R_4$ and $R_{10}$-$R_{14}$ are selected from the group consisting of C, H and $CF_3$.

Among the biphenyls, biphenyls of general structure VI as defined above are particularly preferred.
Further preferred compounds are compounds according to general formula I or Ia defined above, wherein X is one of the group consisting of
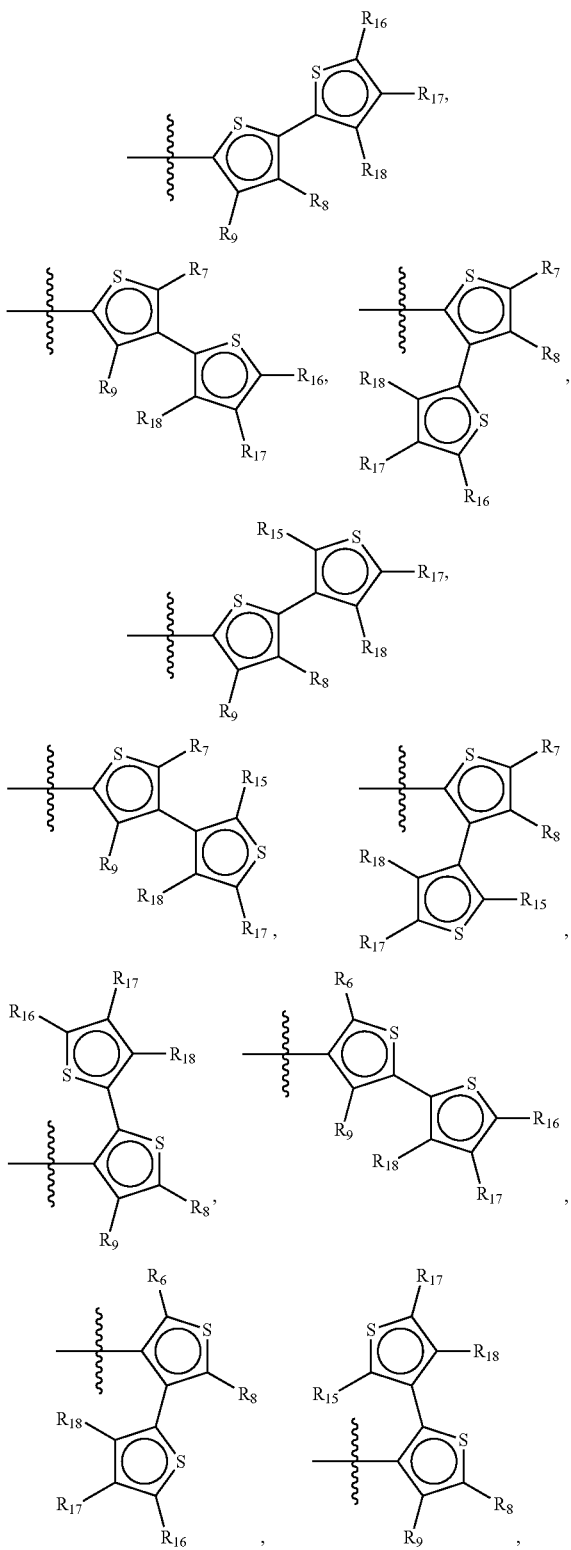
-continued
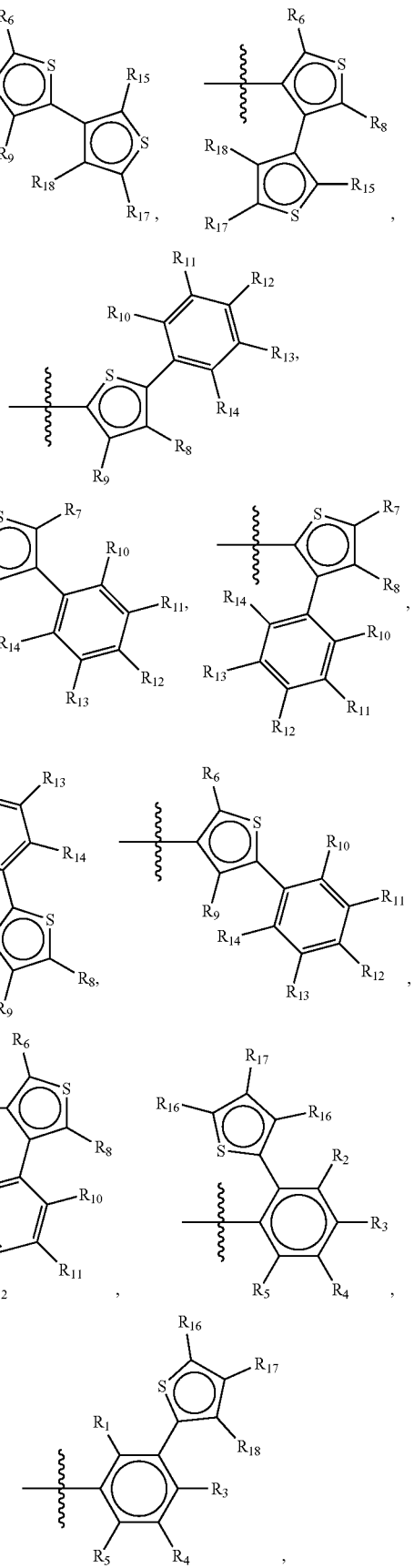

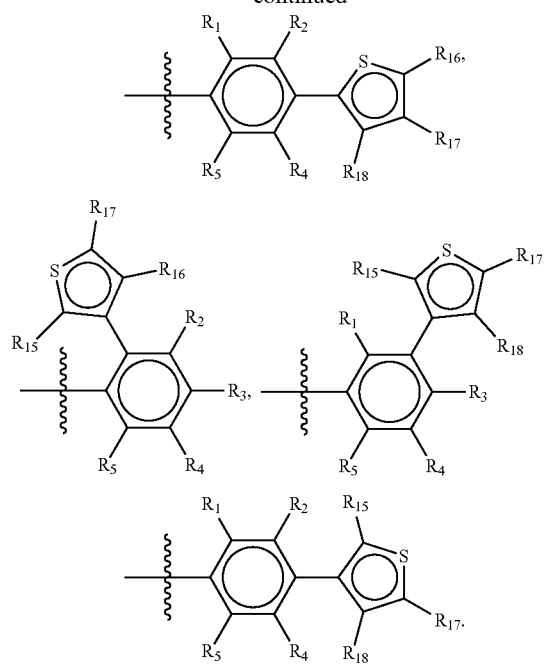
Further preferred compounds are compounds according to general formula I or Ia defined above, wherein X is one of the group consisting of
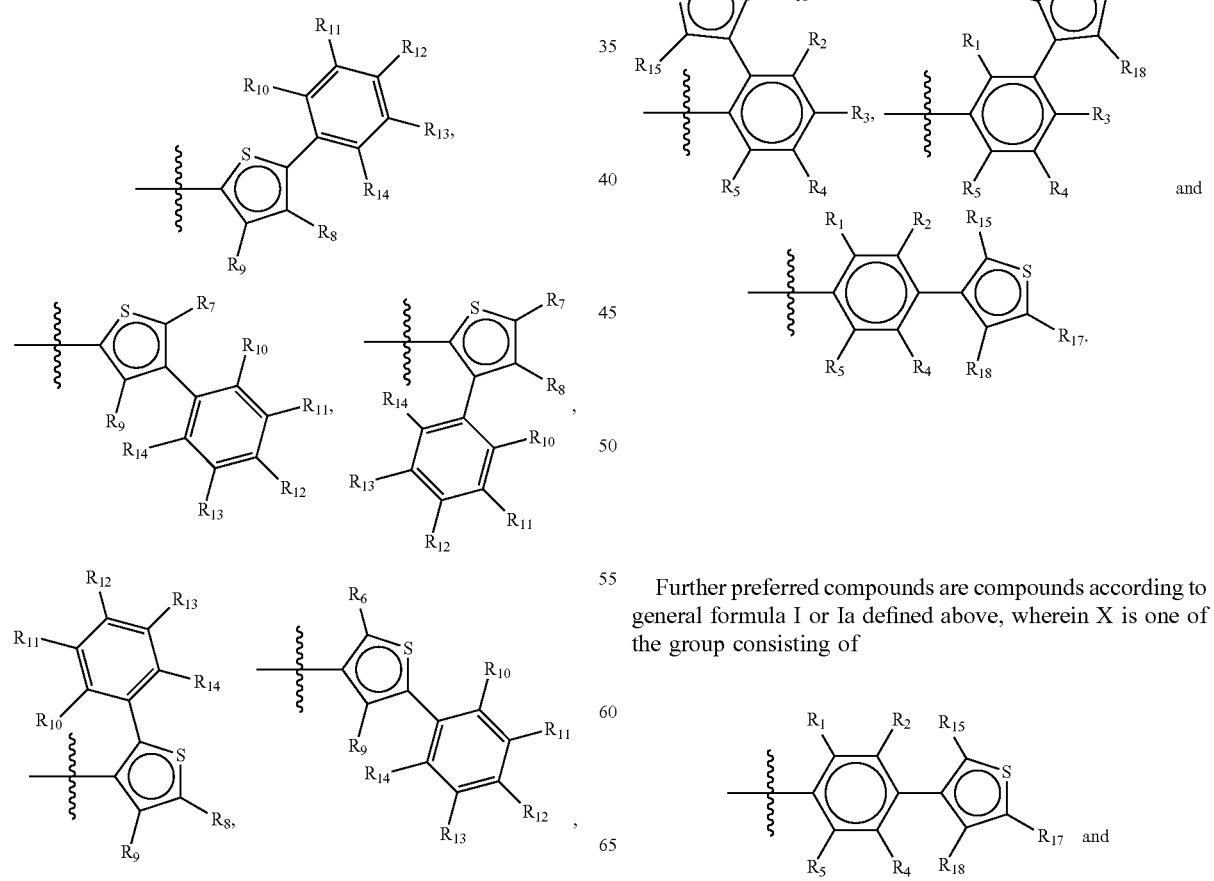
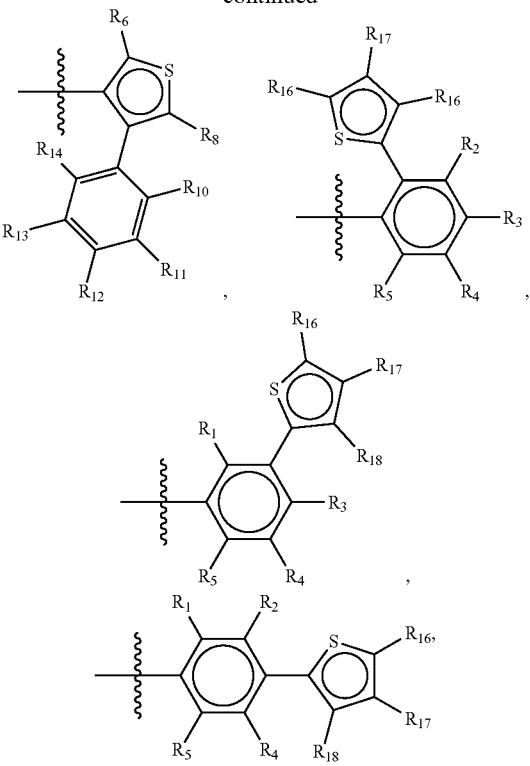
Further preferred compounds are compounds according to general formula I or Ia defined above, wherein X is one of the group consisting of
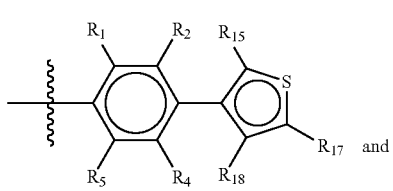

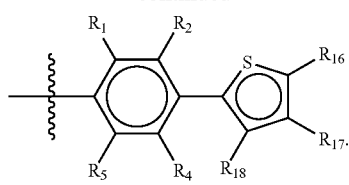
Alternatively, preferred compounds of the present invention are compounds according to general formula I or Ia defined above, wherein $R_{27}$ is H and $R_{28}$ is methyl.
Highly preferred compounds of the present invention are compounds selected from the group consisting of
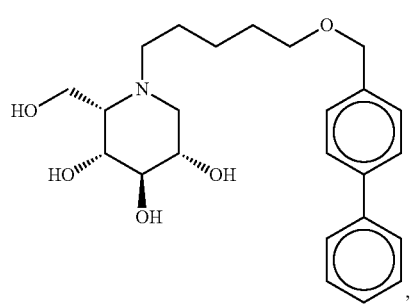
,
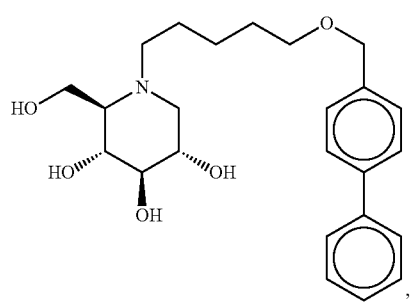
,
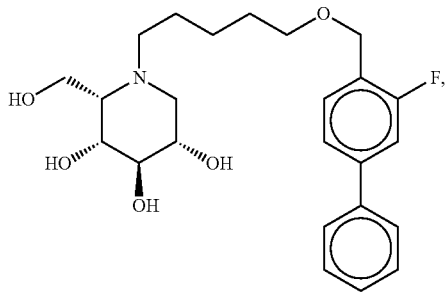
,
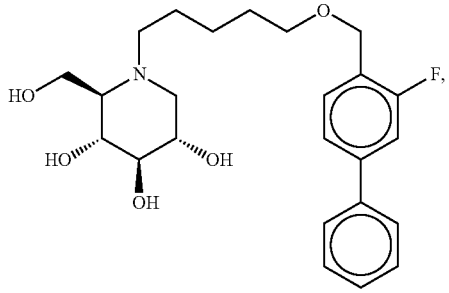
,
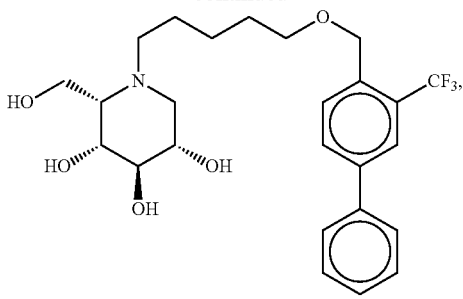
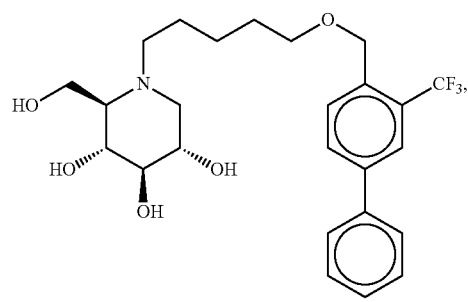
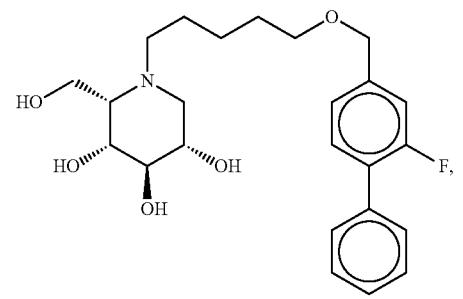
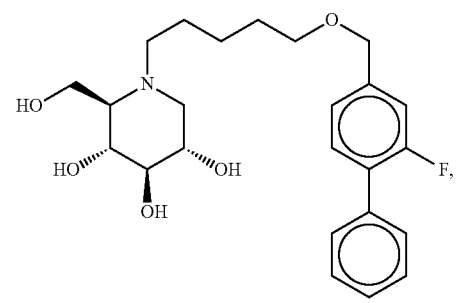
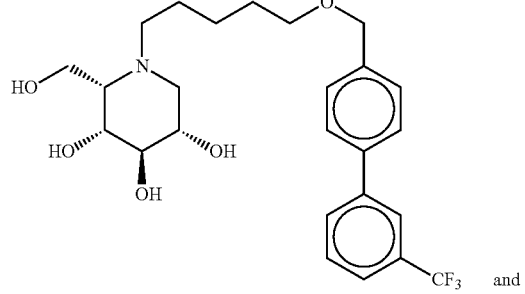
and 31
-continued
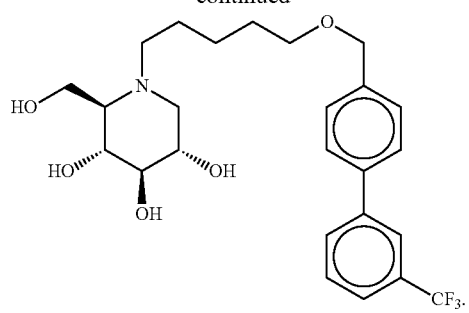
As has been mentioned above, and as is valid for all compounds of the present invention, also within this group the deoxynojirimycin derivative with an L-ido configuration is particularly preferred, i.e compounds
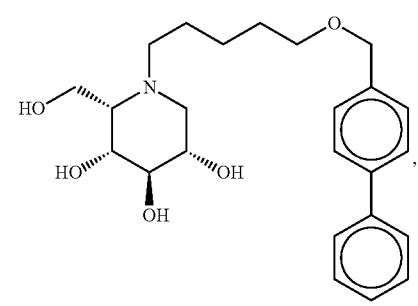
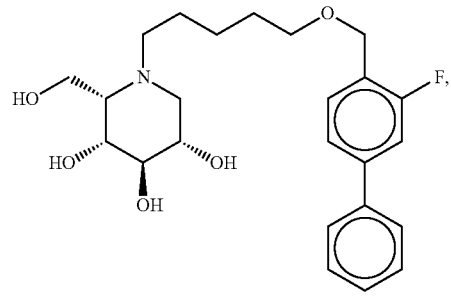
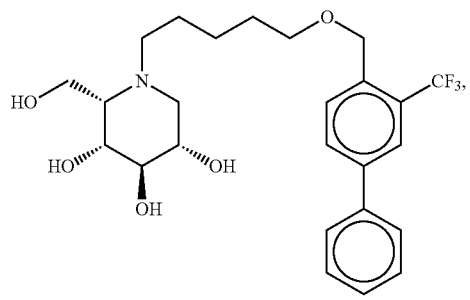
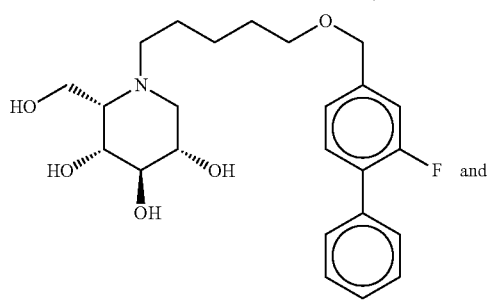
32
-continued
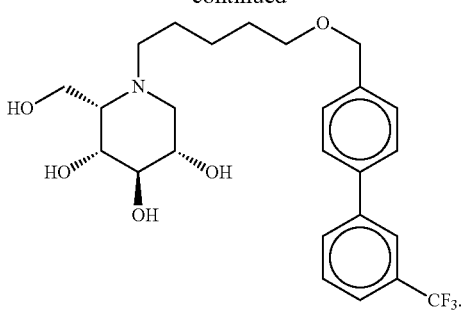
Alternatively, highly preferred compounds of general structure Ia are
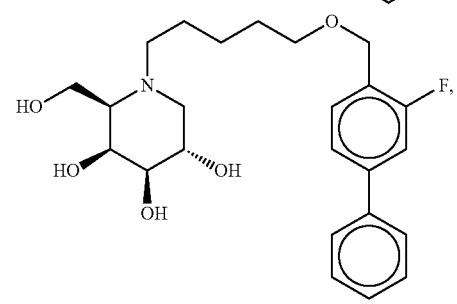
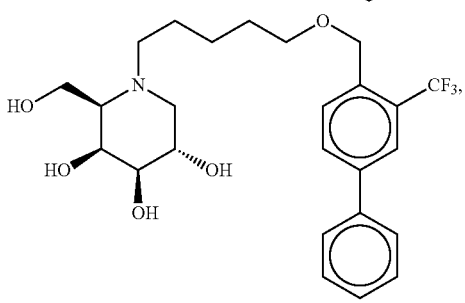
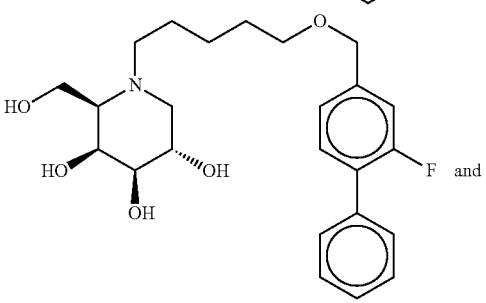

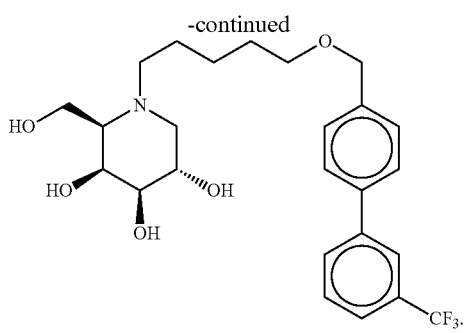

Synthesis of Compounds of General Structure I

Compounds of general structure I and Ia can be synthesized following established procedures using different starting materials. Briefly, quantities of deprotected deoxynojirimycin of the D-gluco configuration can be prepared as described in Wennekes, T.; Lang, B.; Leeman, M.; van der Marel, G. A.; Smits, E.; Weber, M.; van Wiltenburg, J.; Wolberg, M.; Aerts, J. M. F. G.; Overkleeft. H. S. "Large-scale synthesis of the glucosylceramide synthase inhibitor N-[5-(adamantan-1yl-methoxy)-pentyl]-1-deoxynojirimycin" Org. Process Res. Dev. 2008, 12, 414-423 and in Wennekes, T.; van den Berg, R. J. B. H. N.; Donker, W.; van der Marel, G. A.; Strijland, A.; Aerts, J. M. F. G.; Overkleeft, H. S. "Development of adamantan-1-yl-methoxy-functionalized 1-deoxynojirimycin derivatives as selective inhibitors of glucosylceramide metabolism in man", J. Org. Chem. 2007, 72, 1088-1097.

Quantities of deprotected deoxynojirimycin of the L-ido configuration can be prepared as described in Wennekes, T.; Meijer, A. J.; Groen, A. K.; Boot, R. G.; Groener, J. E.; van Eijk, M.; Ottenhoff, R.; Bijl, N.; Ghauharali, K.; Song, H.; O'Shea, T. J.; Liu, H.; Yew, N.; Copeland, D.; van den Berg, R. J.; van der Marel, G. A.; Overkleeft, H. S.; Aerts, J. M. "Dual-action lipophilic iminosugar improves glycemic control in obese rodents by reduction of visceral glycosphingolipids and buffering of carbohydrate assimilation", J. Med. Chem. 2010, 53, 689-698.

Deprotected D-deoxygalactonojirimycin can be prepared as described by H. S. Overkleeft, J. van Wiltenburg and U. K. Pandit in "A facile transformation of sugar lactones to azasugars", Tetrahedron, Volume 50, Issue 14, pages, 4215-4224 (1994).

D-deoxygalactonojirimycin has the structure

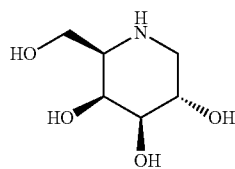

The respective N-substituents with a leaving group on the primary carbon (the carbon between the carbon bearing groups $R_{19}$ and $R_{20}$, and the N-atom of deoxynojirimycin) can be made by standard chemical procedures. One suitable, exemplary procedure is provided as Route A, which provides a synthetic protocol for compounds of general structure XII, in which all of $Y_1$-$Y_{19}$ and $R_1$-$R_{28}$ are as defined elsewhere unless otherwise provided. This general structure XII can be reacted by nucleophilic substitution with deoxynojirimycin of the D-gluco or the L-ido configuration (IX or XI) to provide compounds of general structure I. A general synthetic protocol for route A is provided in the examples. Subsequently, the reaction product is purified by standard chemical procedures, such as for instance column chromatography or preparatory high performance liquid chromatography.

Preferred compounds of general structure XII have a group Z which is a halide, in particular bromide or iodide, or a mesylate, tosylate or triflate. Preferably, Z is I or Br. The compounds of general structure XII can be purified by chromatography using for instance ethylacetate and petroleum ether, and should preferably have a purity of at least 80%, more preferably at least 90% and most preferably at least 95%.

An alternative route to compounds of general structure I is provided as route B, which is described in detail in the examples. In route B, aromatic compounds XXII or XXIII, in which $Y_1$-$Y_9$, $R_1$-$R_9$ and $R_{19}$-$R_{28}$ are as defined elsewhere unless otherwise provided, are coupled to the pentyl spacer moiety XIX or XX. Deprotection provides compound XXV, which can be reacted with deoxynojirimycin of the D-gluco or L-ido configuration (XI or XI) to provide compound XXVI. Subsequent Suzuki coupling with boronic acid or ester compounds of the second aromatic ring moieties XV or XVI, in which all of $Y_{10}$-$Y_{19}$ and $R_{10}$-$R_{18}$ are as defined elsewhere unless otherwise provided, thus provides compound I.

Both for route A and in route B, suitable protecting groups "Q" are known in the art, and include for example methoxymethyl, p-methoxybenzyl, p-methoxybenzyloxymethyl, methoxyethoxymethyl, tetrahydropyranol, tetrahydrofuranyl, allyl, p-methoxyphenyl, naphtyl, methoxyphenyldipehnylmethyl, triisopropylsilyl, tertbutyldimethylsilyl, tertbutyldiphenylsilyl, triphenylmethyl, and are preferably chosen from naphtyl, p-methoxybenzyl, methoxydiphenylmethyl, tripheynlmethyl.

Both for route A and in route B, suitable leaving groups "Z" are known in the art, and comprise preferably halides, in particular bromide or iodide, mesylates, tosylates and triflates. More preferably, bromide or iodide are used as leaving group, most preferably bromide.

Suzuki cross-coupling chemistry (step 1 in route A or step 9 in route B) can suitably be carried out under an protective atmosphere, such as argon or nitrogen. Z-substituted compound XIII, XIV or XXVI, boronic acid or ester XV or XVI and a paladium compound, such as for example Pd(PPh$_3$)$_4$, are combined in the presence of a strong base, such as NaOMe, and allowed to react. The crude product can be isolated and purified, preferably by chromatography.

Alkylation of deprotected deoxynojirimycin IX or XI (step 5 in route A or step 8 in route B) can suitably be carried out by stirring deprotected deoxynojirimycin at a temperature between 20 and 154° C., preferably 80-85° C., in the presence of a compound of general structure XII or XXV in a polar non-protic solvent, for instance DMF. A suitable concentration is between 0.01 and 2 M, preferably 0.1-0.5 M. Further preferably, approximately stoichiometric amounts of reactants are used. The presence of base is highly preferred. Preferably, an excess of base is used, such as a two-fold excess, a three-fold excess, or an even higher excess amount. Suitable bases include for example potassium carbonate, sodiumcarbonate, potassium hydrogencarbonate, sodiumhydrogencarbonate, trietylamine, diisopropylethylamine, diazobicycloundecene diazobicyclononene.

Step 3 in route A and step 6 in route B are nucleophilic substitutions well-known in the art, which may for example be effected by deprotonation of a hydroxyl group of compound XVII, XX or XXII, and subsequent reaction with Z-substituted compound XVI II, XIX or XX III.

Step 2 in route A is optional, and may be used in case a compound of structure XX is used to include the pentyl spacer moiety. It may be achieved by treatment with methanesulfonyl chloride/toluenesulfonyl chloride or transferring OH in a halogen by using e.g. tetrabromomethane/triphenylphospine.

Step 4 in route A and step 7 in route B are conversions well-known in the art, the procedure of which is dependent on the identity of protecting group Q.

Route A and route B can also be applied using deprotected deoxygalactonojirimycin instead of deprotected deoxynojirimycin of the L-ido or D-gluco configuration, to obtain compounds of general structure Ia (synthesis not shown).

Thus, the invention also provides a method of making a deoxynojirimycin derivative of general structure I or Ia, preferably I as defined above, comprising alkylation of D-gluco or L-ido deoxynojirimycin or D-deoxygalactonojirimycin, preferably D-gluco or L-ido deoxynojirimycin, with an alkyl halide of structure

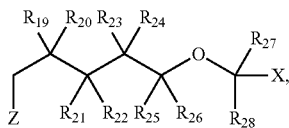

XII wherein
Z=mesylate, tosylate, triflate or halide, preferably Br or I
each of $R_{19}$-$R_{26}$ is independently selected from H, F, Me or Et;
$R_{27}$ and $R_{28}$ is independently selected from the group consisting of H, F, $CF_3$ and $C_1$-$C_8$ linear or branched alkyl;
X is

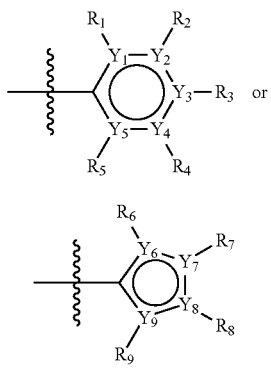

II

III wherein
$Y_1$-$Y_5$ are independently selected from the group of C and N-atoms provided that not more than two of $Y_1$-$Y_5$ are a N-atom, and provided that if one or two of $Y_1$-$Y_5$ is a N-atom, the R-group attached to that N-atom is void;
$Y_6$-$Y_9$ are independently selected from the group of C-, S-, N- and O-atoms and comprise at least one of an S-, N- or O-atom, provided that $Y_6$-$Y_9$ comprises at most one S-atom, at most one N-atom and/or at most one O-atom, and provided that if one of $Y_6$-$Y_9$ is a S- or O-atom, the R-group attached to any S-, N- and/or O-atom is void, and provided that if none of $Y_6$-$Y_9$ is a S- or O-atom, the R-group attached to any N-atom is selected from the group consisting of H, $C_1$-$C_8$ linear or branched alkyl, IV and V, and provided that O and S-atoms are not concomitantly present;
one of $R_1$-$R_9$ is

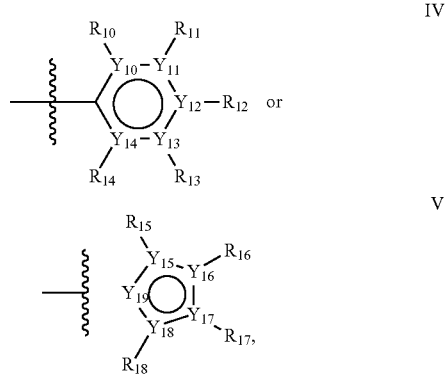

IV

V and the remaining of $R_1$-$R_9$ are independently selected from the group consisting of H, F, Cl, Br, I, CN, $CF_3$, $C_1$-$C_8$ linear or branched alkyl and $C_1$-$C_8$ linear or branched oxyalkyl;
wherein
$Y_{10}$-$Y_{14}$ are independently selected from the group of C- and N-atoms provided that not more than two of $Y_{10}$-$Y_{14}$ are a N-atom, and provided that if one or two of $Y_{10}$-$Y_{14}$ is a N-atom, the R-group attached to that N-atom is void;
$Y_{15}$-$Y_{18}$ are independently selected from the group of C-, S-, N- and O-atoms and $Y_{19}$ is selected from the group consisting of a C-atom and a N-atom, provided that $Y_{15}$-$Y_{19}$ comprises at most one S-atom, at most one N-atom and/or at most one O-atom, provided that if one of $Y_{15}$-$Y_{19}$ is a S- or O-atom, the group attached to any S-, N and/or O-atom is void, and provided that if none of $Y_{15}$-$Y_{19}$ is a S- or O-atom, the group attached to any N-atom is selected from the group consisting of H or $C_1$-$C_8$ linear or branched alkyl, and provided that O and S-atoms are not concomitantly present;
$R_{10}$-$R_{18}$ are independently selected from the group consisting of H, F, Cl, Br, I, CN, $CF_3$, $C_1$-$C_8$ linear or branched alkyl or $C_1$-$C_8$ linear or branched oxyalkyl, and/or wherein two of $R_{10}$-$R_{18}$ form a linear or branched fused alkylene or alkylenedioxy ring on two adjacent atoms of $Y_{10}$-$Y_{18}$.

Alternatively, the invention provides a method of making a deoxynojirimycin derivative of general structure I or Ia, preferably I, as defined above, comprising alkylation of D-gluco or L-ido deoxynojirimycin or D-deoxygalactonojirimycin, preferably D-gluco or L-ido deoxynojirimycin, with an alkyl halide of structure

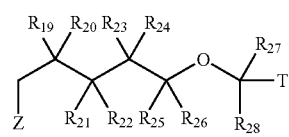

XXV wherein
Z=mesylate, tosylate, triflate or halide, preferably Br or I
each of $R_{19}$-$R_{26}$ is independently selected from H, F, Me or Et;
$R_{27}$ and $R_{28}$ is independently selected from the group consisting of H, F, $CF_3$ and $C_1$-$C_8$ linear or branched alkyl;
T is

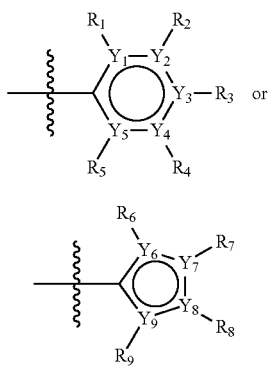

II

III wherein
$Y_1$-$Y_5$ are independently selected from the group of C and N-atoms provided that not more than two of $Y_1$-$Y_5$ are a N-atom, and provided that if one or two of $Y_1$-$Y_5$ is a N-atom, the R-group attached to that N-atom is void;
$Y_6$-$Y_9$ are independently selected from the group of C-, S-, N- and O-atoms and comprise at least one of an S-, N- or O-atom, provided that $Y_6$-$Y_9$ comprises at most one S-atom, at most one N-atom and/or at most one O-atom, and provided that if one of $Y_6$-$Y_9$ is a S- or O-atom, the R-group attached to any S-, N- and/or O-atom is void, and provided that if none of $Y_6$-$Y_9$ is a S- or O-atom, the R-group attached to any N-atom is selected from the group consisting of H, $C_1$-$C_8$ linear or branched alkyl, IV and V, and provided that O and S-atoms are not concomitantly present;
one of $R_1$-$R_9$ is a halide, preferably bromide or iodide, or a mesylate, tosylate or triflate, and the remaining of $R_1$-$R_9$ are independently selected from the group consisting of H, F, Cl, Br, I, CN, $CF_3$, $C_1$-$C_8$ linear or branched alkyl and $C_1$-$C_8$ linear or branched oxyalkyl;
and subsequently comprising a coupling reaction with a boronic acid or ester from the group consisting of

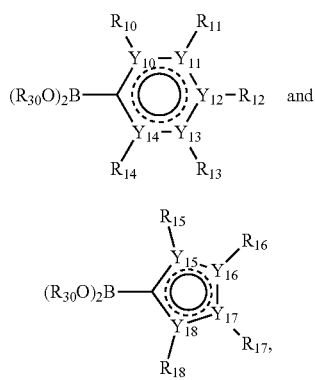

XV and

XVI wherein
$Y_{10}$-$Y_{14}$ are independently selected from the group of C- and N-atoms provided that not more than two of $Y_{10}$-$Y_{14}$ are a N-atom, and provided that if one or two of $Y_{10}$-$Y_{14}$ is a N-atom, the R-group attached to that N-atom is void;
$Y_{15}$-$Y_{18}$ are independently selected from the group of C-, S-, N- and O-atoms and $Y_{19}$ is selected from the group consisting of a C-atom and a N-atom, provided that $Y_{15}$-$Y_{19}$ comprises at most one S-atom, at most one N-atom and/or at most one O-atom, provided that if one of $Y_{15}$-$Y_{19}$ is a S- or O-atom, the group attached to any S-, N and/or O-atom is void, and provided that if none of $Y_{15}$-$Y_{19}$ is a S- or O-atom, the group attached to any N-atom is selected from the group consisting of H or $C_1$-$C_8$ linear or branched alkyl, and provided that O and S-atoms are not concomitantly present;
$R_{10}$-$R_{18}$ are independently selected from the group consisting of H, F, Cl, Br, I, CN, $CF_3$, $C_1$-$C_8$ linear or branched alkyl or $C_1$-$C_8$ linear or branched oxyalkyl, and/or wherein two of $R_{10}$-$R_{18}$ form a linear or branched fused alkylene or alkylenedioxy ring on two adjacent atoms of $Y_{10}$-$Y_{18}$;
$R_{30}$ is selected from the group consisting of H, linear or branched alkyl, and an aromatic group according to general structure IV or V.

Compounds of general structure I or Ia to be applied in the present invention are preferably as pure as possible, which means a purity of at least 95%, preferably at least 98%, more preferably at least 99%, and most preferably at least 99.5%.

The Inhibitory Potency of the Compounds of General Structure I

The effect of bicyclic non-fused aromatic substitution as provided by the present invention is determined by measuring the half maximal inhibitory concentration ($IC_{50}$), and comparing the effect of substitution relative to known deoxynojirimycin derivatives of the same (D-gluco, L-ido or D-galacto) configuration.

The present invention discloses D-gluco deoxynojirimycin derivatives and L-ido deoxynojirimycin derivatives, and D-deoxygalactonojirimycin derivatives, substituted with a non-fused bicyclic aromatic group, which is attached to the deoxynojirimycin or deoxygalactonojirimycin moiety through a linear methyloxypentyl group bearing various sidegroups, as defined above. The comparison of the inhibitory potency should be made within a given substituted D-deoxygalactonojirimycin or D-gluco- or L-ido deoxynojirimycin series, to allow appropriate comparison of the effect of the substituent. The substituent, in this context, is the group attached to the deoxynojirimycin or deoxygalactonojirimycin nitrogen atom, i.e. the substituent is a group comprising a linear methyloxypentyl group and a group X as defined above.

The $IC_{50}$ is a measure of the effectiveness of a substance in inhibiting a specific biological or biochemical function. Thus, the $IC_{50}$ of a compound for GCS inhibition is usually different the $IC_{50}$ of that compound for GBA1, GBA2 or intestinal glycosidase inhibition. Intestinal glycosidase inhibition is determined by determining the $IC_{50}$ for inhibition of sucrase (EC 3.2.1.48), lactase (EC 3.2.1.23) and/or maltase (EC. 3.2.1.20).

$IC_{50}$ values were determined by exposing cells or enzyme preparations to an appropriate range of deoxynojirimycin or deoxygalactonojirimycin derivatives at various concentrations, for various enzymes, as is explained in detail in Example 2.

In the following, the different contributions of the compounds of general structure I and Ia to the altering of the level of cytosolic or lysosomal glucosylceramide and/or higher glycosphingolipids will be discussed.

Increased Inhibitory Potency Towards GCS

In a first embodiment, compounds according to the present invention display increased inhibitory potency towards GCS, relative to known deoxynojirimycin derivatives of the same (D-gluco, L-ido or D-galacto) configuration. The inhibitory potency towards GCS of the compounds of the invention represented by general structure I or Ia, expressed as $IC_{50}$, is generally between 1 and 200 nM. In comparison, known adamantyl-substituted deoxynojirimycin derivatives 3 (D-gluco) and 4 (L-ido) have $IC_{50}$, values for GCS, measured in the same way, of 200 nM and 100 nM, respectively.

Preferably, compounds with increased inhibitory potency towards GCS are compounds of the general formula I or Ia, preferably I, defined above, wherein each of $R_{19}$ and $R_{20}$ is H, and wherein each of $R_{21}$-$R_{26}$ is independently selected from H, F, Me or Et;

$R_{27}$ and $R_{28}$ is independently selected from the group consisting of H, F, $CF_3$ and $C_1$-$C_8$ linear or branched alkyl;

X is

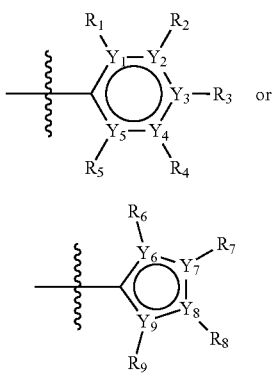

II

III wherein $Y_1$-$Y_5$ are C-atoms;

$Y_6$-$Y_9$ are independently selected from the group of C-, S-, N- and O-atoms and comprise at least one of an S-, N- or O-atom provided that $Y_6$-$Y_9$ comprises at most one S-atom, at most one N-atom and/or at most one O-atom, and provided that if one of $Y_6$-$Y_9$ is a S- or O-atom, the R-group attached to any S-, N- and/or O-atom is void, and provided that if none of $Y_6$-$Y_9$ is a S- or O-atom, the R-group attached to any N-atom is selected from the group consisting of H, $C_1$-$C_8$ linear or branched alkyl, IV and V, and provided that O and S-atoms are not concomitantly present;

one of $R_1$-$R_9$ is

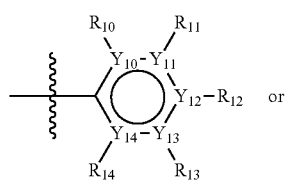

IV

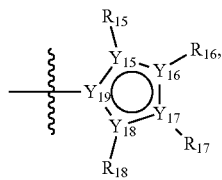

V and the remaining of $R_1$-$R_9$ are independently selected from the group consisting of H, F, Cl, Br, I, CN, $CF_3$, $C_1$-$C_8$ linear or branched alkyl and $C_1$-$C_8$ linear or branched oxyalkyl;

wherein $Y_{10}$-$Y_4$ are C-atoms;

$Y_{15}$-$Y_{18}$ are independently selected from the group of C-, S-, N- and O-atoms and $Y_{19}$ is selected from the group consisting of a C-atom and a N-atom, provided that $Y_{15}$-$Y_9$ comprises at most one S-atom, at most one N-atom and/or at most one O-atom, provided that if one of $Y_{15}$-$Y_{19}$ is a S- or O-atom, the group attached to any S-, N and/or O-atom is void, and provided that if none of $Y_{15}$-$Y_{19}$ is a S- or O-atom, the group attached to any N-atom is selected from the group consisting of H or $C_1$-$C_8$ linear or branched alkyl, and provided that O and S-atoms are not concomitantly present;

$R_{10}$-$R_{18}$ are independently selected from the group consisting of H, F, Cl, Br, I, CN, $CF_3$, $C_1$-$C_8$ linear or branched alkyl or $C_1$-$C_8$ linear or branched oxyalkyl, and/or wherein two of $R_{10}$-$R_{18}$ form a linear or branched fused alkylene or alkylenedioxy ring on two adjacent atoms of $Y_{10}$-$Y_{18}$;

or a pharmaceutically acceptable salt, ester, hydrate, and/or solvate thereof.

Compounds according to this definition have a inhibitory potency towards GCS of between 1 and 200 nM, preferably between 1 and 150 nM.

Alternatively preferred compounds of the present invention with increased inhibitory potency towards GCS are compounds according to general formula I or Ia, preferably I, defined above, wherein X is a biphenyl according to general structure VI, VII or VIII as in:

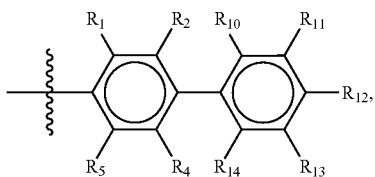

VI

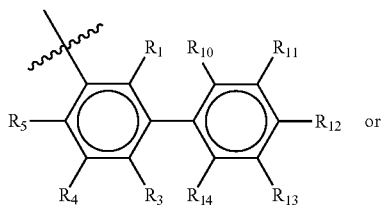

VII

-continued

VIII

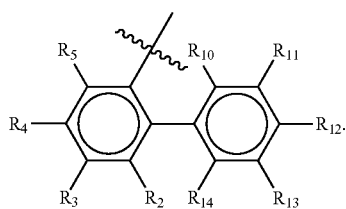

wherein each of the group consisting of $R_1$-$R_4$ are independently selected from the group consisting of H, F, Cl, Br, I, CN, $CF_3$, and $C_1$-$C_8$ linear or branched alkyl, and $R_{10}$-$R_{14}$ are independently selected from the group consisting of H, F, Cl, Br, I, CN, $CF_3$, and $C_1$-$C_8$ linear or branched alkyl and/or wherein two of the group consisting of $R_{10}$-$R_{14}$ form a linear or branched fused alkylene or alkylenedioxy ring on two adjacent atoms as defined in general terms above.

Among the biphenyls, biphenyls of general structure VI as defined above are particularly preferred.

More preferably, compounds displaying increased inhibitory potency towards GCS relative to known deoxynojirimycin derivatives of the same (D-gluco, L-ido, or D-galacto) configuration are compounds of general formula I or Ia, preferably I, wherein
  each of $R_{19}$ and $R_{20}$ is H, and wherein each of $R_{21}$-$R_{26}$ is independently selected from H, F, Me or Et;
  $R_{27}$ and $R_{28}$ is independently selected from the group consisting of H and $C_1$-$C_8$ linear or branched alkyl, preferably methyl;
  X is

II

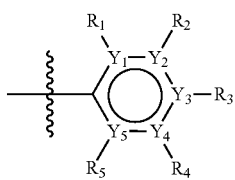

wherein
  $Y_1$-$Y_5$ are C-atoms;
  one of $R_1$-$R_5$ is

IV

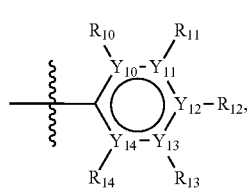

and the remaining of $R_1$-$R_9$ are independently selected from the group consisting of H, F, $CF_3$, $C_1$-$C_8$ linear or branched alkyl;
wherein
  $Y_{10}$-$Y_{14}$ are C-atoms;
  $R_{10}$-$R_{14}$ are independently selected from the group consisting of H, F, $CF_3$, $C_1$-$C_8$ linear or branched alkyl;
or a pharmaceutically acceptable salt, ester, hydrate, and/or solvate thereof.

Compounds according to this definition generally have an inhibitory potency towards GCS of 1-150 nM, preferably of 1-100 nM.

Further preferably, compounds displaying increased inhibitory potency towards GCS relative to known deoxynojirimycin derivatives of the same (D-gluco or L-ido) configuration are compounds of formula

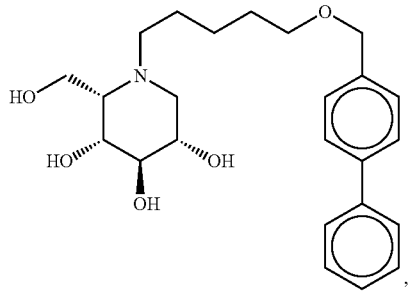

,

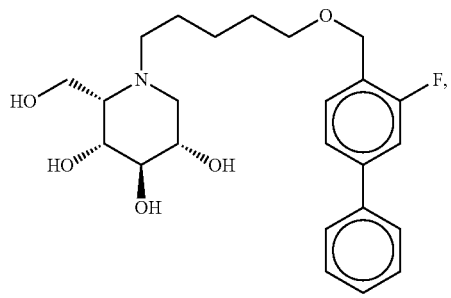

,

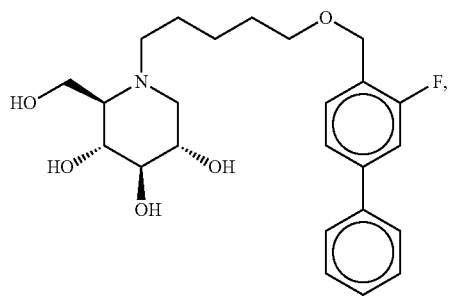

,

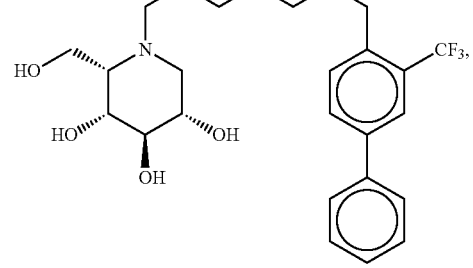

,

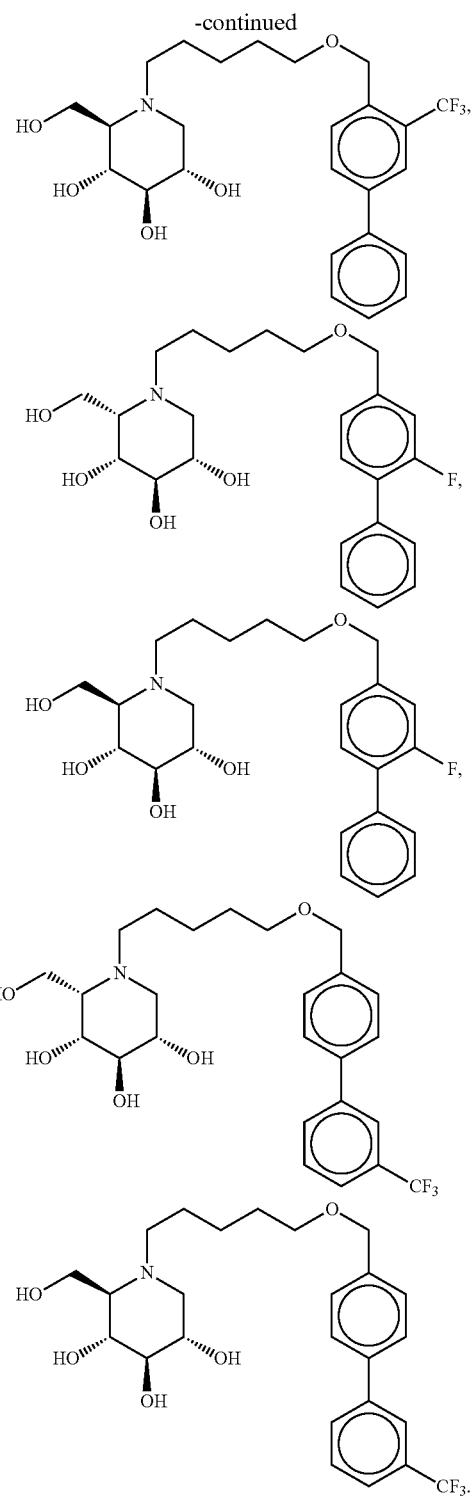

Compounds according to this definition generally have an inhibitory potency towards GCS of 1-100 nM, preferably 1-50 nM, more preferably 1-40 nM.

Most preferably, compounds displaying increased inhibitory potency towards known deoxynojirimycin derivatives of the same (D-gluco or L-ido) configuration are compounds of general formula I as in all definitions above wherein the sugar portion has the L-ido configuration, IX:

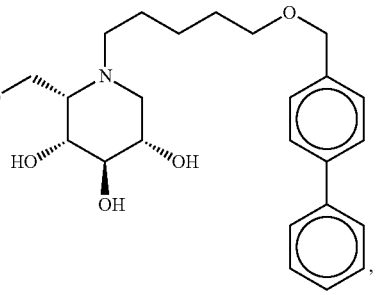

Deoxynojirimycin derivatives according to the present invention which have the L-ido configuration generally have an inhibitory potency towards GCS of 1-100 nM, preferably 1-50 nM, more preferably 1-40 nM, even more preferably 1-30 nM, even more preferably 1-10 nM, and most preferably 1-5 nM.

The preferred compounds displaying increased inhibitory potency towards GCS relative to known deoxynojirimycin derivatives of the same (D-gluco or L-ido) configuration are compounds with L-ido configuration of the structure

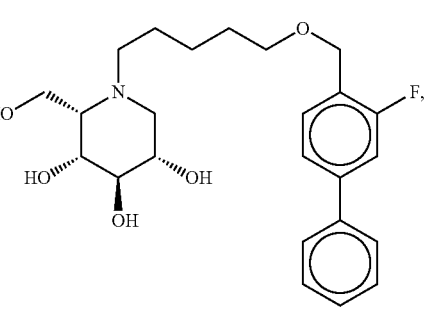

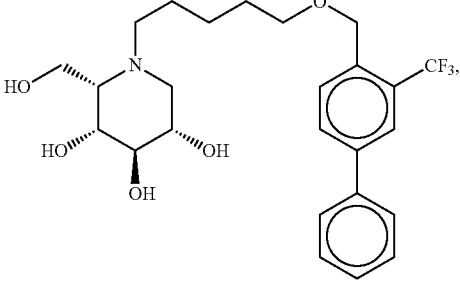

-continued

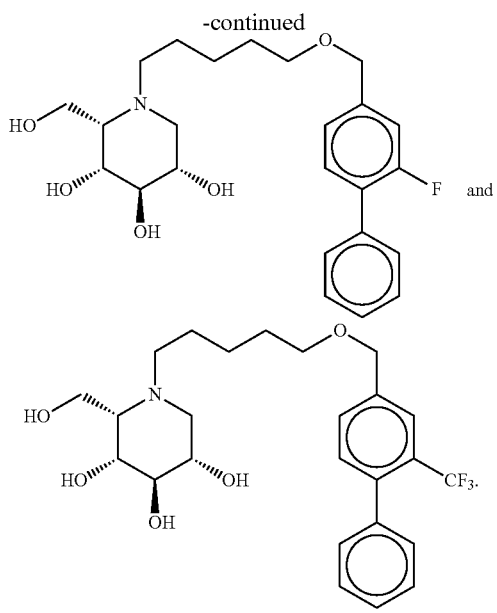

Compounds according to this definition generally have an inhibitory potency to GCS of 1-10 nM, preferably 1-5 nM.

Compounds displaying increased inhibitory potency towards GCS are beneficial in treating diseases in which the activity of GCS needs to be decreased. This is the case for diseases where either GCS-levels are increased and/or GCS activity is enhanced by excess presence of ceramide as substrate. Alternatively, such diseases are diseases where degradation of glucosylceramide is decreased, such as by a functional deficiency in GBA1 and/or in GBA2.

Therefore, compounds of the present invention which display increased inhibitory potency towards GCS are suitable for the treatment of diseases in groups 1-3 defined above, i.e. lysosomal storage disorders, among which Gaucher disease, Fabry disease, Tay-Sachs disease, Sandhoff disease, GM1 gangliosidosis, Sialidosis, Niemann Pick disease type C and AMRF ("Action Myoclonic Renal Failure Syndrome"), the symptoms of diseases collectively classed as metabolic syndrome, among which obesity, insulin resistance, hyperlipidemia, hypercholesterolemia, polycystic kidney disease and chronic inflammation, as well as treatment and/or prevention of diabetes type II, and neurodegenerative disorders, such as Parkinson disease and Lewy-body dementia. Preferably, these are Gaucher disease, Nieman-Pick disease type C and metabolic syndrome.

Inhibitory Potency Towards GBA2

In a second embodiment, the compounds of the present invention display an inhibitory potency towards GBA2, which provides a beneficial additional effect to improved GCS inhibition in certain diseases. The inhibitory potency towards GBA2 of the collection of compounds according to the present invention defined in generally formula I and Ia above, expressed as $IC_{50}$, is generally between 0.001 and 25 nM. In comparison, known adamantyl-substituted deoxynojirimycin derivatives 3 (D-gluco) and 4 (L-ido) have $IC_{50}$-values for GBA2, measured in the same way, of 2 nM and 1 nM, respectively, which allows for selecting compounds of the present invention with increased or decreased GBA2 inhibition in addition to increased GCS inhibition, as appropriate for the disease at issue.

Preferably, compounds of the present invention with inhibitory potency towards GBA2 are compounds of formula I or Ia, preferably I, above wherein:

each of $R_{19}$-$R_{26}$ is independently selected from H, F, Me or Et;

$R_{27}$ and $R_{28}$ is independently selected from the group consisting of H, F, $CF_3$ and $C_1$-$C_8$ linear or branched alkyl;

X is

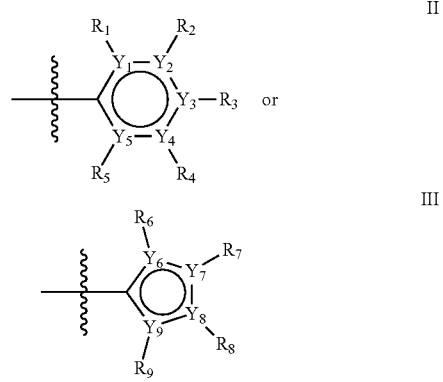

wherein $Y_1$-$Y_5$ are independently selected from the group of C and N-atoms provided that not more than one of $Y_1$-$Y_5$ is a N-atom, and provided that if one of $Y_1$-$Y_5$ is a N-atom, the R-group attached to that N-atom is void, and provided that at least one Y atom adjacent to that N-atom bears a group $R_n$=F;

$Y_6$-$Y_9$ are independently selected from the group of C-, S-, N- and O-atoms and comprise at least one of an S-, N- or O-atom provided that $Y_6$-$Y_9$ comprises at most one S-atom, at most one N-atom and/or at most one O-atom, and provided that if one of $Y_6$-$Y_9$ is a S- or O-atom, the R-group attached to any S-, N- and/or O-atom is void, and provided that if none of $Y_6$-$Y_9$ is a S- or O-atom, the R-group attached to any N-atom is selected from the group consisting of H, $C_1$-$C_8$ linear or branched alkyl, IV and V, and provided that O and S-atoms are not concomitantly present;

one of $R_1$-$R_9$ is

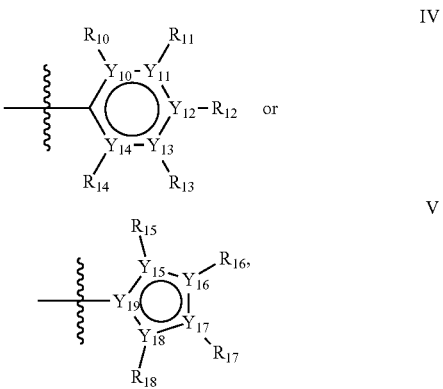

and the remaining of $R_1$-$R_9$ are independently selected from the group consisting of H, F, Cl, Br, I, CN, $CF_3$, $C_1$-$C_8$ linear or branched alkyl and $C_1$-$C_8$ linear or branched oxyalkyl;

wherein
- $Y_{10}$-$Y_{14}$ are independently selected from the group of C- and N-atoms provided that not more than one of $Y_1$-$Y_5$ is a N-atom, and provided that if one of $Y_1$-$Y_5$ is a N-atom, the R-group attached to that N-atom is void, and provided that at least one Y atom adjacent to that N-atom bears a group $R_n$=F;
- $Y_{15}$-$Y_{18}$ are independently selected from the group of C-, S-, N- and O-atoms and $Y_{19}$ is selected from the group consisting of a C-atom and a N-atom, provided that $Y_{15}$-$Y_{19}$ comprises at most one S-atom, at most one N-atom and/or at most one O-atom, provided that if one of $Y_{15}$-$Y_{19}$ is a S- or O-atom, the group attached to any S-, N and/or O-atom is void, and provided that if none of $Y_{15}$-$Y_{19}$ is a S- or O-atom, the group attached to any N-atom is selected from the group consisting of H or $C_1$-$C_8$ linear or branched alkyl, and provided that O and S-atoms are not concomitantly present;
- $R_{10}$-$R_{18}$ are independently selected from the group consisting of H, F, Cl, Br, I, CN, $CF_3$, $C_1$-$C_8$ linear or branched alkyl, provided that not more than one of $R_{10}$-$R_{18}$ is $CF_3$;

or a pharmaceutically acceptable salt, ester, hydrate, and/or solvate thereof.

Compounds according to this definition have an inhibitory potency towards GBA2 of generally 0.001-25 nM, preferably 0.001-10 nM.

Further preferably, compounds of the present invention with inhibitory potency towards GBA2 are compounds according to general formula I or Ia, preferably I, defined above, wherein X is a biphenyl according to general structure VI, VII or VIII as in:

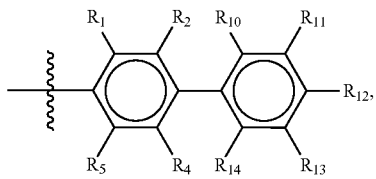
VI

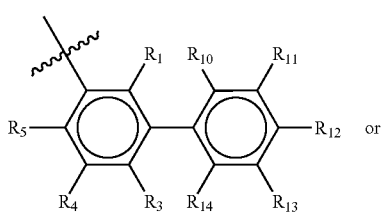
VII

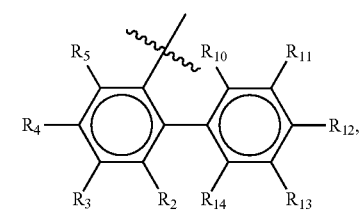
VIII wherein each of the group consisting of $R_1$-$R_4$ are independently selected from the group consisting of H, F, Cl, Br, I, CN, $CF_3$, and $C_1$-$C_8$ linear or branched alkyl, and $R_{10}$-$R_{14}$ are independently selected from the group consisting of H, F, Cl, Br, I, CN, $CF_3$, and $C_1$-$C_8$ linear or branched alkyl and/or wherein two of the group consisting of $R_{10}$-$R_{14}$ form a linear or branched fused alkylene or alkylenedioxy ring on two adjacent atoms as defined in general terms above.

More preferably, compounds that display inhibitory potency towards GBA2 are compounds of general formula I or Ia, preferably I, above wherein:
- each of $R_{19}$-$R_{26}$ is H;
- $R_{27}$ and $R_{28}$ is independently selected from the group consisting of H and $C_1$-$C_8$ linear or branched alkyl, preferably methyl;
- X is

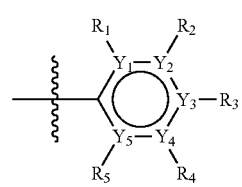
II wherein
each of $Y_1$-$Y_5$ is a C-atom;
$R_3$ is

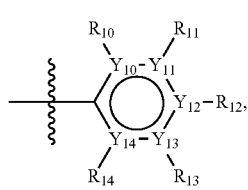
IV and the remaining of $R_1$-$R_5$ are independently selected from the group consisting of H, F and $CF_3$;
wherein
each of $Y_{10}$-$Y_{14}$ is a C-atom;
$R_{10}$, $R_{11}$, $R_{13}$ and $R_{14}$ are H, and $R_{12}$ is H or F;
or a pharmaceutically acceptable salt, ester, hydrate, and/or solvate thereof.

Compounds according to this definition generally have an inhibitory potency towards GBA2 of 0.001-10 nM, preferably 0.001-5 nM, more preferably 0.001-2 nM, and most preferably in the sub-nanomolar range such as 0.001-1 nM.

Most preferably, compounds according to the present invention display increased inhibitory potency towards GBA2 relative to known deoxynojirimycin derivatives of the same configuration, which are compounds of general formula I as variously defined above wherein the sugar portion has the D-gluco configuration, XI:

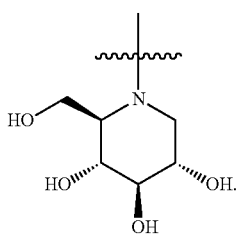
XI

Deoxynojirimycin derivatives according to the present invention which have the D-gluco configuration generally have an inhibitory potency towards GBA2 of 0.001-5 nM, preferably 0.001-1 nM, more preferably 0.001-0.7 nM.

The preferred compounds displaying increased inhibitory potency towards GBA2 relative to known deoxynojirimycin derivatives of the same (D-gluco) configuration are Alternatively, highly preferred compounds of general structure Ia displaying increased inhibitory potency towards GBA2 are

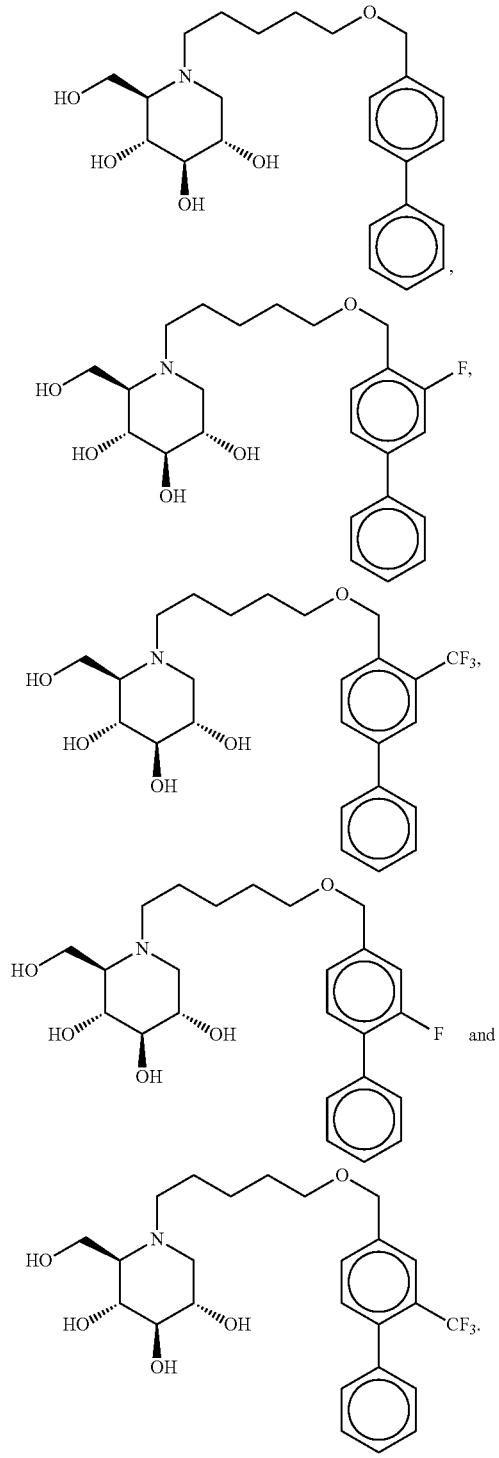

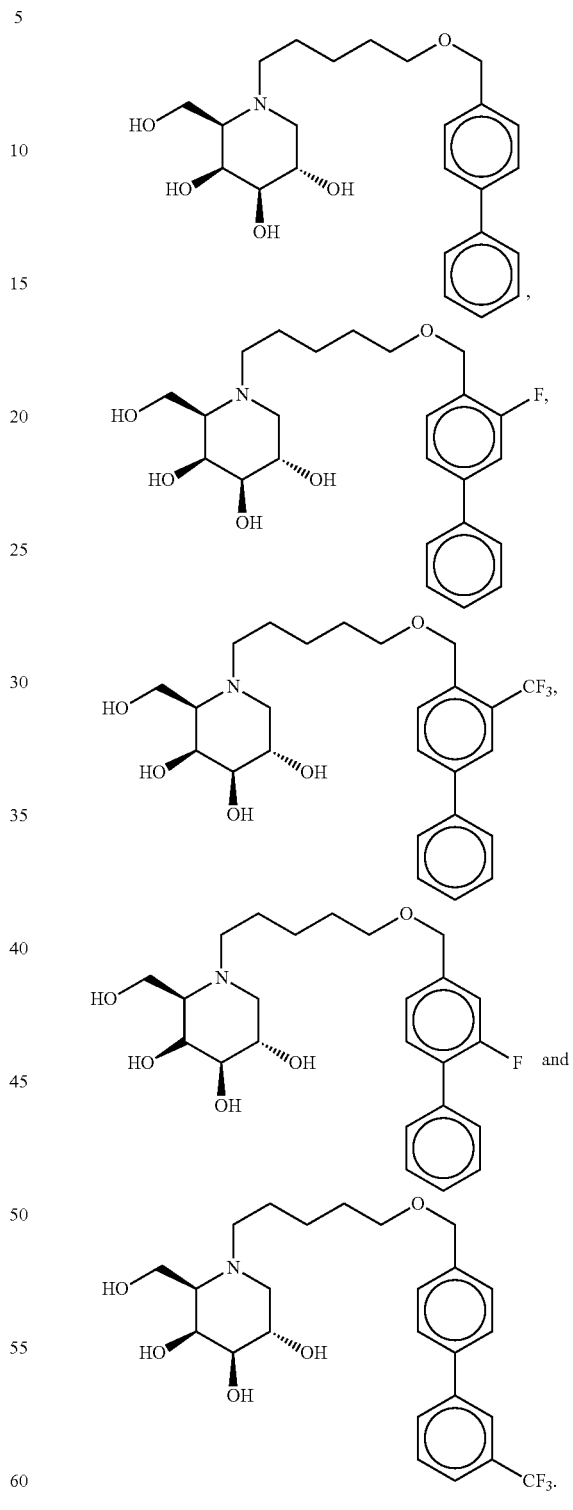

Compounds according to this definition generally have an inhibitory potency to GBA2 of 0.001-1 nM, preferably 0.001-0.7 nM.

Compounds displaying inhibitory potency towards GBA2 in addition to displaying inhibitory potency to GCS are beneficial in treating diseases in which the activity of both GBA2 and GCS needs to be decreased. These are lysosomal storage disorders with the exception of Fabry disease, i.e.

Gaucher disease, Tay-Sachs disease, Sandhoff disease, GM1 gangliosidosis, Sialidosis, Niemann Pick disease type C and AMRF ("Action Myoclonic Renal Failure Syndrome") and neurodenegerative disorders, such as Parkinson disease and Lewy-body dementia. Preferably, these are Gaucher disease and Niemann-Pick disease type C.

Inhibitory Potency Towards GBA1

In a third embodiment, the compounds of the present invention display variable inhibitory potency towards GBA1, relative to known deoxynojirimycin derivatives of the same (D-gluco, L-ido or D-galacto) configuration. The inhibitory potency towards GBA1 of the compounds according to the present invention defined in generally formula I or Ia above, expressed as $IC_{50}$, is generally between 50 and 100.000 nM, preferably between 70 and 60000 nM, more preferably between 70 and 50000 nM. In comparison, the $IC_{50}$ of adamantyl-substituted deoxynojirimycin derivatives 3 (D-gluco) and 4 (L-ido) are 100 nM and 2000 nM, respectively.

Preferably, compounds of the present invention with variable inhibitory potency towards GBA1 relative to known deoxynojirimycin derivatives of the same (D-gluco, L-ido or D-galacto) configuration are compounds of formula I or Ia, preferably I, above wherein:

each of $R_{19}$-$R_{26}$ is independently selected from H, F, Me or Et;

$R_{27}$ and $R_{28}$ is independently selected from the group consisting of H, F, $CF_3$ and $C_1$-$C_8$ linear or branched alkyl;

X is

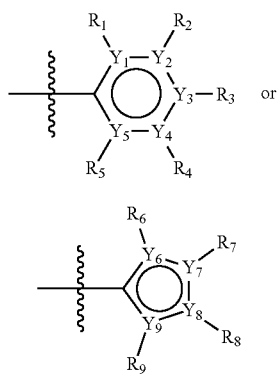

wherein $Y_1$-$Y_5$ are independently selected from the group of C and N-atoms provided that not more than two of $Y_1$-$Y_5$ are a N-atom, and provided that if one or two of $Y_1$-$Y_5$ is a N-atom, the R-group attached to that N-atom is void;

$Y_6$-$Y_9$ are independently selected from the group of C-, S-, N- and O-atoms and comprise at least one of an S-, N- or O-atom provided that $Y_6$-$Y_9$ comprises at most one S-atom, at most one N-atom and/or at most one O-atom, and provided that if one of $Y_6$-$Y_9$ is a S- or O-atom, the R-group attached to any S-, N- and/or O-atom is void, and provided that if none of $Y_6$-$Y_9$ is a S- or O-atom, the R-group attached to any N-atom is selected from the group consisting of H, $C_1$-$C_8$ linear or branched alkyl, IV and V, and provided that O and S-atoms are not concomitantly present;

one of $R_1$-$R_9$ is

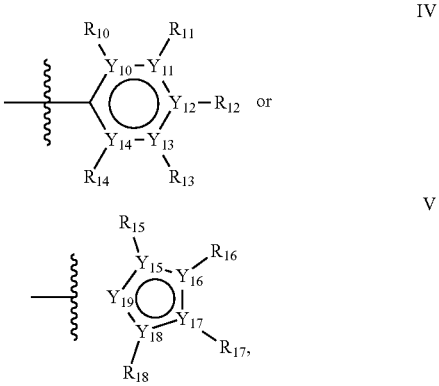

and the remaining of $R_1$-$R_9$ are independently selected from the group consisting of H, F, Cl, Br, I, CN, $CF_3$, $C_1$-$C_8$ linear or branched alkyl and $C_1$-$C_8$ linear or branched oxyalkyl;

wherein $Y_{10}$-$Y_{14}$ are independently selected from the group of C- and N-atoms provided that not more than two of $Y_{10}$-$Y_{14}$ are a N-atom, and provided that if one or two of $Y_{10}$-$Y_{14}$ is a N-atom, the R-group attached to that N-atom is void;

$Y_{15}$-$Y_{18}$ are independently selected from the group of C-, S-, N- and O-atoms and $Y_{19}$ is selected from the group consisting of a C-atom and a N-atom, provided that $Y_{15}$-$Y_{19}$ comprises at most one S-atom, at most one N-atom and/or at most one O-atom, provided that if one of $Y_{15}$-$Y_{19}$ is a S- or O-atom, the group attached to any S-, N and/or O-atom is void, and provided that if none of $Y_{16}$-$Y_{19}$ is a S- or O-atom, the group attached to any N-atom is selected from the group consisting of H or $C_1$-$C_8$ linear or branched alkyl, and provided that O and S-atoms are not concomitantly present;

$R_{10}$-$R_{18}$ are independently selected from the group consisting of H, F, Cl, Br, I, CN, $CF_3$, $C_1$-$C_8$ linear or branched oxyalkyl, and/or wherein two of $R_{10}$-$R_{18}$ form a linear or branched fused alkylene or alkylenedioxy ring on two adjacent atoms of $Y_{10}$-$Y_{18}$;

or a pharmaceutically acceptable salt, ester, hydrate, and/or solvate thereof.

Generally, compounds according to this definition have an inhibitory potency towards GBA1 of more than 100 nM, preferably more than 500 nM, more preferably more than 1000 nM, even more preferably more than 5000 nM, and most preferably more than 10000 nM.

More preferably, compounds of the present invention with variable inhibitory potency towards GBA1 relative to known deoxynojirimycin derivatives of the same (D-gluco, L-ido or D-galacto) configuration are compounds of formula I or Ia, preferably I, above wherein:

each of $R_{10}$-$R_{26}$ is independently selected from H, F, Me or Et;

$R_{27}$ and $R_{28}$ is independently selected from the group consisting of H, F, $CF_3$ and $C_1$-$C_8$ linear or branched alkyl;

X is

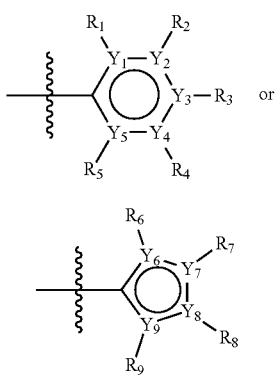

or

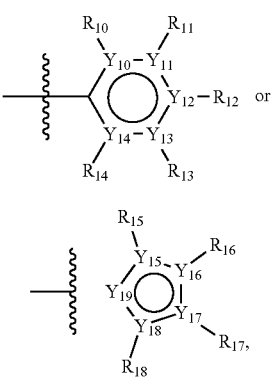

wherein
Y$_1$-Y$_5$ are independently selected from the group of C and N-atoms provided that not more than two of Y$_1$-Y$_5$ are a N-atom, and provided that if one or two of Y$_1$-Y$_5$ is a N-atom, the R-group attached to that N-atom is void;

Y$_6$-Y$_9$ are independently selected from the group of C-, S-, N- and O-atoms and comprise at least one of an S-, N- or O-atom provided that Y$_6$-Y$_9$ comprises at most one S-atom, at most one N-atom and/or at most one O-atom, and provided that if one of Y$_6$-Y$_9$ is a S- or O-atom, the R-group attached to any S-, N- and/or O-atom is void, and provided that if none of Y$_6$-Y$_9$ is a S- or O-atom, the R-group attached to any N-atom is selected from the group consisting of H, C$_1$-C$_8$ linear or branched alkyl, IV and V, and provided that O and S-atoms are not concomitantly present;

one of the group consisting of R$_1$, R$_3$, R$_5$, R$_6$, R$_7$, R$_8$ and R$_9$ is

IV $$\begin{array}{c} R_{10} \quad R_{11} \\ Y_{10}-Y_{11} \\ Y_{12}-R_{12} \\ Y_{14}-Y_{13} \\ R_{14} \quad R_{13} \end{array}$$

or

V $$\begin{array}{c} R_{15} \\ Y_{15}-Y_{16} \\ Y_{19} \quad Y_{17} \\ Y_{18} \\ R_{18} \quad R_{17}, \end{array}$$

and the remaining of R$_1$-R$_9$ are independently selected from the group consisting of H, F, Cl, Br, I, CN, CF$_3$, C$_1$-C$_8$ linear or branched alkyl and C$_1$-C$_8$ linear or branched oxyalkyl;

wherein
Y$_{10}$-Y$_{14}$ are independently selected from the group of C- and N-atoms provided that not more than two of Y$_{10}$-Y$_{14}$ are a N-atom, and provided that if one or two of Y$_{10}$-Y$_{14}$ is a N-atom, the R-group attached to that N-atom is void;

Y$_{15}$-Y$_{18}$ are independently selected from the group of C-, S-, N- and O-atoms and Y$_{19}$ is selected from the group consisting of a C-atom and a N-atom, provided that Y$_5$-Y$_{19}$ comprises at most one S-atom, at most one N-atom and/or at most one O-atom, provided that if one of Y$_{15}$-Y$_{19}$ is a S- or O-atom, the group attached to any S-, N and/or O-atom is void, and provided that if none of Y$_{15}$-Y$_{19}$ is a S- or O-atom, the group attached to any N-atom is selected from the group consisting of H or C$_1$-C$_8$ linear or branched alkyl, and provided that O and S-atoms are not concomitantly present;

R$_{10}$-R$_{18}$ are independently selected from the group consisting of H, C$_1$-C$_8$ linear or branched oxyalkyl, and/or wherein two of R$_{10}$-R$_{18}$ form a linear or branched fused alkylene or alkylenedioxy ring on two adjacent atoms of Y$_{10}$-Y$_{18}$;

or a pharmaceutically acceptable salt, ester, hydrate, and/or solvate thereof.

Compounds of this definition generally have an inhibitory potency towards GBA1 of more than 500 nM, preferably more than 1000 nM. The inhibitory potency towards GBA1 will generally not be higher than 50.000 nM, preferably 75.000 nM, more preferably 100.000 nM.

Preferred compounds of the present invention with variable inhibitory potency towards GBA1 are compounds according to general formula I or Ia, preferably I, defined above, wherein X is a biphenyl according to general structures VI, VII or VIII as in:

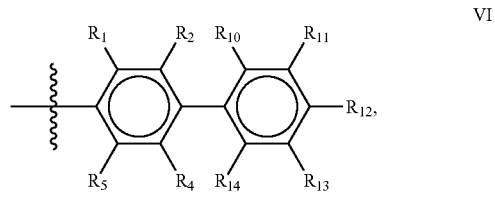

VI

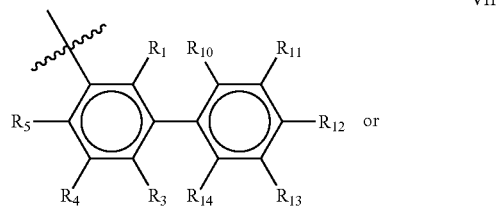

VII or

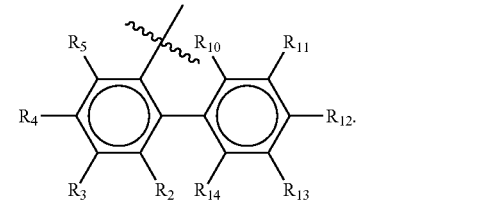

VIII wherein each of the group consisting of R$_1$-R$_4$ are independently selected from the group consisting of H, F, Cl, Br, I, CN, CF$_3$, and C$_1$-C$_8$ linear or branched alkyl, and R$_{10}$-R$_{14}$ are independently selected from the group consisting of H, F, Cl, Br, I, CN, CF$_3$, and C$_1$-C$_8$ linear or branched alkyl and/or wherein two of the group consisting of R$_{10}$-R$_{14}$ form a linear or branched fused alkylene or alkylenedioxy ring on two adjacent atoms.

In one alternative, compounds of the present invention with decreased inhibitory potency towards GBA1 are compounds according to general structure I or Ia, preferably I, defined above, wherein X is a biphenyl according to general structure VI or VIII as in:

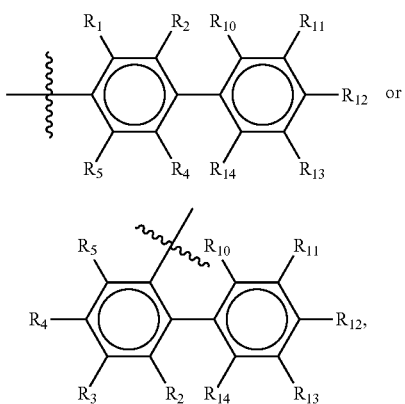

VI

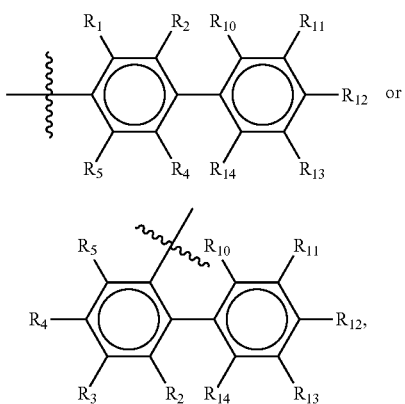

VIII wherein each of the group consisting of $R_1$-$R_4$ are independently selected from the group consisting of H, F, Cl, Br, I, CN, $CF_3$, and $C_1$-$C_8$ linear or branched alkyl, and $R_{10}$-$R_{14}$ are independently selected from the group of H and $C_1$-$C_8$ linear or branched oxyalkyl, and/or wherein two of the group consisting of $R_{10}$-$R_{14}$ form a linear or branched fused alkylene or alkylenedioxy ring on two adjacent atoms as defined in general terms above.

Most preferred among the biphenyls are a group X of general structure VI.

More preferably, compounds according to the present invention displaying decreased inhibitory potency towards GBA1 relative to known deoxynojirimycin derivatives of the same (L-ido) configuration are compounds of general formula I as variously defined above wherein the sugar portion has the L-ido configuration, IX

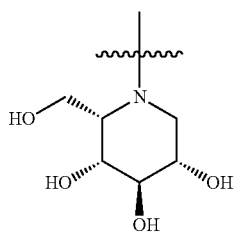

IX

Compounds according to this definition generally have an inhibitory potency towards GBA1 of more than 3000 nM, preferably more than 5000 nM, more preferably more than 10.000 nM.

Most preferred compounds displaying decreased inhibitory potency towards GBA1 relative to known deoxynojirimycin derivatives of the same (D-gluco or L-ido) configuration are compounds of general structure I defined above, wherein Deoxynojirimycin is of the L-ido configuration IX

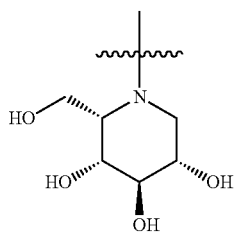

IX each of $R_{19}$-$R_{26}$ is independently selected from H, F, Me or Et;

$R_{27}$ and $R_{28}$ is independently selected from the group consisting of H, F, $CF_3$ and $C_1$-$C_8$ linear or branched alkyl;

X is

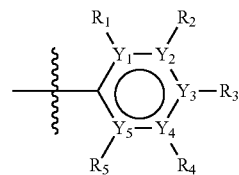

II wherein $Y_1$-$Y_5$ are all C-atoms;

one of $R_1$-$R_9$ is

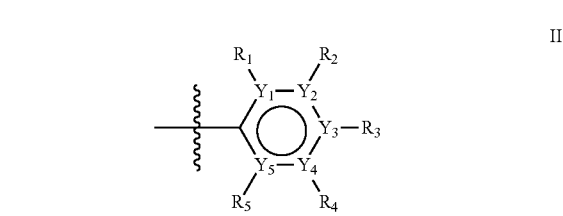

IV and the remaining of $R_1$-$R_9$ are independently selected from the group consisting of H, F, Cl, Br, I, CN, $CF_3$, $C_1$-$C_8$ linear or branched alkyl and $C_1$-$C_8$ linear or branched oxyalkyl;

wherein $Y_{10}$-$Y_{14}$ are all C-atoms;

$R_{10}$-$R_{14}$ are independently selected from the group consisting of H, F, Cl, Br, CN, $CF_3$, $C_1$-$C_8$ linear or branched oxyalkyl, and/or wherein two of $R_{10}$-$R_{18}$ form a linear or branched fused alkylene or alkylenedioxy ring on two adjacent atoms of $Y_{10}$-$Y_{14}$;

or a pharmaceutically acceptable salt, ester, hydrate, and/or solvate thereof.

Alternatively, preferred compounds displaying decreased inhibitory potency towards GBA1 are compounds of general structure Ia defined above, wherein each of $R_{19}$-$R_{26}$ is independently selected from H, F, Me or Et;

$R_{27}$ and $R_{28}$ is independently selected from the group consisting of H, F, $CF_3$ and $C_1$-$C_8$ linear or branched alkyl;

X is

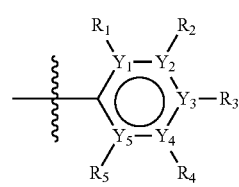

II wherein
Y$_1$-Y$_5$ are all C-atoms;
one of R$_1$-R$_9$ is

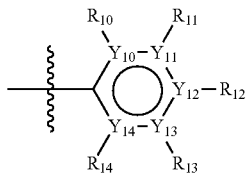

IV and the remaining of R$_1$-R$_9$ are independently selected from the group consisting of H, F, Cl, Br, I, CN, CF$_3$, C$_1$-C$_8$ linear or branched alkyl and C$_1$-C$_8$ linear or branched oxyalkyl;
wherein
Y$_{10}$-Y$_{14}$ are all C-atoms;
R$_{10}$-R$_{14}$ are independently selected from the group consisting of H, F, Cl, Br, CN, CF$_3$, C$_1$-C$_8$ linear or branched oxyalkyl, and/or wherein two of R$_{10}$-R$_{18}$ form a linear or branched fused alkylene or alkylenedioxy ring on two adjacent atoms of Y$_{10}$-Y$_{14}$;
or a pharmaceutically acceptable salt, ester, hydrate, and/or solvate thereof.

Generally, compounds according to this definition have an inhibitory potency towards GBA1 of more than 3000 nM, preferably more than 5000 nM, more preferably more than 10.000 nM.

Compounds displaying decreased inhibitory potency towards GBA1 are beneficial in treating diseases in which GBA1 should retain its natural function as much as possible. Generally, this means that the compounds of the present invention do not significantly affect the functioning of GBA1, although the compounds of the present invention may have an inhibitory effect on other enzymes, which may be beneficial in the treatment of certain diseases (vide supra). In diseases where inhibition of GBA1 negatively affects treatments, for instance by inducing side-effects, or by further decreasing an already impaired glucosylceramide degradation pathway, but where inhibition of other enzymes may aid in restoring an irregular level of cytosolic or lysosomal glucosylceramide, supplementation of the compounds of the present invention results in a more effective treatment. A particularly preferred disease where this is the case is Gaucher disease and Parkinson.

Alternatively, compounds with moderately to high inhibitory potency towards GBA1 according to the present invention may be suitably applied, also. Generally, such compounds have an inhibitory potency of 10-400 nM, preferably 10-200 nM. Such compounds are preferably compounds of general structure I defined above, wherein the deoxynojirimycin derivative is of the D-gluco configuration,

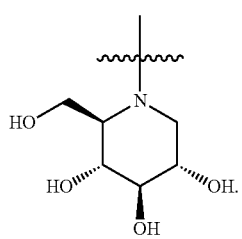

XI

More preferably, compounds with moderately to high inhibitory potency towards GBA1 are of general structure I wherein the deoxynojirimycin derivative is of the D-gluco configuration

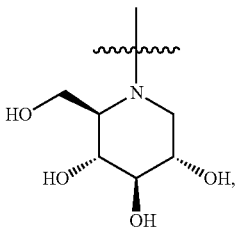

XI and wherein X=

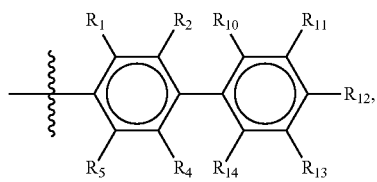

VI

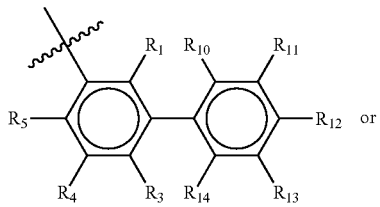

VII

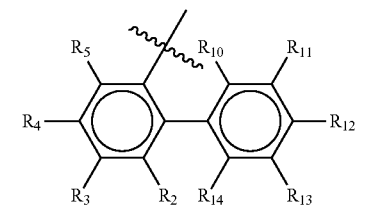

VIII wherein each of the group consisting of R$_1$-R$_4$ are independently selected from the group consisting of H, F, Cl, Br, I, CN, CF$_3$, and C$_1$-C$_8$ linear or branched alkyl, and R$_{10}$-R$_{14}$ are independently selected from the group consisting of H, F, Cl, Br, I, CN, CF$_3$, and C$_1$-C$_8$ linear or branched alkyl and/or wherein two of the group consisting of R$_{10}$-R$_{14}$ form a linear or branched fused alkylene or alkylenedioxy ring on two adjacent atoms.

Compounds according to this definition generally have an inhibitory potency towards GBA1 of 10-10000 mM, preferably 10-3000 nM, more preferably 10-1000 nM.

Intestinal Glycosidase Inhibition

A second advantage of deoxynojirimycin derivatives and deoxygalactonojirimycin derivatives according to the present invention is that their inhibitory potency towards intestinal glycosidases is low, relative to known deoxynojirimycin derivatives of the same (D-gluco, L-ido or D-galacto) configuration. Inhibition of intestinal glycosidases is associated with the occurrence of adverse side-effects during therapeutic supplementation of deoxynojirimycin derivatives (see for instance Wennekes T, van den Berg R J, Boot R G, van der Marel G A, Overkleeft H S, Aerts J M. Glycosphingolipids—nature, function, and pharmacological modulation. Angew Chem Int Ed Engl. 2009; 48(47):8848-69. doi: 10.1002/anie.200902620).

In particular, deoxynojirimycin derivatives of the L-ido-configuration substituted with an aromatic group have little inhibitory potency towards the intestinal glycosidases. The inhibitory potency of deoxynojirimycin derivatives of the L-ido configuration for intestinal glycosidases is generally above 1 µM.

Reduction of inhibition of intestinal glycosidases is desirable for any disease mentioned above since it will improve compliance due to absence of intestinal discomfort.

Effects on Glucosylceramide Levels

The combined effect of the compounds of the present invention on the activity of GCS, GBA1 and/or GBA2 can be applied to treat diseases which are characterized by an irregular level of cytosolic or lysosomal glucosylceramide and/or higher glycosphingolipids. Compounds of the present invention can be selected to treat an appropriate disease, based on the required level of inhibitory potency towards the GCS, GBA1 and/or GBA2.

Selection of the compounds defined above with increased inhibitory potency towards GCA and/or GBA2, and/or with decreased inhibitory potency towards GBA1 and/or intestinal glycosidases, relative to known deoxynojirimycin derivatives of the same (D-gluco, L-ido or D-galacto) configuration is done by selecting compounds with an appropriate $IC_{50}$ for GCS, GBA2, GBA1 and/or intestinal glycosidases as defined above. Selected compounds can then be applied therapeutically in a treatment of a disease for which the $IC_{50}$ values are appropriate.

Therapeutic Application in Lysosomal Storage Disorders

In one embodiment, compounds of the present invention are applied in the treatment of lysosomal storage disorders, such as Gaucher disease, Fabry disease, Sandhoff disease, Tay-Sach disease, GM1 gangliosidosis, sialidosis, Sialidosis, AMFR or Niemann Pick type C disease, preferably Gaucher disease and Niemann-Pick disease type C.

The lysosomal storage disorders GM1 Gangliosidosis, Tay-Sach disease, Sialidosis, Sandhoff disease and Fabry disease are characterised by accumulation of higher glycosphingolipids in the lysosome, and are therefore suitably treated by compounds of the present invention by inhibition of formation of glucosylceramide by GCS. The lysosomal storage disorders Gaucher disease and Niemann-Pick disease type C are associated with defects in the enzyme GBA1, and display accumulation of the glycosphingolipid glucosylceramide in the lysosome. Pharmacological inhibition of GCS by the compounds of the present invention prevents lysosomal accumulation of glucosylceramide and/or the higher glycosphingolipids, and is therefore also suitable in the treatment of Gaucher disease and Niemann-Pick disease type C.

Preferred compounds according to the present invention in the treatment of lysosomal storage disorders are compounds which display high inhibitory potency towards GCS, as defined above. Therefore, all compounds of general structure I and Ia, preferably I, are suitable to treat lysosomal storage disorders.

Preferably, in the treatment of lysosomal storage disorders, GBA1 should be affected as little as possible, to retain the natural lysosomal glucosylceramide degradation as much as possible, which means that GBA1 should be inhibited as little as possible. The different inhibitory potency toward GCS and toward GBA1 of compounds according to the present invention results in an attractive therapeutic window, in which high GCS inhibitory potency is combined with low GBA1 inhibitory potency. The GCS/GBA1 therapeutic window is distinctly improved for the compounds of the present invention. The skilled person can, based on the above, select suitable compounds according to the present invention which have higher inhibitory potency toward GCS than known deoxynojirimycin derivatives, and which also display low inhibitory potency toward GBA1, and these combinations should be considered part of the present invention.

Further preferably, it is generally acknowledged that inhibition of GBA2 is beneficial in the treatment of neuronopathic lysosomal storage disorders. Compounds with a higher inhibitory potency towards GBA2, relative to known deoxynojirimycin derivatives of the same configuration, are therefore preferably selected.

The skilled person can, based on the above, select suitable compounds according to the present invention which have higher inhibitory potency toward GCS than known deoxynojirimycin derivatives, and which also display higher inhibitory potency toward CBA2 than known deoxynojirimycin derivatives, and the selected compounds should be considered part of the invention.

Much preferred in the treatment of lysosomal storage disorders is selection of compounds which have a low inhibitory potency towards GBA1, and a higher inhibitory potency toward both GCS and CBA2. Application of such compounds in the treatment of lysosomal storage disorders results in increased therapeutic effectiveness and with less side effects, relative to application of known deoxynojirimycin derivatives.

In lysosomal storage disorders, such as Gaucher disease, AMRF, Fabry disease, Sandhoff disease, Tay-Sach disease, GM1 gangliosidosis, Sialidosis or Niemann Pick type C disease, the inhibitory potency towards GBA1 is preferably low. For this reason, preferred compounds in the treatment of neuronopathic lysosomal storage disorders are compounds of general formula I as variously defined above, wherein the deoxynojirimycin derivative has the L-ido configuration IX

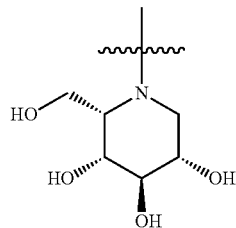

IX

Preferably for such diseases, the inhibitory potency towards both GCS and GBA2 is high, whereas the inhibitory potency towards GBA1 is low.

Alternatively, compounds according to general structure Ia, having a D-galacto-configuration, are much preferred in this respect.

Preferably, compounds according to the present invention in the treatment of lysosomal storage disorders are compounds of general structure I, wherein Deoxynojirimycin is of the L-ido configuration IX

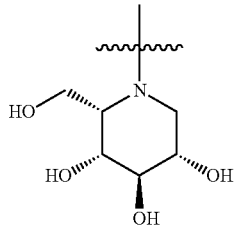

IX each of $R_{19}$-$R_{26}$ is independently selected from H, F, Me or Et;

$R_{27}$ and $R_{28}$ is independently selected from the group consisting of H, F, $CF_3$ and $C_1$-$C_8$ linear or branched alkyl;

X is

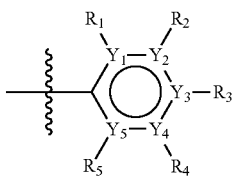

II wherein $Y_1$-$Y_5$ are all C-atoms;

one of $R_1$-$R_5$ is

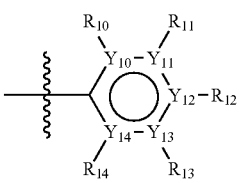

IV and the remaining of $R_1$-$R_5$ are independently selected from the group consisting of H, F, Cl, Br, I, CN, $CF_3$, $C_1$-$C_8$ linear or branched alkyl and $C_1$-$C_8$ linear or branched oxyalkyl;

wherein $Y_{10}$-$Y_{14}$ are all C-atoms;

$R_{10}$-$R_{14}$ are independently selected from the group consisting of H, F, Cl, Br, CN, $CF_3$, $C_1$-$C_8$ linear or branched oxyalkyl, and/or wherein two of $R_{10}$-$R_{18}$ form a linear or branched fused alkylene or alkylenedioxy ring on two adjacent atoms of $Y_{10}$-$Y_{14}$;

or a pharmaceutically acceptable salt, ester, hydrate, and/or solvate thereof.

Similarly preferred compounds are compounds of general structure I or Ia, preferably I, in which X is a biphenyl according to general structure VI, VII or VIII as in:

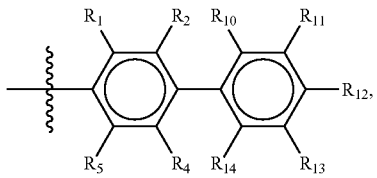

VI

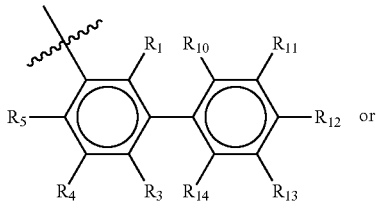

VII

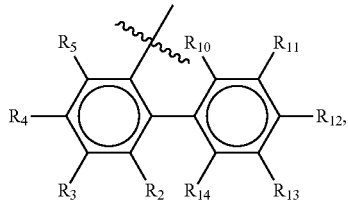

VIII wherein each of the group consisting of $R_1$-$R_4$ are independently selected from the group consisting of H, F, Cl, Br, I, CN, $CF_3$, and $C_1$-$C_8$ linear or branched alkyl, and $R_{10}$-$R_{14}$ are independently selected from the group consisting of H, F, Cl, Br, I, CN, $CF_3$, and $C_1$-$C_8$ linear or branched alkyl and/or wherein two of the group consisting of $R_{10}$-$R_{14}$ form a linear or branched fused alkylene or alkylenedioxy ring on two adjacent atoms as defined in general terms above.

Among the biphenyls, compounds of general structure VI with $R_1$-$R_{14}$=H, F of $CF_3$ are particularly preferred. Particularly preferred compounds for the treatment of lysosomal storage disorders are

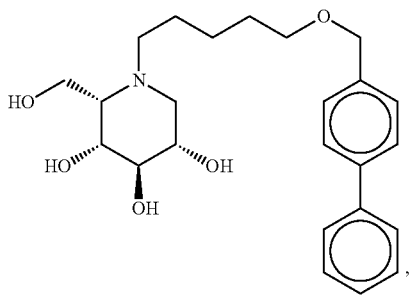

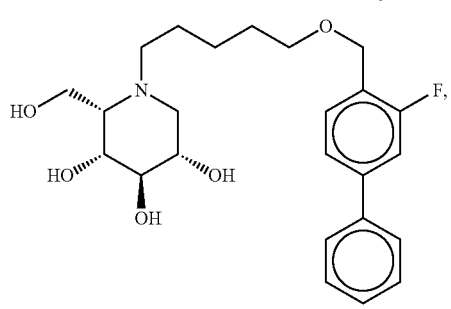

-continued

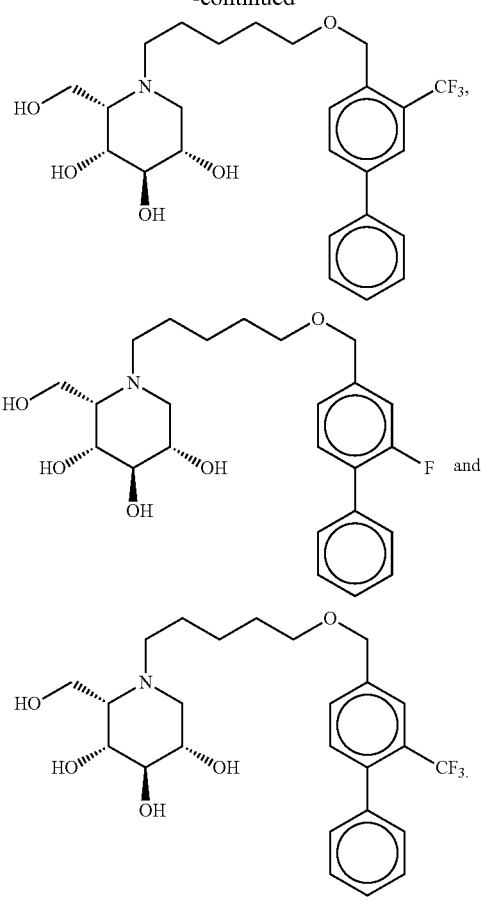

Therapeutic Application in Metabolic Syndrome

In another embodiment, the compounds of the present invention are applied in the treatment of symptoms of metabolic syndrome, including type II diabetes. Type II diabetes is a disease characterized by insulin resistance. Excessive presence of glycosphingolipids in cells is associated with reduced sensitivity to insulin. Of note, other aspects of metabolic syndrome such as hyperlipidemia, hypercholesterolemia, fatty liver (hepatosteatosis) are also ameliorated by reduction of excessive glycosphingolipids through inhibition of GCS.

Type II diabetes and the other symptoms characteristic for Metabolic Syndrome can therefore effectively be treated by therapeutic application of compounds according to the present invention which display high inhibitory potency towards GCS, as defined above. Preferably, compounds according to the present invention also display high inhibitory potency of the intestinal glycosidases.

Further preferably, compounds of the present invention for the treatment of symptoms of metabolic syndrome display little inhibitory potency for GBA1. The potency for GBA2 is irrelevant for the treatment of symptoms of metabolic syndrome.

Therefore, preferred compounds according to the present invention for the treatment of symptoms of metabolic syndrome display are compounds according to general formula I defined above, wherein Deoxynojirimycin is of the L-ido configuration IX

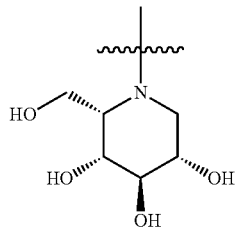

IX each of $R_{19}$-$R_{26}$ is independently selected from H, F, Me or Et;

$R_{27}$ and $R_{28}$ is independently selected from the group consisting of H, F, $CF_3$ and $C_1$-$C_8$ linear or branched alkyl;

X is

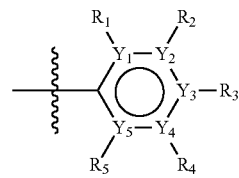

II wherein $Y_1$-$Y_5$ are all C-atoms;

one of $R_1$-$R_5$ is

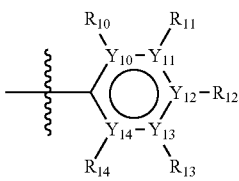

IV and the remaining of $R_1$-$R_5$ are independently selected from the group consisting of H, F, Cl, Br, I, CN, $CF_3$, $C_1$-$C_8$ linear or branched alkyl and $C_1$-$C_8$ linear or branched oxyalkyl;

wherein $Y_{10}$-$Y_{14}$ are all C-atoms;

$R_{10}$-$R_{14}$ are independently selected from the group consisting of H, F, Cl, Br, CN, $CF_3$, $C_1$-$C_8$ linear or branched oxyalkyl, and/or wherein two of $R_{10}$-$R_{18}$ form a linear or branched fused alkylene or alkylenedioxy ring on two adjacent atoms of $Y_{10}$-$Y_{14}$;

or a pharmaceutically acceptable salt, ester, hydrate, and/or solvate thereof.

Alternatively, compounds according to general structure Ia, having a D-galacto-configuration, are much preferred in this respect.

Similarly preferred compounds are compounds of general structure I or Ia, preferably I, in which X is a biphenyl according to general structure VI, VII or VIII as in:

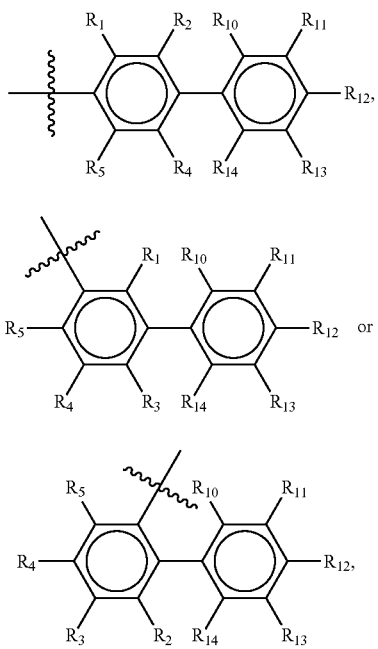

VI

VII

VIII wherein each of the group consisting of $R_1$-$R_4$ are independently selected from the group consisting of H, F, Cl, Br, I, CN, $CF_3$, and $C_1$-$C_8$ linear or branched alkyl, and $R_{10}$-$R_{14}$ are independently selected from the group consisting of H, F, Cl, Br, I, CN, $CF_3$, and $C_1$-$C_8$ linear or branched alkyl and/or wherein two of the group consisting of $R_{10}$-$R_{14}$ form a linear or branched fused alkylene or alkylenedioxy ring on two adjacent atoms as defined in general terms above.

Among the biphenyls, compounds of general structure VI with $R_1$-$R_{14}$=H, F of $CF_3$ are particularly preferred. Particularly preferred compounds for the treatment of symptoms of metabolic syndrome are

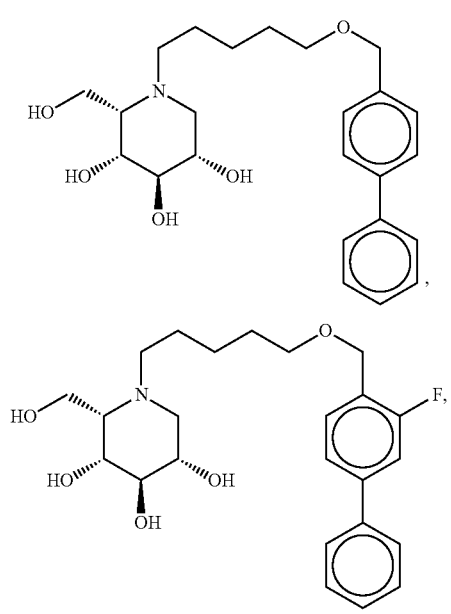

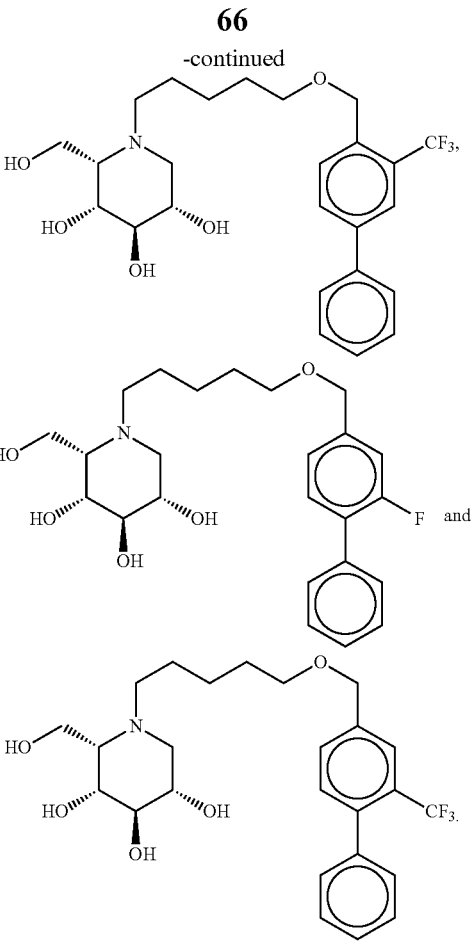

Therapeutic Application in Neurological Disorders

Compounds according to the present invention may also effectively be used in the treatment of neurological disorders, such as Parkinson's disease and Lewy-body dementia.

Neurological disorders, such as Parkinson's disease can be treated by compounds according the present invention which have high GCS and high GBA2 inhibition, as defined above. Preferably, GBA1 is inhibited as little as possible.

Therefore, compounds of general structure I or Ia, preferably I, defined above for the treatment of neurological disorders, such as Parkinson's disease and Lewy-body dementia, are preferably compounds wherein X is a biphenyl according to general structures VI, VII or VIII as in:

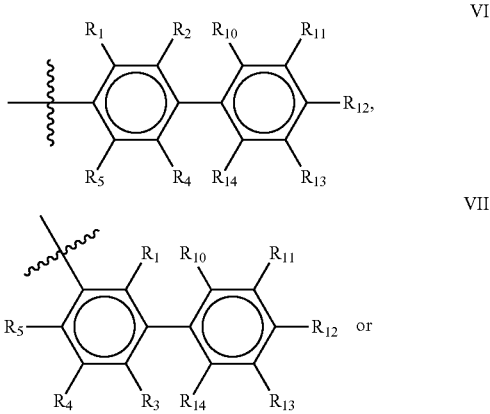

VI

VII

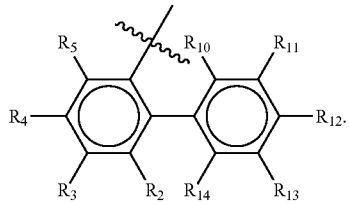

VIII wherein each of the group consisting of $R_1$-$R_4$ are independently selected from the group consisting of H, F, Cl, Br, I, CN, $CF_3$, and $C_1$-$C_8$ linear or branched alkyl, and $R_{10}$-$R_{14}$ are independently selected from the group consisting of H, F, Cl, Br, I, CN, $CF_3$, and $C_1$-$C_8$ linear or branched alkyl and/or wherein two of the group consisting of $R_{10}$-$R_{14}$ form a linear or branched fused alkylene or alkylenedioxy ring on two adjacent atoms.

Preferably for the biphenyls VI, VII and VIII, either all of $R_1$-$R_4$ or all of $R_{10}$-$R_{14}$ are selected from the group consisting of C, H and $CF_3$, and most preferably, all of $R_1$-$R_4$ and $R_{10}$-$R_{14}$ are selected from the group consisting of C, H and $CF_3$.

Among the biphenyls, biphenyls of general structure VI as defined above are particularly preferred.

Highly preferred compounds of the present invention are compounds selected from the group consisting of

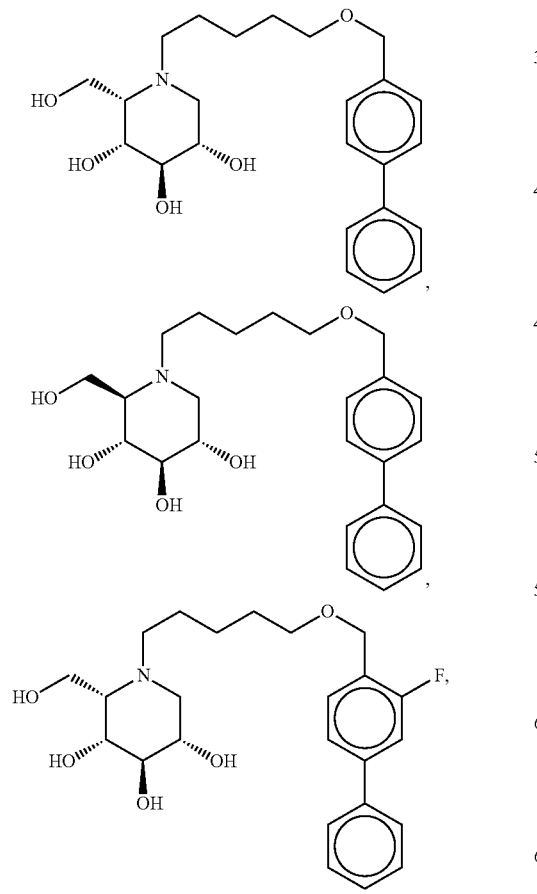

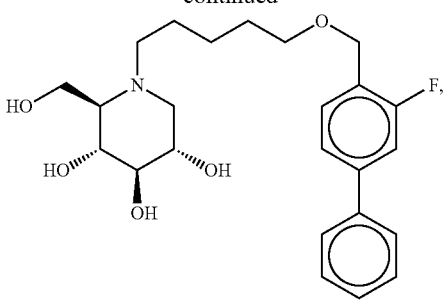

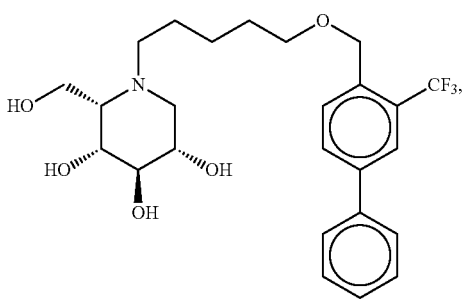

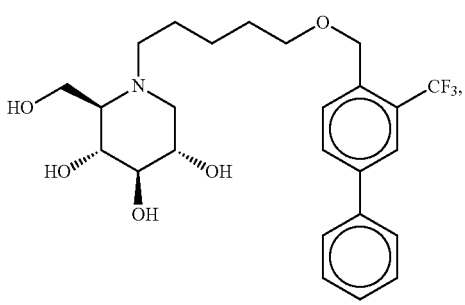

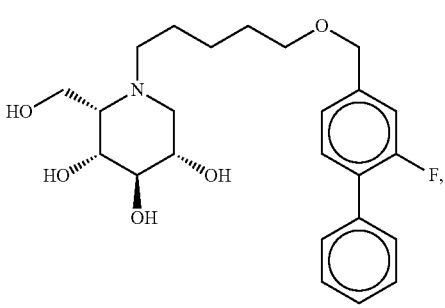

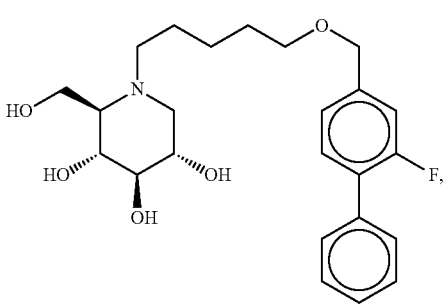

69

-continued

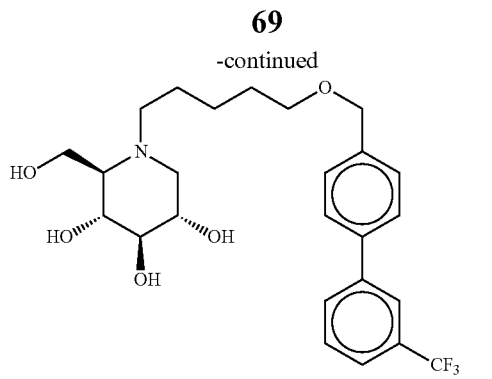
and

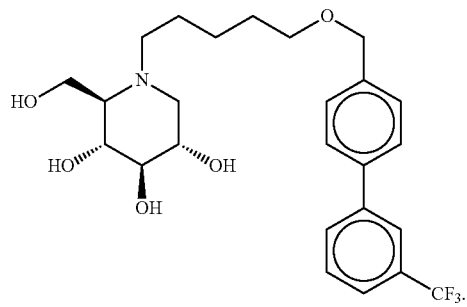

As has been mentioned above, and as is valid for all compounds of the present invention, also within this group the deoxynojirimycin derivative with an L-ido configuration is particularly preferred, i.e. compounds

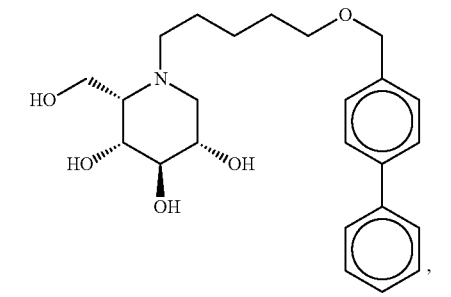

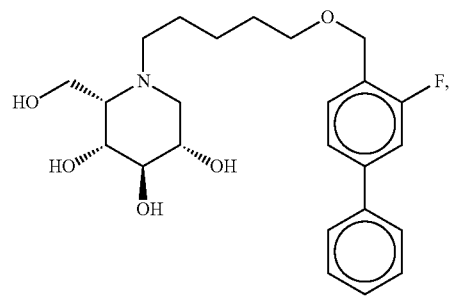

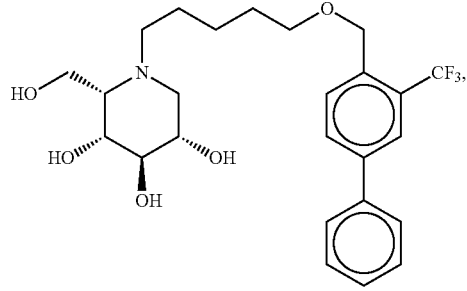

70

-continued

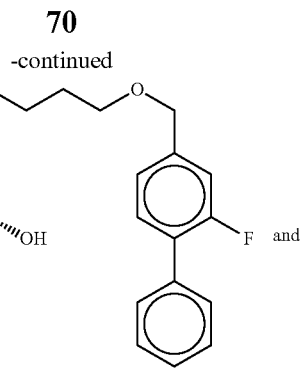
and

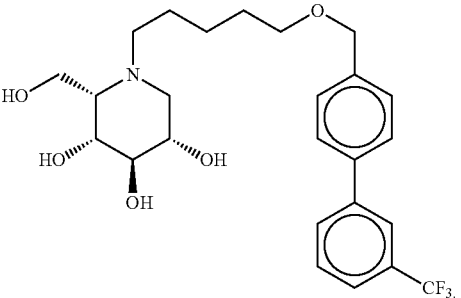

Therapeutic Application in Atherosclerosis

Compounds according to the present invention may also effectively be used in the treatment of atherosclerosis. In this case, preferred compounds are compounds that display a high inhibitory potency for GCS, as well as moderately to high inhibitory potency for GBA1.

Therefore, compounds of the present invention for therapeutic application in atherosclerosis are compounds according to general structure I defined above, wherein the deoxynojirimycin derivative has the D-gluco configuration.

More preferably, compounds of the present invention for therapeutic application in atherosclerosis are compounds according to general structure I defined above, wherein the deoxynojirimycin derivative is of the D-gluco configuration

XI

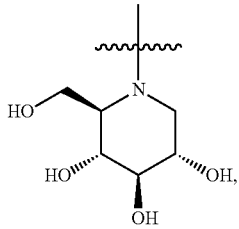

and wherein X=

VI

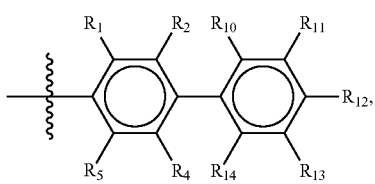

-continued

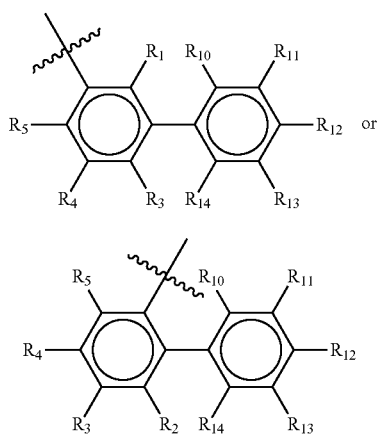

wherein each of the group consisting of $R_1$-$R_4$ are independently selected from the group consisting of H, F, Cl, Br, I, CN, $CF_3$, and $C_1$-$C_8$ linear or branched alkyl, and $R_{10}$-$R_{14}$ are independently selected from the group consisting of H, F, Cl, Br, I, CN, $CF_3$, and $C_1$-$C_8$ linear or branched alkyl and/or wherein two of the group consisting of $R_{10}$-$R_{14}$ form a linear or branched fused alkylene or alkylenedioxy ring on two adjacent atoms.

Alternatively, compounds according to general structure Ia, having a D-galacto-configuration, are much preferred in this respect, in particular those wherein X=

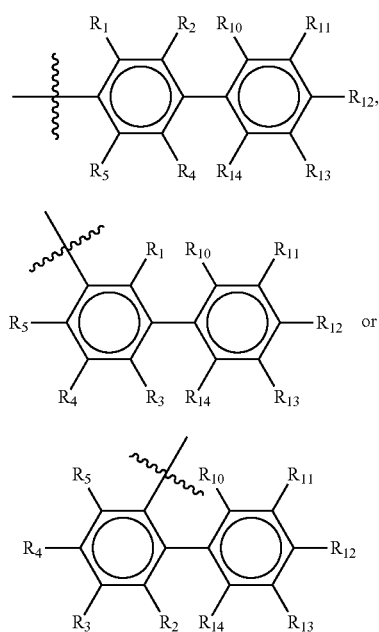

wherein each of the group consisting of $R_1$-$R_4$ are independently selected from the group consisting of H, F, Cl, Br, I, CN, $CF_3$, and $C_1$-$C_8$ linear or branched alkyl, and $R_{10}$-$R_{14}$ are independently selected from the group consisting of H, F, Cl, Br, I, CN, $CF_3$, and $C_1$-$C_8$ linear or branched alkyl and/or wherein two of the group consisting of $R_{10}$-$R_{14}$ form a linear or branched fused alkylene or alkylenedioxy ring on two adjacent atoms.

Compositions

Also, the invention provides a pharmaceutical composition comprising a compound as defined above as an active ingredient and a pharmaceutically acceptable excipient. Also, pharmaceutical compositions comprising several compounds according to general structure I and/or Ia as an active ingredient are considered as part of the invention.

A pharmaceutical composition containing one or two or more kinds of the compound of general structure I and/or Ia as an active ingredient can be prepared using excipients that are usually used in the art, that is, excipients for pharmaceutical preparations, carriers for pharmaceutical preparations, and the like according to the methods usually used.

Administration can be accomplished either by oral administration via tablets, pills, capsules, granules, powders, solutions, and the like, or parenteral administration, such as injections such as intra-articular, intravenous, and intramuscular injections, suppositories, ophthalmic solutions, eye ointments, or agents for external use, such as transdermal liquid preparations, ointments, transdermal patches, transmucosal liquid preparations, transmucosal patches, inhalers, and the like.

A solid composition for oral administration is in the form of tablets, powders, granules, or the like. In such a solid composition, one or more active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or a film of a gastric or enteric coating substance.

For solid oral formulation, suitable excipients are for instance diluents, fillers or bulking agents, such as lactose or microcrystalline cellulose, disintegrants, such as sodium starch glycolate or croscarmellose sodium, binders, such as polyvinyl pyrrolidone or hydroxypropylmethyl cellulose, lubricants, such as magnesium stearate, sweetening agents, such as sorbitol, saccharin, aspartame or acesulfame K, flavouring agents, such as peppermint, lemon oils, butterscotch or cinnamon and glidants, such as colloidal silica.

A liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, sweeteners, flavors, aromatics, or antiseptics.

For liquid oral formulation, suitable inert diluents include solvents/co-solvents, such as water, propylene glycol or glycerol, buffering agents, such as citrate, gluconate or lactate, preservatives such as sodium benzoate, parabens (e.g. methyl, propyl or butyl) or benzalkonium chloride, anti-oxidants, such as butylated hydroxytoluene or butylated hydroxyanisole, wetting agents, such as polysorbates or sorbitan esters, anti-foaming agents, such as simethicone, thickening agents, such as methyl cellulose or hydroxyethyl cellulose, sweetening agents, such as sorbitol, saccharin, aspartame or acesulfame K, flavouring agents, such as peppermint, lemon oils, butterscotch or cinnamon, and humectants, such as propylene glycol, glycerol or sorbitol.

Injections for parenteral administration include sterile aqueous or non-aqueous solutions, suspensions and emulsions. The aqueous solvent includes, for example, distilled water for injection and physiological saline. Examples of the non-aqueous solvent include alcohols such as ethanol. Such a composition may further contain a tonicity agent, an antiseptic, a moistening agent, an emulsifying agent, a dispersing agent, a stabilizer, or a solubilizing aid. These are sterilized, for example, by filtration through a bacteria retaining filter, by blending a bactericide, or irradiation. In addition, these can also be used by preparing a sterile solid composition, and dissolving or suspending it in sterile water or a sterile solvent for injection prior to its use.

An agent for external use includes ointments, plasters, creams, jellies, poultices, sprays, lotions, eye drops, eye ointments, and the like. The agents contain generally used ointment bases, lotion bases, aqueous or non-aqueous liquid preparations, suspensions, emulsions, and the like.

As a transmucosal agent, such as an inhaler, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizer, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, carbon dioxide, and the like.

In oral administration, the daily dose is generally from about 0.001 to 100 mg/kg, preferably from 0.1 to 30 mg/kg, and more preferably 0.1 to 10 mg/kg, per body weight, administered in one portion or in 2 to 4 separate portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided upon in response to the individual case by taking the symptoms, the age, and the gender, and the like into consideration.

The compound of general structure I or Ia, preferably I, can be used in combination with various therapeutic or prophylactic agents for the diseases for which the compound is considered to be effective, as described above. The combined preparation may be administered simultaneously, or separately and continuously, or at a desired time interval. The preparations to be administered simultaneously may be a blend, or may be prepared individually.

As an alternative, controlled-release may be used with compounds of the present invention. Such formulations are preferably formulated following oral or dermal administration modes.

Furthermore, the invention provides use of the compounds defined above for inhibiting glycosylceramide synthase (GCS) and/or neutral glucosylceramidase (GBA2) in vitro or in vivo.

Thus, the invention provides compounds and/or pharmaceutical compositions comprising a compound as defined above for use in a method of treatment of the human or animal body by therapy, as well as a method of treatment of a subject in need thereof comprising administering a therapeutically effective amount of a compound or pharmaceutical composition as defined above to said subject, wherein the compound or composition is effective to restore irregular levels of glycosylceramide to natural levels.

EXAMPLES

Example 1: Preparation of Compounds of the Present Invention

In ROUTE A, the key step is the direct alkylation of the unprotected iminosugar IX or XI to the functionalized alkyl substituent under alkaline conditions.

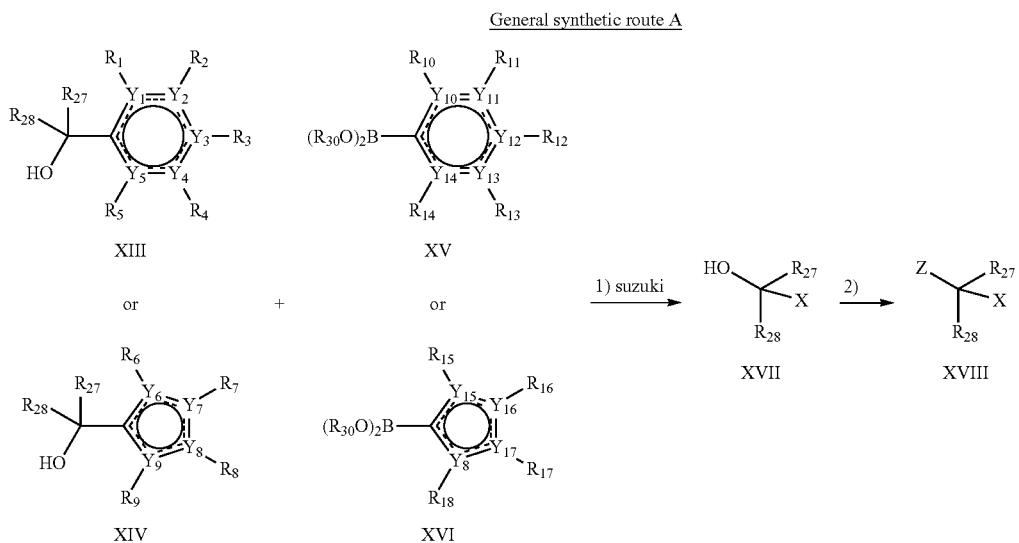

General synthetic route A one of $R_1 - R_9 = Z$;
B = boronic acid/ester wherein R30 is selected from the group consisting of H, linear or branched alkyl, and an aromatic group according to general structure IV or V;

-continued

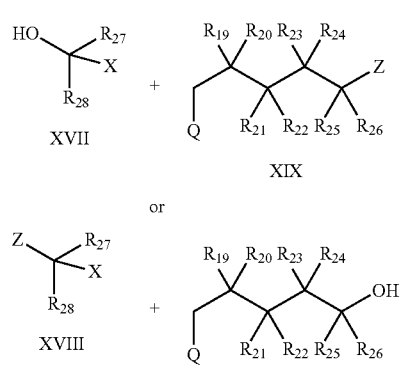
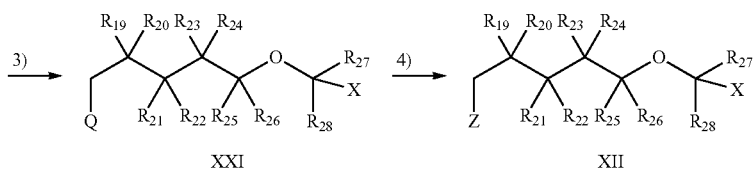

Q = protecting group

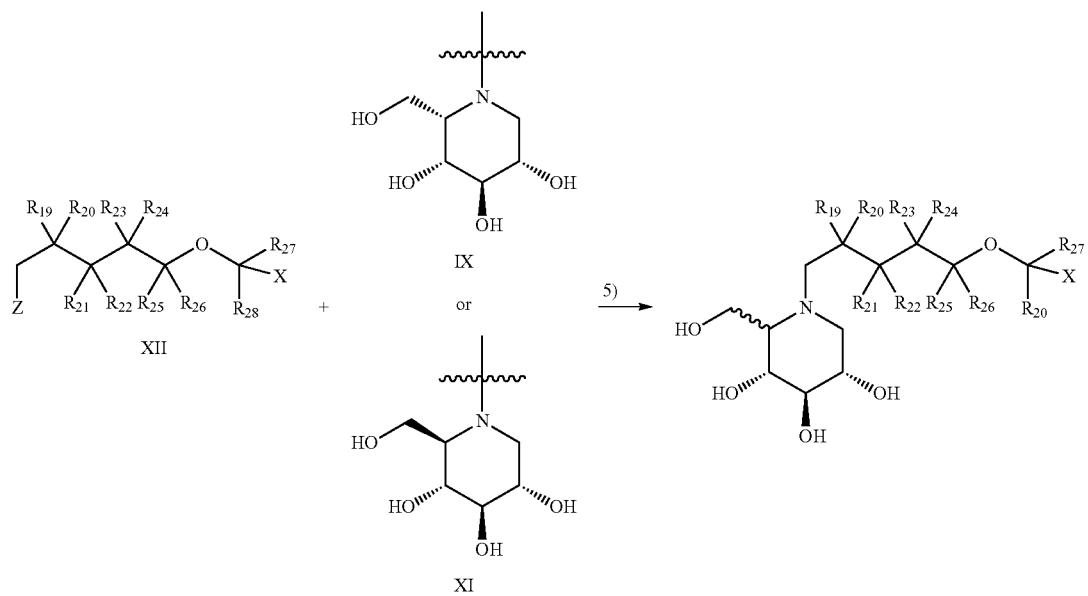

The reactions which involved Suzuki cross-coupling chemistry were carried out under an argon atmosphere. The (stock) solutions were degassed for 1 h using an ultrasound bath and a stream of argon. A stock solution of the Z-substituted compound XIII or XIV (1.2 M) in ethanol, a stock solution of the boronic acid XV or XVI (1.5 M) in ethanol and a stock solution of Pd(PPh$_3$)$_4$ (5%) ethanol were made. To a reaction vessel were successively added NaOMe (0.180 gram, 3.3 mmol as a solid the final volume is 0.417+0.5+ 0.4+=1.1317 ml=2.5 M concentration), Z-substituted compound XIII or XIV (1.2 M, 0.417 mL, 0.5 mmol), boronic acid XV or XVI (1.5 M, 0.500 mL, 0.75 mmol) and Pd(PPh$_3$)$_4$ (2 mol %, 0.40 mL). The reaction mixture was stirred at 65° C. for 8-18 h. after which HPLC analysis indicated the complete consumption of starting material. The reaction mixture was diluted with EtOAc/MeOH (1:1, v/v) and filtered over silica gel. The volatiles evaporated and the residue purified by RP-HPLC purification, using an automated HPLC system equipped with a semi-preparative C18 column (5 μm C18, 10 Å, 150×21.2 mm). The applied buffers were A: H$_2$O+trifluoroacetic acid (1% mM) and B: MeCN. Isolated yields after HPLC purification vary from 15%-47%.

Conversion of XVII to XVIII (step 2) was carried out by dissolving XVII in DCM (0.1 M) and treat this with triphenylphosphine (2 equivalents) and tetrabromomethane (2 equivalents) at 0° C. Celite (~1 gram/mmol) was added and the volatiles evaporated. The residue was purified by silica gel column chromatography (elution with ethyl acetate and petroleum ether).

The preparation of XXI from XVII or XVIII and XIX or XX (step 3) was carried out by adding sodium hydride (1.5 equivalent) to the alcohol dissolved in DMF (0.3 M). The mixture was stirred for 1 hour at 75° C. subsequently add XIX or XVIII and the mixture was stirred for 1 h. The mixture was diluted with ethyl acetate and washed with water, and brine. The organic layer was dried (MgSO4) and the volatiles were evaporated. The residue was purified by silica gel column chromatograph (elution with ethyl acetate petroleum ether).

The conversion of XXI to XII (step 4) was carried out by treating XXI with boron trifluoride diethyl etherate (1.5 equivalents) in a mixture of toluene and methanol (1:1, v/v). The mixture was washed with sodium carbonate (2 M) and the organic layer dried (MgSO4). the volatiles were evaporated and the residue purified by silica gel column chromatograph (elution with ethyl acetate petroleum ether).

Alkylation of deprotected deoxynojirimycin IX or XI (step 5 in route A) was carried out by stirring deprotected deoxynojirimycin at a temperature between 20 and 154° C.

in the presence of a compound of general structure XII in DMF at 0.2 M substrate concentration, at stoichiometric amounts, in the presence of a three-fold excess of potassium carbonate. The reaction mixture was filtrated over a plug of celite, and the eluate was neutralized with acetic acid. The volatiles were evaporated and the residue purified by high performance liquid chromatography.

An alternative route to compounds of general structure I is provided as route B. In route B, aromatic compounds XXII or XXIII are coupled to the pentyl spacer moiety XIX or XX to give compound XXIV. Deprotection of XXIV provides compound XXV, which can be reacted with deoxynojirimycin of the D-gluco or L-ido configuration (XI or XI) to provide compound XXVI. Subsequent suzuki coupling with second aromatic ring moieties XV or XVI thus provides compound I.

In route B, step 6 is performed using the following conditions Alcohol was dissolved in DMF (0.3 M) and treated with sodium hydride (1.5 equivalent). This mixture was stirred for 1 hour at 75° C. and subsequently add XIX or XXIII was added and stirred for 1 h. The mixture was diluted with ethyl acetate and wash with water, and brine. The organic layer was dried (MgSO4) and the volatiles evaporated. The residue was purified by silica gel column chromatograph (elution with ethyl acetate petroleum ether).

In route B, step 7 is performed using the following conditions: XXIV was treated with boron trifluoride diethyl etherate (1.5 equivalents) in a mixture of toluene and methanol (1:1, v/v). The mixture was washed with sodium carbonate (2 M) and the organic layer dried (MgSO4). The volatiles were removed and the residue purified by silica gel column chromatograph (elution with ethyl acetate petroleum ether)

Intermediate of above was dissolving in DCM (0.1 M) and treated with triphenylphosphine (2 equivalents) and tetrabromomomethane (2 equivalents) at 0° C. Celite (~1 gram/mmol) was added and the volatiles evaporated. The residue was purified by silica gel column chromatography (elution with ethyl acetate and petroleum ether).

In route B, step 8 is performed using the following conditions: IX or XI was treated with XXV (1.0 equivalents) and potassium carbonate in DMF (0.2 M) at elevated temperature (80° C.). Reaction was filtrated over a plug of celite, the eluate neutralized with acetic acid. The volatiles were evaporated and the residue purified by silica gel column chromatography (elution methanol ethyl acetate)

In route B, step 9 is performed using the following conditions: Suzuki cross-coupling chemistry were carried out with XXVI and XV or XVI under an argon atmosphere. The (stock) solutions were degassed for 1 h using an ultrasound bath and a stream of argon. A stock solution of XXVI (1.2 M) in ethanol, a stock solution of the boronic acid XV or XVI (1.5 M) in ethanol and a stock solution of Pd(PPh$_3$)$_4$ (5%) ethanol were made. To a reaction vessel were successively added NaOMe (0.180 gram, 3.3 mmol (2.5 M), XXVI (1.2 M, 0.417 mL, 0.5 mmol), boronic acid XV or XVI (1.5 M, 0.500 mL, 0.75 mmol) and Pd(PPh$_3$)$_4$ (2 mol %, 0.40 mL). The reaction mixture was stirred at 65° C. for 8-18 h, after which HPLC analysis indicated the complete consumption of starting material. The reaction mixture was diluted with EtOAc/MeOH (1:1, v/v) and filtered over silica gel. The volatiles evaporated and the residue purified by RP-HPLC purification, using an automated HPLC system equipped with a semi-preparative C18 column (5 µm C18, 10 Å, 150×21.2 mm). The applied buffers were A: H$_2$O+ trifluoroacetic acid (1% mM) and B: MeCN. Isolated yields after HPLC purification vary from 15%-47%.

General synthetic route B

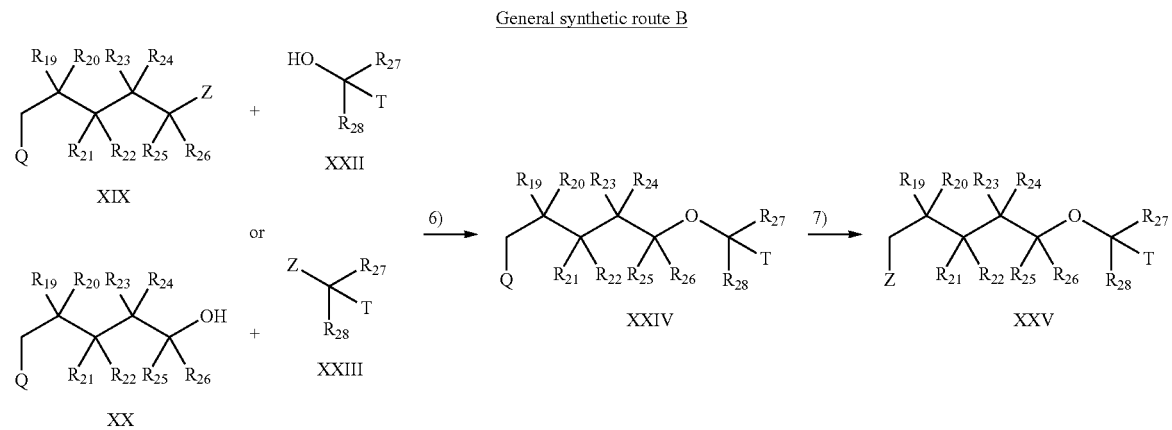

Q = protecting group

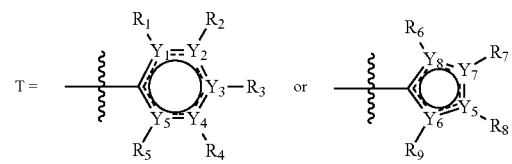

wherein one of R1 - R9 = Z

-continued

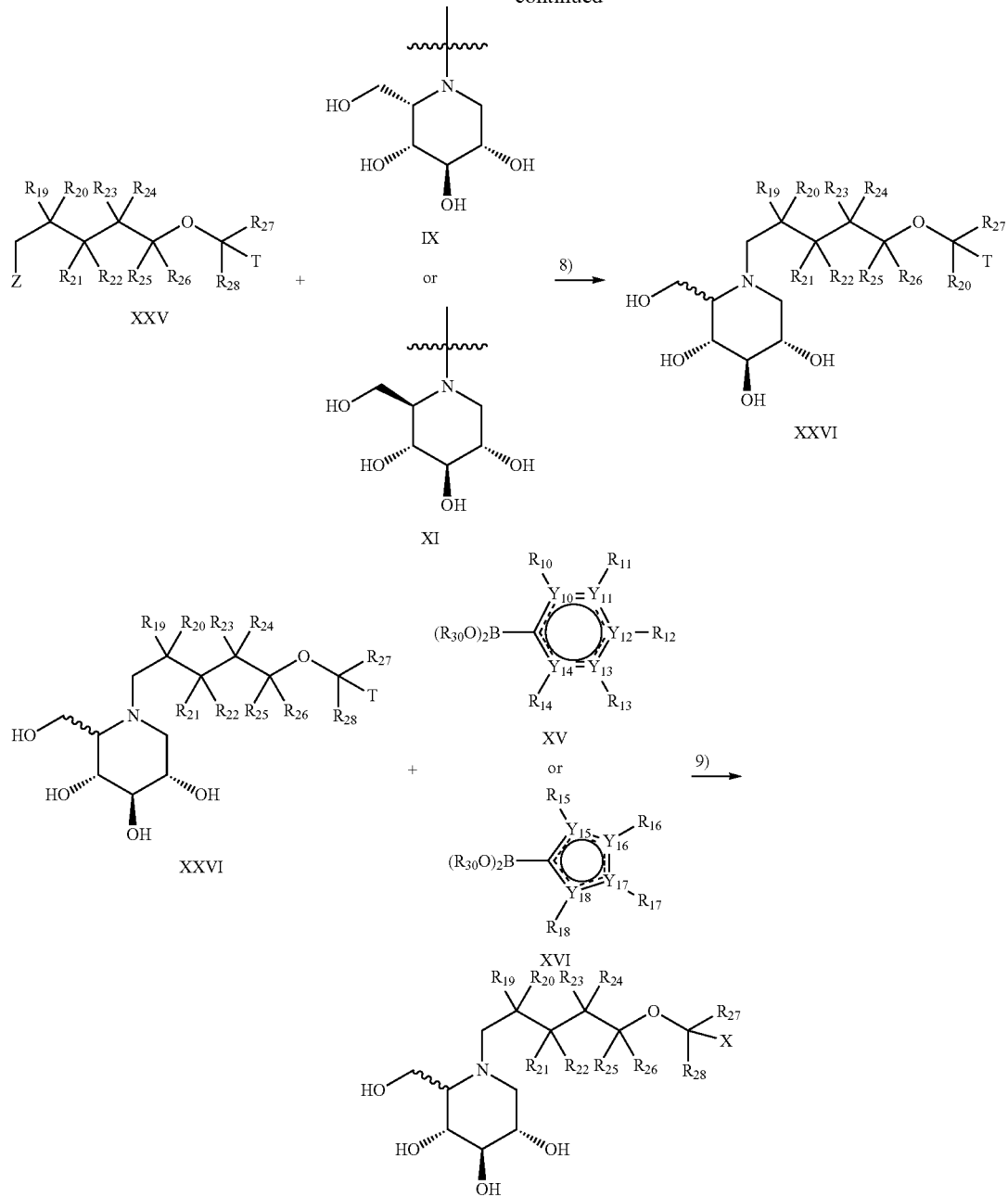

B = boronic acid/ester wherein R30 is selected from the group consisting of H, linear or branched alkyl, and an aromatic group according to general structure IV or V;

Final compounds of general structure I prepared by route A were: 1, 3, 4, 5, 6, 7, 8, 9, 10, 11, 12, 13, 14, 2, 37, 38, 39, 40, 41, 42, 43, 44, 45, 46, and 47.

Final compounds of general structure I prepared by route B were: 15, 16, 17, 18, 19, 20, 21, 22, 23, 24, 25, 26, 27, 28, 29, 30, 31, 32, 33, 34, 35, and 36.

D-deoxygalactonojirimycin derivatives can generally be prepared following either route A or route B, using D-deoxygalactonojirimycin instead of D-gluco or L-ido deoxynojirimycin.

All compounds are purified to >95% purity by preparative HPLC. HPLC system equipped with a semi-preparative C18 column (5 μm C18, 10 Å, 150×21.2 mm). The applied buffers were A: $H_2O$+trifluoroacetic acid (1% mM) and B: MeCN.

Example 2: Determination of the Inhibitory Potency

GCS.

$IC_{50}$ values for GCS activity were measured using living cells (macrophage RAW-267 cells grown to confluence in RPMI-1640+10% foetal calf serum (BSA) in a 5% $CO_2$ incubator). Cells were washed with RPMI medium without serum (3×5 ml) and next exposed to 3 ml RPMI+0.3 mM conduritol B-epoxide, tested inhibitor and 5 nmol 6-[N-

Methyl-N-(7-nitrobenz-2-oxa-1,3 diazol-4-yl)aminododecanoyl]sphingosyl-β-d-glucoside (C6-NBD-glucosylceramide) complex with BSA, successively. The cells were incubated for one hour at 37° Celsius and washed with medium without serum (5×5 ml). A 50 mM potassium phosphate buffer, pH 5.8, 0.75 ml) was added and the flask placed on ice. Cells were removed by scraping and the harvested cells collected in a vial that was immediately immersed in liquid nitrogen. The frozen cell lysate was suspended in 3 ml methanol and extracted with chloroform (3 ml). After extraction a 0.73% NaCl solution (2 ml) was added. After phase separation, the aqueous phase was extracted once more with chloroform (1 ml). The combined chloroform layers were isolated and concentrated at 30-40° Celsius under a nitrogen flow. Lipids were separated by thin-layer chromatography (HP-TLC plates 20×10 silicagel 60, Merck) using chloroform/methanol/15 mM aq $CaCl_2$) (60:35:8, v/v) as the developing solvent. The NBD-labelled lipids were identified using standards, visualized with a Typhoon Trio Variable Mode imager (excitation at 488 nM, emission at 520 nM) and quantified with ImageQuant TL Software.

GBA1.

$IC_{50}$ values for GBA1 were measured using recombinant human enzyme (Cerezyme, Sanofi). The activity of GBA1 was determined with the artificial 4-methylumbelliferyl-β-glucoside (4-MU-β-glucoside, Sigma) substrate as described previously (Aerts et al. Eur. J. Biochem. 1985, 150, 565-574).

Briefly, enzyme was incubated in the absence and presence of tested inhibitor with 3.7 mm 4-MU-β-glucoside in McIlvaine buffer (0.1 m citrate and 0.2 m phosphate buffer), pH 5.2, in the presence of 0.1% Triton X-1100 and 0.2 (w/v) sodium taurocholate 37° C. The reaction was stopped by the addition of glycine/NaOH (pH 10.6). The amount of liberated 4-MU was determined with a PerkinElmer Life Sciences LS30 fluorimeter.

GBA2.

$IC_{50}$ values for GBA2 were measured using a membrane fraction obtained from Gaucher spleen treated for 30 min with 1 mM conduritol B-epoxide to irreversibly inhibit residual GBA1 activity. The activity of the non-lysosomal glucosylceramidase GBA2 in the preparation was measured with the artificial 4-methylumbelliferyl-β-glucoside (4-MU-β-glucoside, Sigma) substrate as described previously (van Weely et al. Biophys. Acta 1993, 1181, 55-62). Briefly, enzyme preparation was incubated in the absence and presence of tested inhibitor with 3.7 mm 4-MU-β-glucoside in McIlvaine buffer (0.1 m citrate and 0.2 m phosphate buffer), pH 5.8. Assays were performed at 37° C. and stopped by the addition of glycine/NaOH (pH 10.6). The amount of liberated 4-MU was determined with a PerkinElmer Life Sciences LS30 fluorimeter.

Intestinal Glycosidases.

$IC_{50}$ values for lactase (lactase/phoridzin hydrolase), maltase, and sucrase (sucrase-isomaltase) were measured with natural disaccharide substrates using homogenates of freshly isolated mouse intestine as described earlier (Wennekes et al. J. Org. Chem. 2007, 72, 1088-1097). Liberated glucose from the corresponding disaccharide substrates was enzymatically determined as described earlier (Andersson et al. BioChem. Pharmacol. 2000, 59, 821-829).

Example 3: Inhibitory Potency of Deoxynojirimycin Derivatives of the D-Gluco Configuration Towards GCS, GBA1 and GBA2

| compound number | structure | GCS [nM] | GBA2 [nM] | GBA1 [nM] |
|---|---|---|---|---|
| 1 | 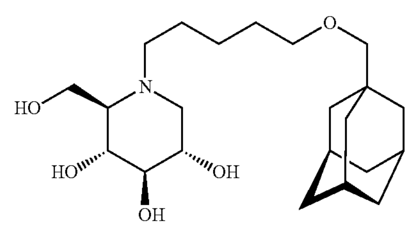 | 200 | 2 | 100 |
| 3 | 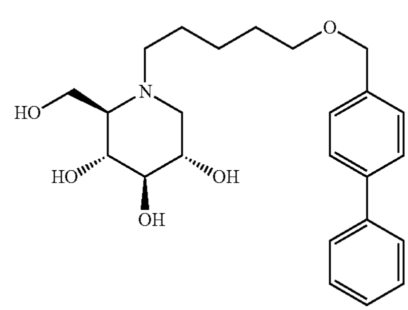 [SMILES: OC[C@@H]1[C@@H](O)[C@H](O)[C@@H](O)CN1CCCCCOCc1ccc(-c2ccccc2)cc1] | 40 | 0.7 | 1000 |

-continued
| compound number | structure | GCS [nM] | GBA2 [nM] | GBA1 [nM] |
|---|---|---|---|---|
| 4 | 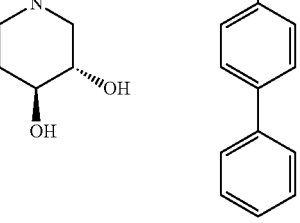 | 50 | 2 | 10.000 |
| 5 | 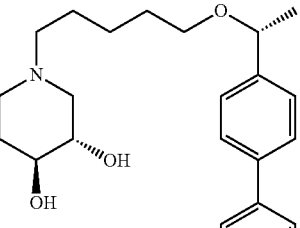 | 40 | 1 | 10.000 |
| 6 | 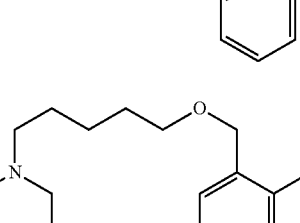 | 25 | 0.08 | 250 |
| 7 | 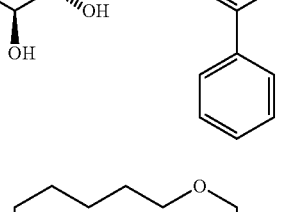 | 25 | 0.08 | 200 |
| 8 | 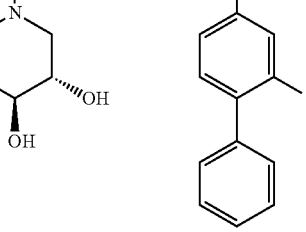 | 25 | 0.12 | 200 |

-continued

| compound number | structure | GCS [nM] | GBA2 [nM] | GBA1 [nM] |
|---|---|---|---|---|
| 9 | 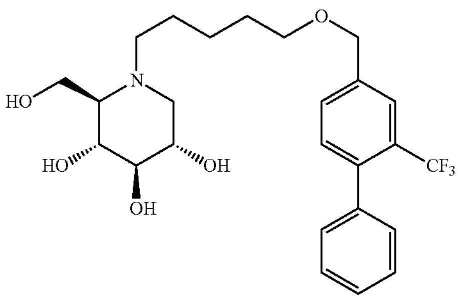 [SMILES: OC[C@@H]1[C@@H](O)[C@H](O)[C@@H](O)CN1CCCCCOCc1ccc(-c2ccccc2)c(C(F)(F)F)c1] | 25 | 0.08 | 100 |
| 10 | 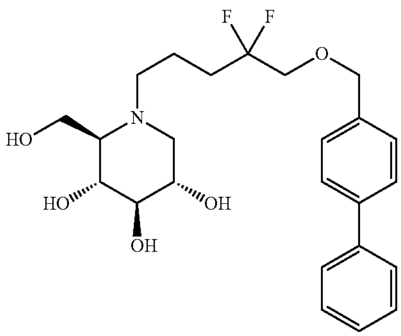 [SMILES: OC[C@@H]1[C@@H](O)[C@H](O)[C@@H](O)CN1CCCC(F)(F)COCc1ccc(-c2ccccc2)cc1] | 15 | 2 | 12500 |
| 11 | 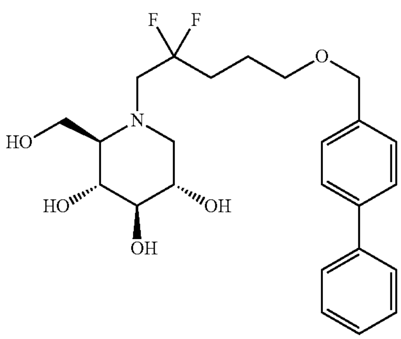 [SMILES: OC[C@@H]1[C@@H](O)[C@H](O)[C@@H](O)CN1CC(F)(F)CCCOCc1ccc(-c2ccccc2)cc1] | 200 | 2 | 500 |
| 12 | 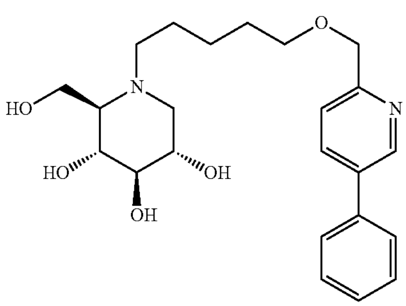 [SMILES: OC[C@@H]1[C@@H](O)[C@H](O)[C@@H](O)CN1CCCCCOCc1ccc(-c2ccccc2)cn1] | 200 | 3 | 1500 |
| 13 | 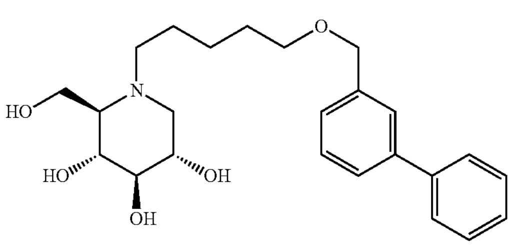 [SMILES: OC[C@@H]1[C@@H](O)[C@H](O)[C@@H](O)CN1CCCCCOCc1cccc(-c2ccccc2)c1] | 75 | 2 | 300 |

-continued
| compound number | structure | GCS [nM] | GBA2 [nM] | GBA1 [nM] |
|---|---|---|---|---|
| 14 | 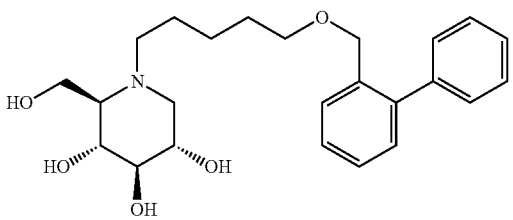 [SMILES: OC[C@@H]1[C@@H](O)[C@H](O)[C@@H](O)CN1CCCCCOCc1ccccc1-c1ccccc1] | 50 | 3 | 1250 |
| 15 | 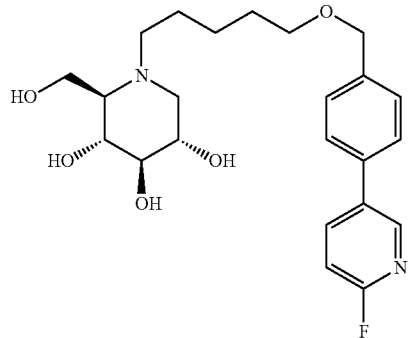 [SMILES: OC[C@@H]1[C@@H](O)[C@H](O)[C@@H](O)CN1CCCCCOCc1ccc(-c2ccc(F)nc2)cc1] | 750 | 5 | 3000 |
| 16 | 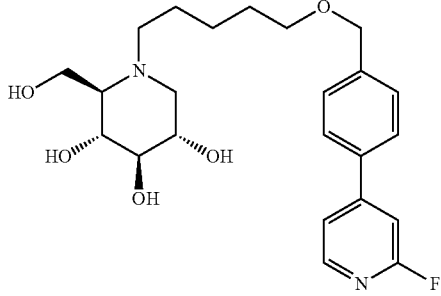 [SMILES: OC[C@@H]1[C@@H](O)[C@H](O)[C@@H](O)CN1CCCCCOCc1ccc(-c2ccnc(F)c2)cc1] | 150 | 4 | 2000 |
| 17 | 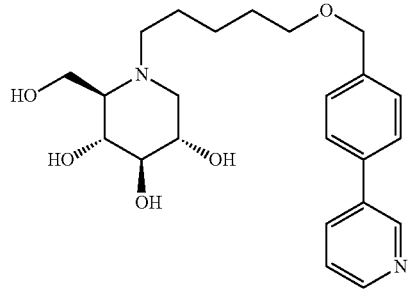 [SMILES: OC[C@@H]1[C@@H](O)[C@H](O)[C@@H](O)CN1CCCCCOCc1ccc(-c2cccnc2)cc1] | 200 | 10 | 3000 |
| 18 | 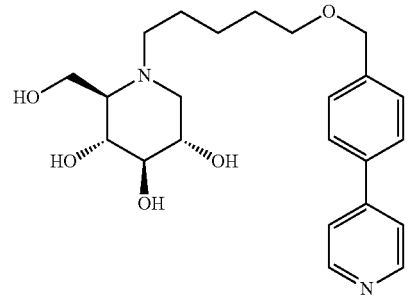 [SMILES: OC[C@@H]1[C@@H](O)[C@H](O)[C@@H](O)CN1CCCCCOCc1ccc(-c2ccncc2)cc1] | 2000 | 10 | 2000 |

-continued
| compound number | structure | GCS [nM] | GBA2 [nM] | GBA1 [nM] |
|---|---|---|---|---|
| 19 | 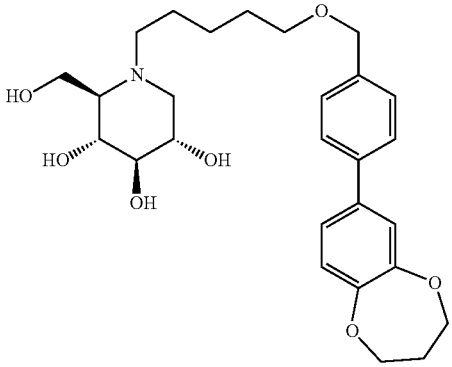 [SMILES: OC[C@@H]1[C@@H](O)[C@H](O)[C@@H](O)CN1CCCCCOCc1ccc(-c2ccc3c(c2)OCCCO3)cc1] | 25 | 10 | 3000 |
| 20 | 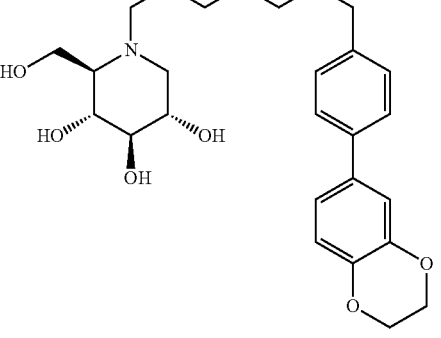 | 25 | 10 | 3000 |
| 21 | 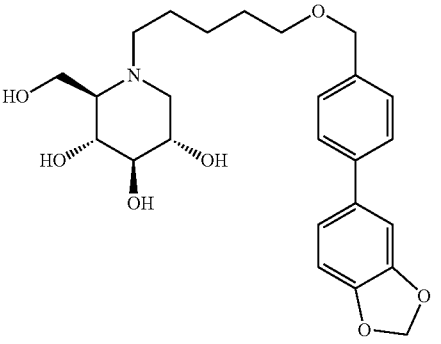 [SMILES: OC[C@@H]1[C@@H](O)[C@H](O)[C@@H](O)CN1CCCCCOCc1ccc(-c2ccc3c(c2)OCO3)cc1] | 25 | 10 | 2500 |
| 22 | 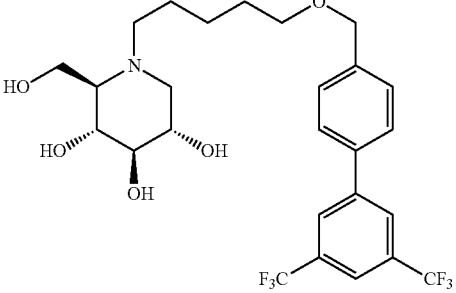 | 20 | 15 | 800 |

-continued

| compound number | structure | GCS [nM] | GBA2 [nM] | GBA1 [nM] |
|---|---|---|---|---|
| 23 | 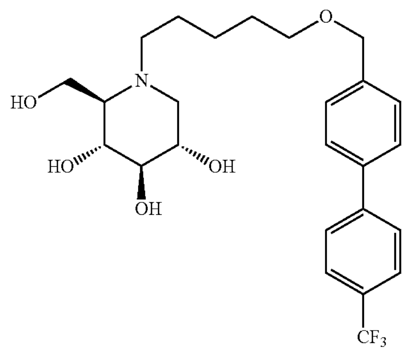 [SMILES: OC[C@@H]1[C@@H](O)[C@H](O)[C@@H](O)CN1CCCCCOCc1ccc(-c2ccc(C(F)(F)F)cc2)cc1] | 20 | 10 | 800 |
| 24 | 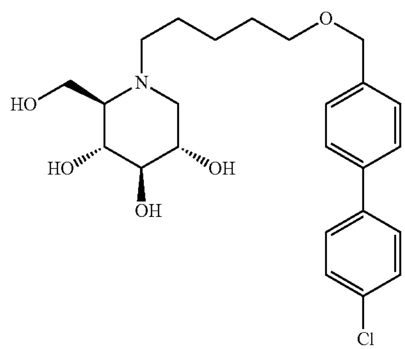 | 25 | 2 | 500 |
| 25 | 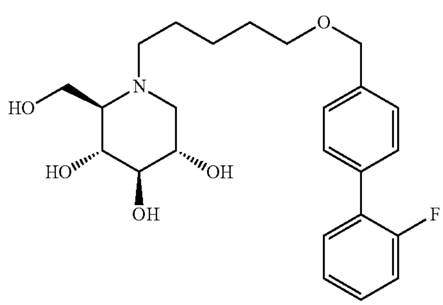 [SMILES: OC[C@@H]1[C@@H](O)[C@H](O)[C@@H](O)CN1CCCCCOCc1ccc(-c2ccccc2F)cc1] | 74 | 2 | 600 |
| 26 | 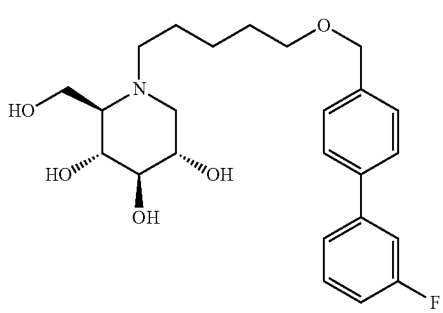 [SMILES: OC[C@@H]1[C@@H](O)[C@H](O)[C@@H](O)CN1CCCCCOCc1ccc(-c2cccc(F)c2)cc1] | 25 | 2 | 250 |

-continued
| compound number | structure | GCS [nM] | GBA2 [nM] | GBA1 [nM] |
|---|---|---|---|---|
| 27 | 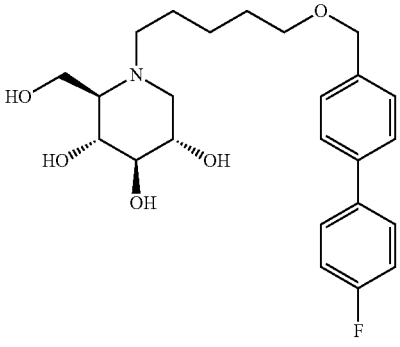 [SMILES: OC[C@@H]1[C@@H](O)[C@H](O)[C@@H](O)CN1CCCCCOCc1ccc(-c2ccc(F)cc2)cc1] | 25 | 1 | 400 |
| 28 | 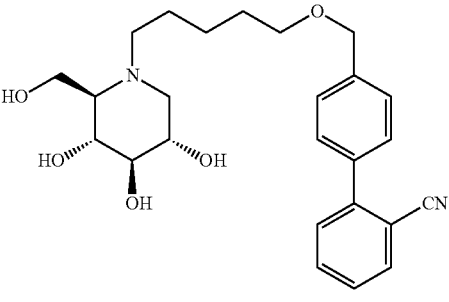 [SMILES: N#Cc1ccccc1-c1ccc(COCCCCCN2C[C@H](O)[C@@H](O)[C@H](O)[C@H]2CO)cc1] | 150 | 5 | 600 |
| 29 | 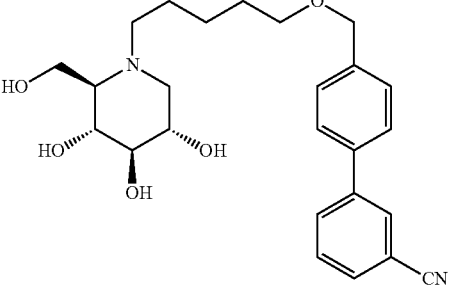 | 50 | 2 | 700 |
| 30 | 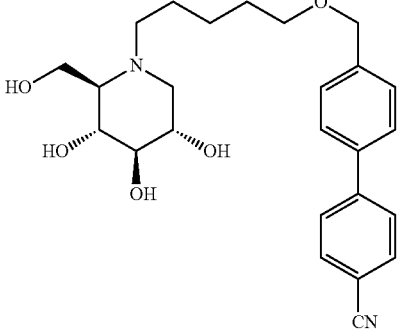 | 150 | 3 | 350 |

-continued

| compound number | structure | GCS [nM] | GBA2 [nM] | GBA1 [nM] |
|---|---|---|---|---|
| 31 | 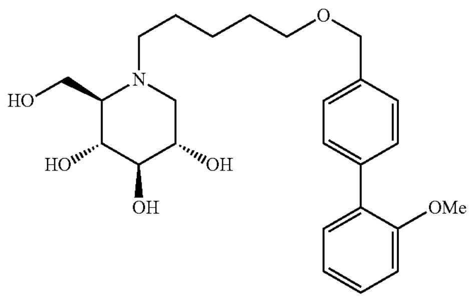 [SMILES: COc1ccccc1-c1ccc(COCCCCCN2C[C@H](O)[C@@H](O)[C@H](O)[C@H]2CO)cc1] | 50 | 0.7 | 600 |
| 32 | 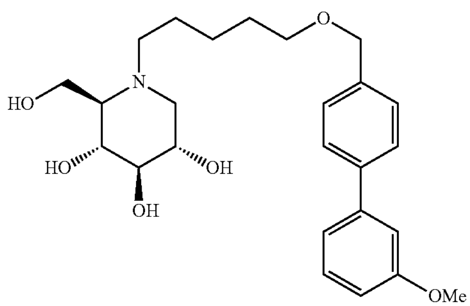 [SMILES: COc1cccc(-c2ccc(COCCCCCN3C[C@H](O)[C@@H](O)[C@H](O)[C@H]3CO)cc2)c1] | 150 | 20 | 2500 |
| 33 | 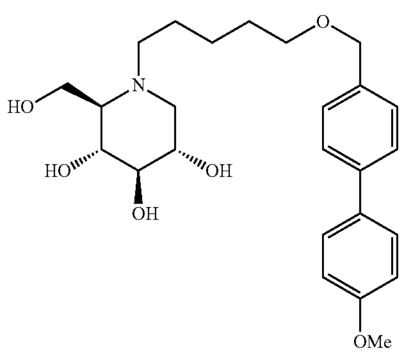 [SMILES: COc1ccc(-c2ccc(COCCCCCN3C[C@H](O)[C@@H](O)[C@H](O)[C@H]3CO)cc2)cc1] | 25 | 10 | 2500 |
| 34 | 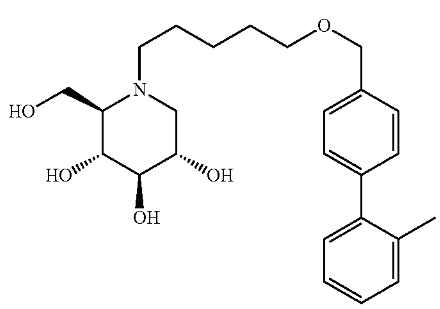 [SMILES: Cc1ccccc1-c1ccc(COCCCCCN2C[C@H](O)[C@@H](O)[C@H](O)[C@H]2CO)cc1] | 25 | 0.5 | 70 |
| 35 | 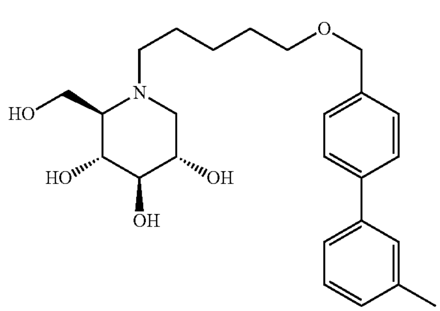 [SMILES: Cc1cccc(-c2ccc(COCCCCCN3C[C@H](O)[C@@H](O)[C@H](O)[C@H]3CO)cc2)c1] | 100 | 2 | 250 |

-continued

| compound number | structure | GCS [nM] | GBA2 [nM] | GBA1 [nM] |
|---|---|---|---|---|
| 36 | 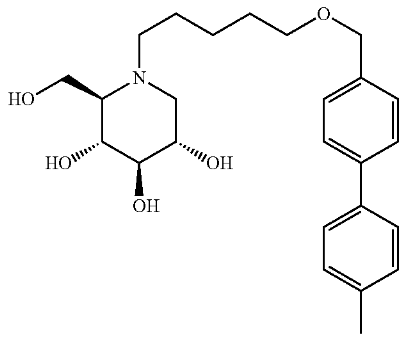 [SMILES: Cc1ccc(-c2ccc(COCCCCCN3C[C@H](O)[C@@H](O)[C@H](O)[C@H]3CO)cc2)cc1] | 100 | 3 | 250 |

Example 4: Inhibitory Potency of Deoxynojirimycin Derivatives of the L-Ido Configuration Towards GCS, GBA1 and GBA2

| compound number | structure | GCS [nM] | GBA2 [nM] | GBA1 [nM] |
|---|---|---|---|---|
| 2 | 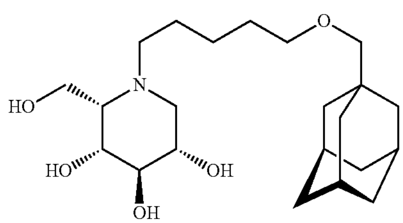 | 100 | 1 | 2000 |
| 37 | 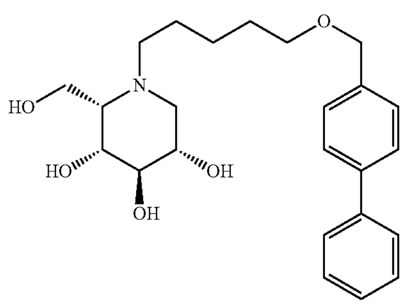 [SMILES: OC[C@H]1[C@@H](O)[C@H](O)[C@@H](O)CN1CCCCCOCc1ccc(-c2ccccc2)cc1] | 3 | 1 | 12500 |
| 38 | 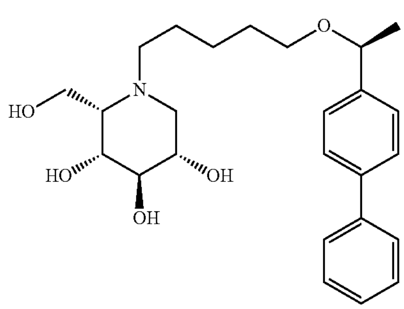 [SMILES: C[C@H](OCCCCCN1C[C@H](O)[C@@H](O)[C@H](O)[C@@H]1CO)c1ccc(-c2ccccc2)cc1] | 30 | 2 | 10000 |

-continued

| compound number | structure | GCS [nM] | GBA2 [nM] | GBA1 [nM] |
|---|---|---|---|---|
| 39 | 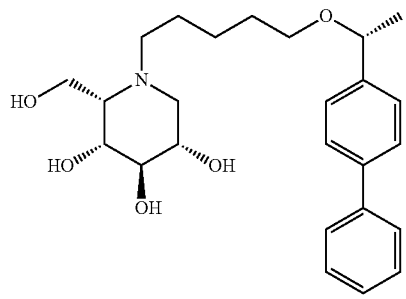 [SMILES: C[C@@H](OCCCCCN1C[C@H](O)[C@@H](O)[C@H](O)[C@@H]1CO)c1ccc(-c2ccccc2)cc1] | 40 | 1 | 10000 |
| 40 | 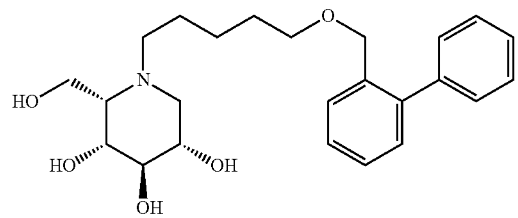 [SMILES: OC[C@H]1[C@@H](O)[C@H](O)[C@@H](O)CN1CCCCCOCc1ccccc1-c1ccccc1] | 25 | 3 | 15000 |
| 41 | 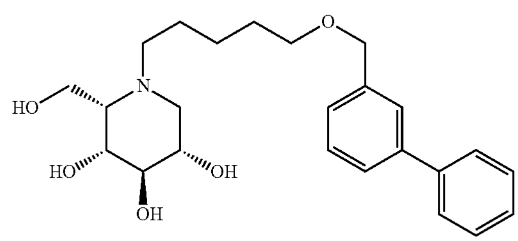 [SMILES: OC[C@H]1[C@@H](O)[C@H](O)[C@@H](O)CN1CCCCCOCc1cccc(-c2ccccc2)c1] | 75 | 2 | 20000 |
| 42 | 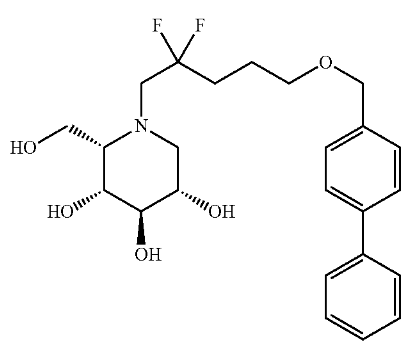 [SMILES: OC[C@H]1[C@@H](O)[C@H](O)[C@@H](O)CN1CC(F)(F)CCCOCc1ccc(-c2ccccc2)cc1] | 20 | 2 | 500000 |
| 43 | 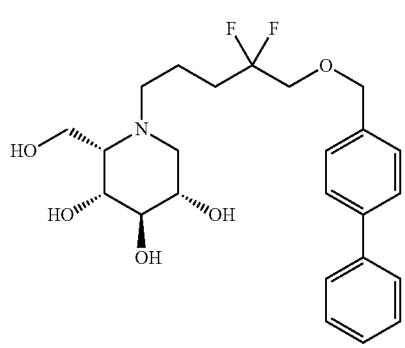 [SMILES: OC[C@H]1[C@@H](O)[C@H](O)[C@@H](O)CN1CCCC(F)(F)COCc1ccc(-c2ccccc2)cc1] | 15 | 2 | 12500 |

-continued

| compound number | structure | GCS [nM] | GBA2 [nM] | GBA1 [nM] |
|---|---|---|---|---|
| 44 | 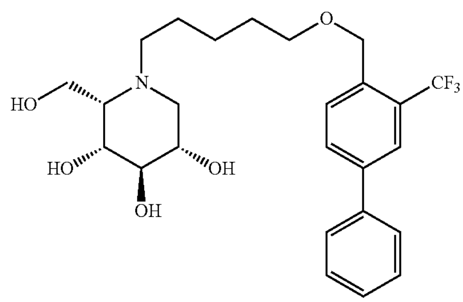 [SMILES: OC[C@H]1[C@@H](O)[C@H](O)[C@@H](O)CN1CCCCCOCc1ccc(-c2ccccc2)cc1C(F)(F)F] | 3 | 0.1 | 5000 |
| 45 | 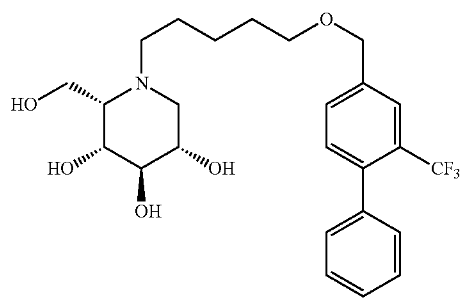 [SMILES: OC[C@H]1[C@@H](O)[C@H](O)[C@@H](O)CN1CCCCCOCc1ccc(-c2ccccc2)c(C(F)(F)F)c1] | 3 | 0.1 | 6000 |
| 46 | 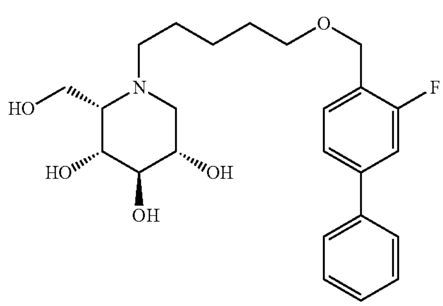 [SMILES: OC[C@H]1[C@@H](O)[C@H](O)[C@@H](O)CN1CCCCCOCc1ccc(-c2ccccc2)cc1F] | 5 | 0.4 | 8000 |
| 47 | 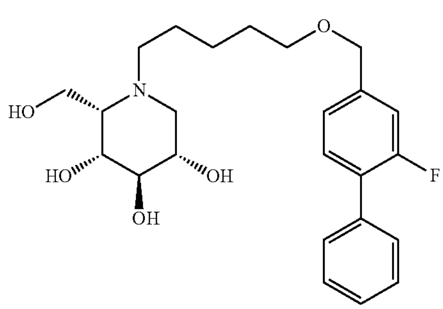 [SMILES: OC[C@H]1[C@@H](O)[C@H](O)[C@@H](O)CN1CCCCCOCc1ccc(-c2ccccc2)c(F)c1] | 2.5 | 0.6 | 6000 |

Example 5: Inhibitory Potency of a D-deoxygalactonojirimycin Derivative Towards GCS, GBA1 and GBA2

| compound number | structure | GCS [nM] | GBA2 [nM] | GBA1 [nM] |
|---|---|---|---|---|
| 48 | (structure) | 100 | 2 | 200000 |

Example 6: Further Representative Compounds of General Structure I, which can be Prepared Following Route A or Route B

| compound number | compound type | structure |
|---|---|---|
| 51 | L-ido deoxynojirimycin | (structure) |
| 52 | L-ido deoxynojirimycin | (structure) |
| 53 | L-ido deoxynojirimycin | (structure) |

-continued
| compound number | compound type | structure |
|---|---|---|
| 54 | L-ido deoxynojirimycin | 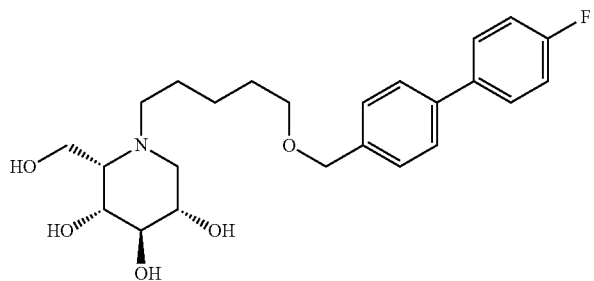 [SMILES: OC[C@H]1[C@@H](O)[C@H](O)[C@@H](O)CN1CCCCCOCc1ccc(-c2ccc(F)cc2)cc1] |
| 55 | L-ido deoxynojirimycin | 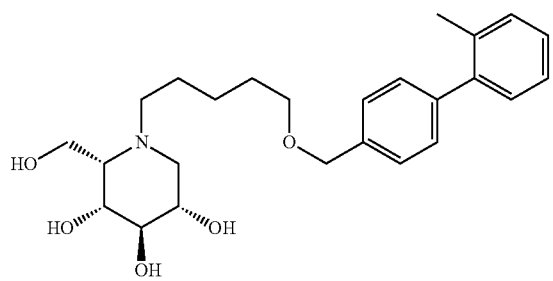 [SMILES: Cc1ccccc1-c1ccc(COCCCCCN2C[C@H](O)[C@@H](O)[C@H](O)[C@@H]2CO)cc1] |
| 56 | L-ido deoxynojirimycin | 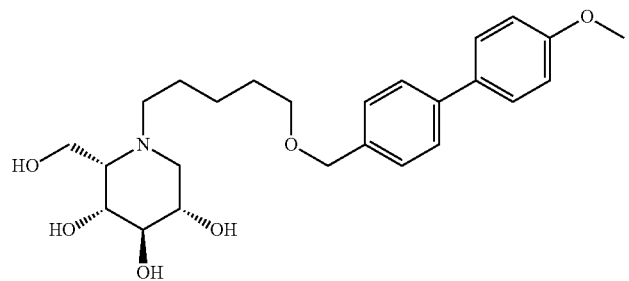 [SMILES: COc1ccc(-c2ccc(COCCCCCN3C[C@H](O)[C@@H](O)[C@H](O)[C@@H]3CO)cc2)cc1] |
| 57 | L-ido deoxynojirimycin | 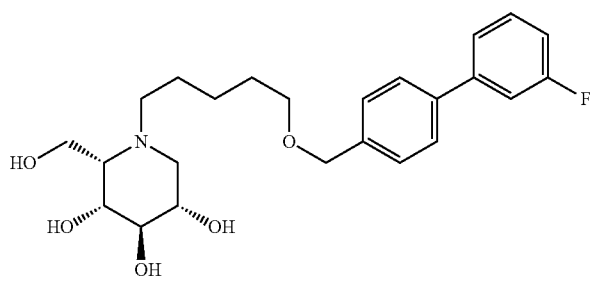 [SMILES: OC[C@H]1[C@@H](O)[C@H](O)[C@@H](O)CN1CCCCCOCc1ccc(-c2cccc(F)c2)cc1] |
| 58 | L-ido deoxynojirimycin | 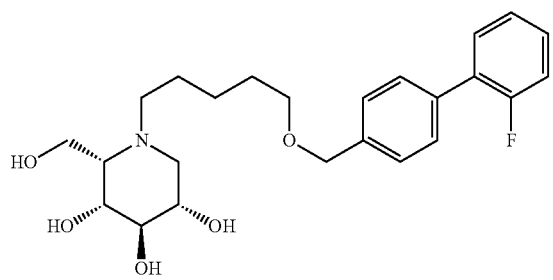 [SMILES: OC[C@H]1[C@@H](O)[C@H](O)[C@@H](O)CN1CCCCCOCc1ccc(-c2ccccc2F)cc1] |

-continued
| compound number | compound type | structure |
|---|---|---|
| 59 | L-ido deoxynojirimycin | 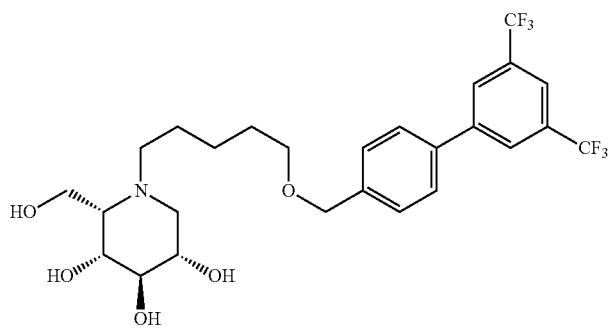 [SMILES: OC[C@H]1[C@@H](O)[C@H](O)[C@@H](O)CN1CCCCCOCc1ccc(-c2cc(C(F)(F)F)cc(C(F)(F)F)c2)cc1] |
| 60 | L-ido deoxynojirimycin | 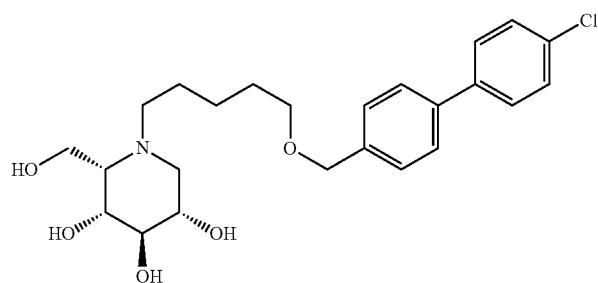 [SMILES: OC[C@H]1[C@@H](O)[C@H](O)[C@@H](O)CN1CCCCCOCc1ccc(-c2ccc(Cl)cc2)cc1] |
| 61 | L-ido deoxynojirimycin | 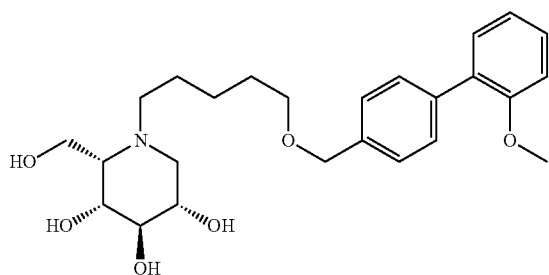 [SMILES: COc1ccccc1-c1ccc(COCCCCCN2C[C@H](O)[C@@H](O)[C@H](O)[C@@H]2CO)cc1] |
| 62 | L-ido deoxynojirimycin | 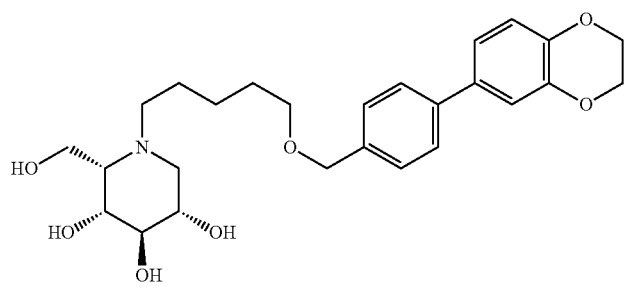 [SMILES: OC[C@H]1[C@@H](O)[C@H](O)[C@@H](O)CN1CCCCCOCc1ccc(-c2ccc3c(c2)OCCO3)cc1] |
| 63 | L-ido deoxynojirimycin | 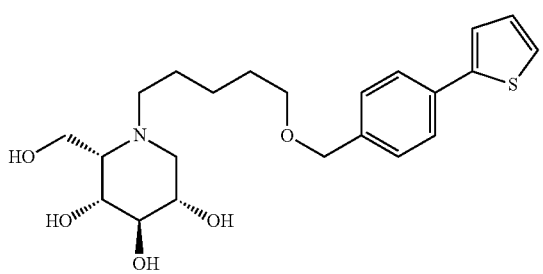 [SMILES: OC[C@H]1[C@@H](O)[C@H](O)[C@@H](O)CN1CCCCCOCc1ccc(-c2cccs2)cc1] |

| compound number | compound type | structure |
|---|---|---|
| 64 | L-ido deoxynojirimycin | 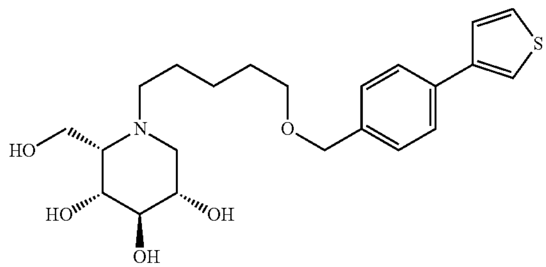 [SMILES: OC[C@H]1[C@@H](O)[C@H](O)[C@@H](O)CN1CCCCCOCc1ccc(-c2ccsc2)cc1] |
| 49 | D-gluco deoxynojirimycin | 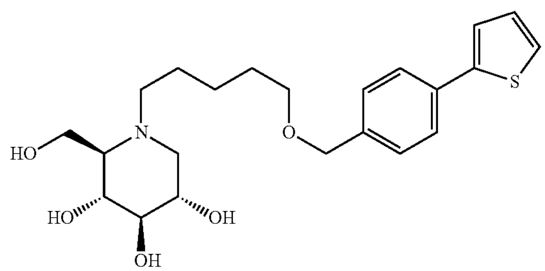 [SMILES: OC[C@@H]1[C@@H](O)[C@H](O)[C@@H](O)CN1CCCCCOCc1ccc(-c2cccs2)cc1] |
| 50 | D-gluco deoxynojirimycin | 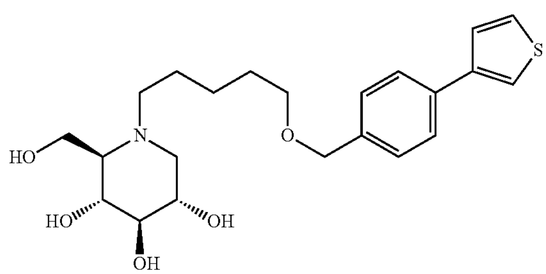 [SMILES: OC[C@@H]1[C@@H](O)[C@H](O)[C@@H](O)CN1CCCCCOCc1ccc(-c2ccsc2)cc1] |

The invention claimed is:

1. A method of inhibiting glucosylceramide synthase (GCS) in a subject having a disorder characterized by glycosphingolipid accumulation, comprising administering to the subject a GCS-inhibiting compound of structure I or Ia:

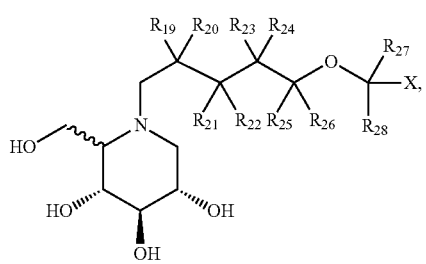

I

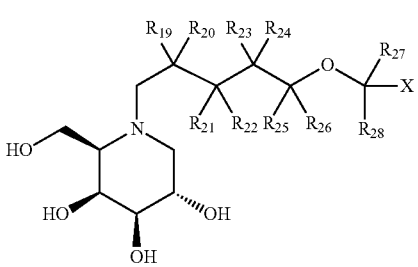

Ia wherein:
each of $R_{19}$-$R_{26}$ is independently selected from H, F, Me or Et;
$R_{27}$ and $R_{28}$ is independently selected from the group consisting of H, F, $CF_3$ and $C_1$-$C_8$ linear or branched alkyl;

X is

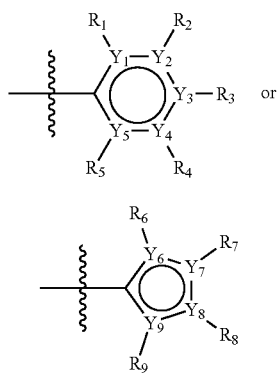

wherein
- $Y_1$-$Y_5$ are independently selected from the group of C and N-atoms provided that not more than two of $Y_1$-$Y_5$ are a N-atom, and provided that if one or two of $Y_1$-$Y_5$ is a N-atom, the R-group attached to that N-atom is void;
- $Y_6$-$Y_9$ are independently selected from the group of C-, S-, N- and O-atoms and comprise at least one of an S-, N- or O-atom, provided that $Y_6$-$Y_9$ comprises at most one S-atom, at most one N-atom and/or at most one O-atom, and provided that if one of $Y_6$-$Y_9$ is a S- or O-atom, the R-group attached to any S-, N- and/or O-atom is void, and provided that if none of $Y_6$-$Y_9$ is a S- or O-atom, the R-group attached to any N-atom is selected from the group consisting of H, $C_1$-$C_8$ linear or branched alkyl, IV and V, and provided that O and S-atoms are not concomitantly present;
- one of $R_1$-$R_9$ is

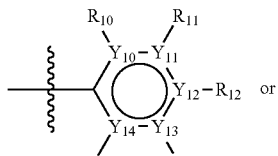

and the remaining of $R_1$-$R_9$ are independently selected from the group consisting of H, F, Cl, Br, I, CN, $CF_3$, $C_1$-$C_8$ linear or branched alkyl and $C_1$-$C_8$ linear or branched oxyalkyl;
wherein
- $Y_{10}$-$Y_{14}$ are independently selected from the group of C- and N-atoms provided that not more than two of $Y_{10}$-$Y_{14}$ are a N-atom, and provided that if one or two of $Y_{10}$-$Y_{14}$ is a N-atom, the R-group attached to that N-atom is void;
- $Y_{15}$-$Y_{18}$ are independently selected from the group of C-, S-, N- and O-atoms and $Y_{19}$ is selected from the group consisting of a C-atom and a N-atom, provided that $Y_{15}$-$Y_{19}$ comprises at most one S-atom, at most one N-atom and/or at most one O-atom, provided that if one of $Y_{15}$-$Y_{19}$ is a S- or O-atom, the group attached to any S-, N and/or O-atom is void, and provided that if none of $Y_{15}$-$Y_{19}$ is a S- or O-atom, the group attached to any N-atom is selected from the group consisting of H or $C_1$-$C_8$ linear or branched alkyl, and provided that O and S-atoms are not concomitantly present;
- $R_{10}$-$R_{18}$ are independently selected from the group consisting of H, F, Cl, Br, I, CN, $CF_3$, $C_1$-$C_8$ linear or branched alkyl or $C_1$-$C_8$ linear or branched oxyalkyl, and/or wherein two of $R_{10}$-$R_{18}$ form a linear or branched fused alkylene or alkylenedioxy ring on two adjacent atoms of $Y_{10}$-$Y_{18}$;

or a pharmaceutically acceptable salt thereof, in an amount effective to inhibit GCS in the subject.

2. The method according to claim 1, wherein X=

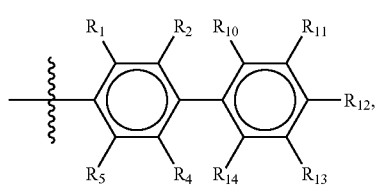

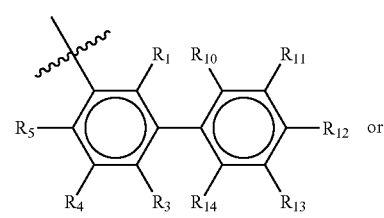

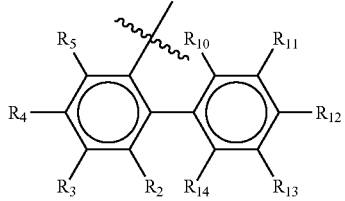

wherein each of the group consisting of $R_1$-$R_4$ are independently selected from the group consisting of H, F, Cl, Br, I, CN, $CF_3$, and $C_1$-$C_8$ linear or branched alkyl, and $R_{10}$-$R_{14}$ are independently selected from the group consisting of H, F, Cl, Br, I, CN, $CF_3$, and $C_1$-$C_8$ linear or branched alkyl and/or wherein two of the group consisting of $R_{10}$-$R_{14}$ form a linear or branched fused alkylene or alkylenedioxy ring on two adjacent atoms.

3. The method according to claim 1, wherein $R_{27}$ is H and $R_{28}$ is methyl.

4. The method according to claim 1, wherein the iminosugar moiety has the L-ido configuration IX:

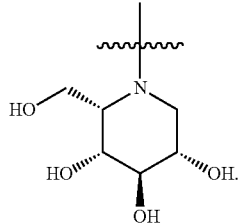
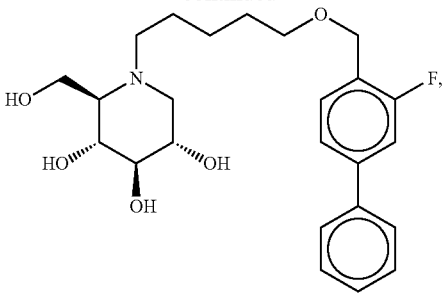
5. The method according to claim 1, wherein the iminosugar moiety has the D-gluco configuration XI:
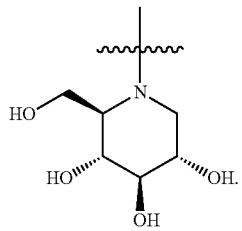
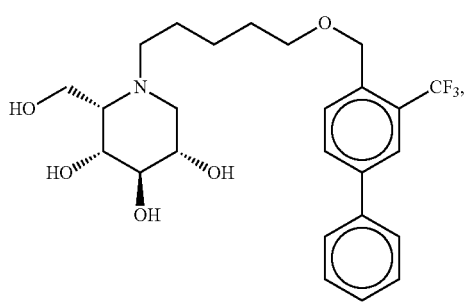
6. The method according to claim 1, wherein the compound is selected from the group consisting of
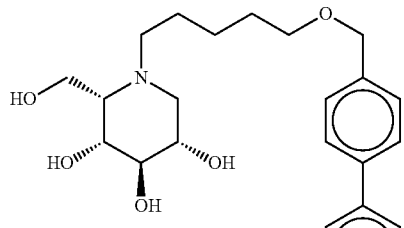
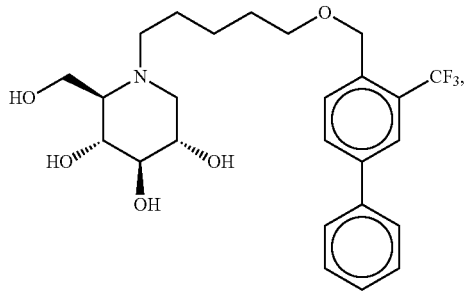
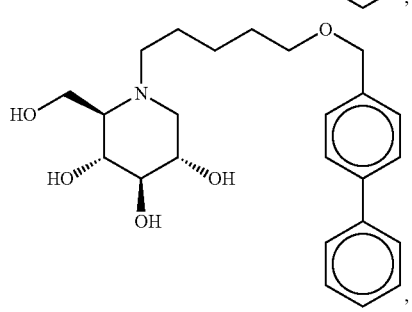
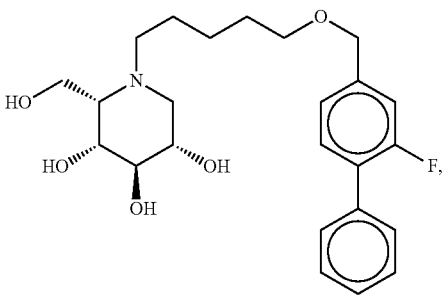
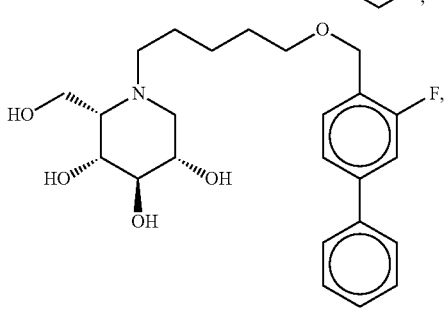
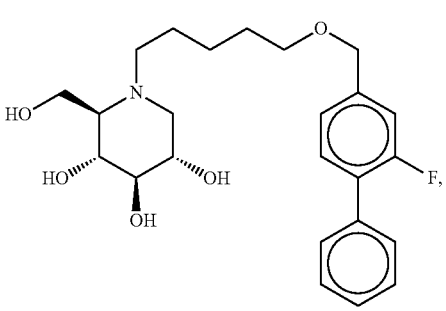

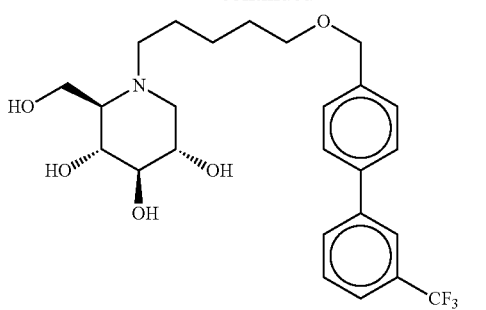

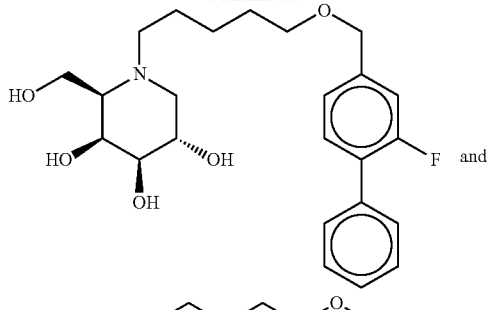

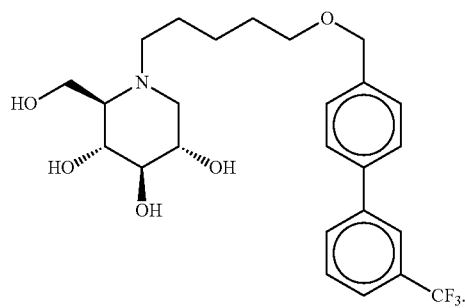

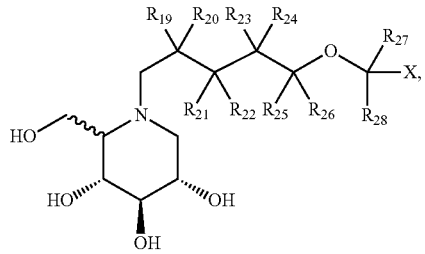

7. The method according to claim 1, wherein the compound is selected from the group consisting of

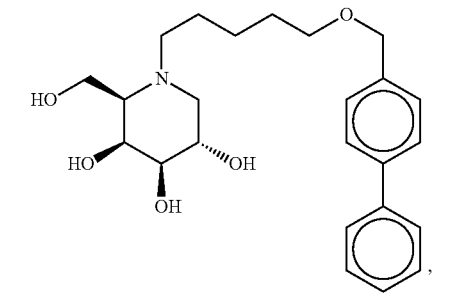

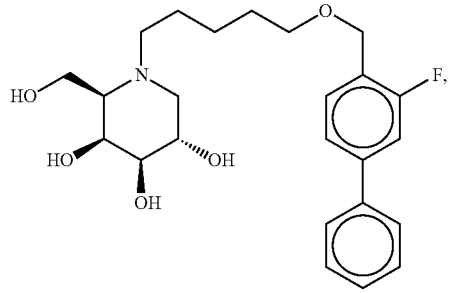

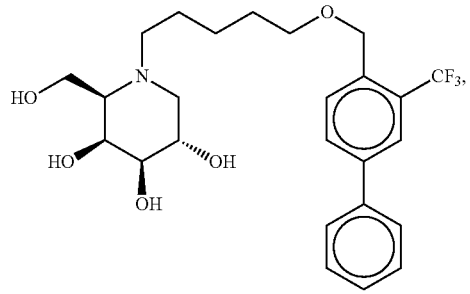

8. The method according to claim 1, comprising administering a pharmaceutical composition which comprises the compound in combination with a pharmaceutically acceptable excipient.

9. A method of decreasing the level of glycosphingolipids in a subject having a disorder characterized by glycosphingolipid accumulation, comprising

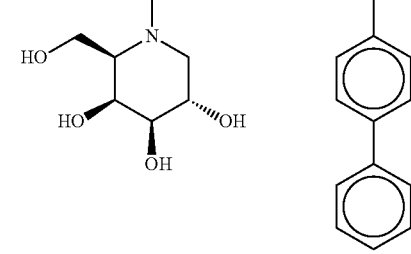

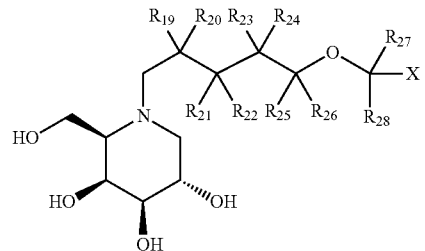

wherein:
each of $R_{19}$-$R_{26}$ is independently selected from H, F, Me or Et;
$R_{27}$ and $R_{28}$ is independently selected from the group consisting of H, F, $CF_3$ and $C_1$-$C_8$ linear or branched alkyl;

X is

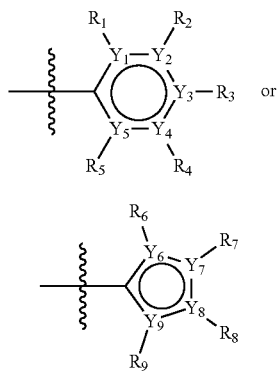

wherein
$Y_1$-$Y_5$ are independently selected from the group of C and N-atoms provided that not more than two of $Y_1$-$Y_5$ are a N-atom, and provided that if one or two of $Y_1$-$Y_5$ is a N-atom, the R-group attached to that N-atom is void;

$Y_6$-$Y_9$ are independently selected from the group of C-, S-, N- and O-atoms and comprise at least one of an S-, N- or O-atom, provided that $Y_6$-$Y_9$ comprises at most one S-atom, at most one N-atom and/or at most one O-atom, and provided that if one of $Y_6$-$Y_9$ is a S- or O-atom, the R-group attached to any S-, N- and/or O-atom is void, and provided that if none of $Y_6$-$Y_9$ is a S- or O-atom, the R-group attached to any N-atom is selected from the group consisting of H, $C_1$-$C_8$ linear or branched alkyl, IV and V, and provided that O and S-atoms are not concomitantly present;

one of $R_1$-$R_9$ is

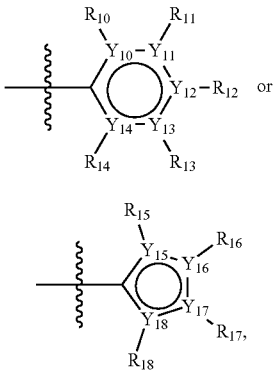

and the remaining of $R_1$-$R_9$ are independently selected from the group consisting of H, F, Cl, Br, I, CN, $CF_3$, $C_1$-$C_8$ linear or branched alkyl and $C_1$-$C_8$ linear or branched oxyalkyl;

wherein
$Y_{10}$-$Y_{14}$ are independently selected from the group of C- and N-atoms provided that not more than two of $Y_{10}$-$Y_{14}$ are a N-atom, and provided that if one or two of $Y_{10}$-$Y_{14}$ is a N-atom, the R-group attached to that N-atom is void;

$Y_{15}$-$Y_{18}$ are independently selected from the group of C-, S-, N- and O-atoms and $Y_{19}$ is selected from the group consisting of a C-atom and a N-atom, provided that $Y_{15}$-$Y_{19}$ comprises at most one S-atom, at most one N-atom and/or at most one O-atom, provided that if one of $Y_{15}$-$Y_{19}$ is a S- or O-atom, the group attached to any S-, N and/or O-atom is void, and provided that if none of $Y_{15}$-$Y_{19}$ is a S- or O-atom, the group attached to any N-atom is selected from the group consisting of H or $C_1$-$C_8$ linear or branched alkyl, and provided that O and S-atoms are not concomitantly present;

$R_{10}$-$R_{18}$ are independently selected from the group consisting of H, F, Cl, Br, I, CN, $CF_3$, $C_1$-$C_8$ linear or branched alkyl or $C_1$-$C_8$ linear or branched oxyalkyl, and/or wherein two of $R_{10}$-$R_{18}$ form a linear or branched fused alkylene or alkylenedioxy ring on two adjacent atoms of $Y_{10}$-$Y_{18}$;

or a pharmaceutically acceptable salt thereof, in an amount effective to decrease the level of glycosphingolipids in the subject.

10. The method of claim 9 which comprises decreasing the levels of glucosylceramide in the subject.

11. The method according to claim 9, wherein X=

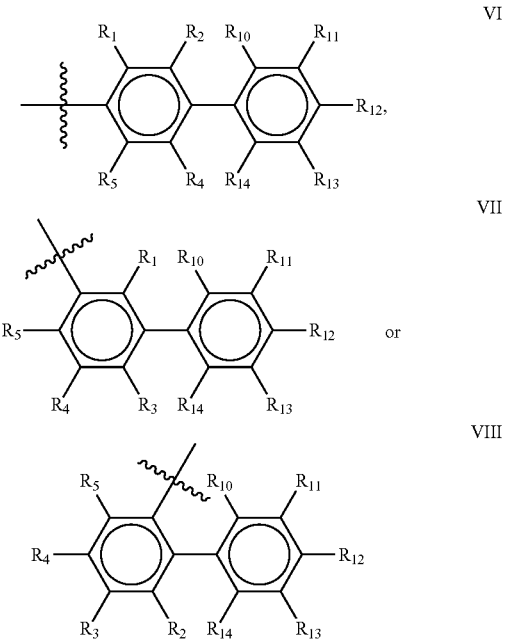

wherein each of the group consisting of $R_1$-$R_4$ are independently selected from the group consisting of H, F, Cl, Br, I, CN, $CF_3$, and $C_1$-$C_8$ linear or branched alkyl, and $R_{10}$-$R_{14}$ are independently selected from the group consisting of H, F, Cl, Br, I, CN, $CF_3$, and $C_1$-$C_8$ linear or branched alkyl and/or wherein two of the group consisting of $R_{10}$-$R_{14}$ form a linear or branched fused alkylene or alkylenedioxy ring on two adjacent atoms.

12. The method according to claim 9, wherein $R_{27}$ is H and $R_{28}$ is methyl.

13. The method according to claim 9, wherein the iminosugar moiety has the L-ido configuration IX:

IX
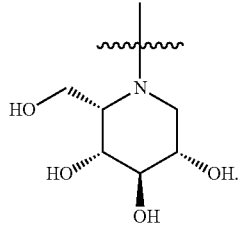
14. The method according to claim 9, wherein the iminosugar moiety has the D-gluco configuration XI:
XI
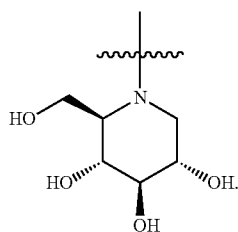
15. The method according to claim 9, wherein the compound is selected from the group consisting of
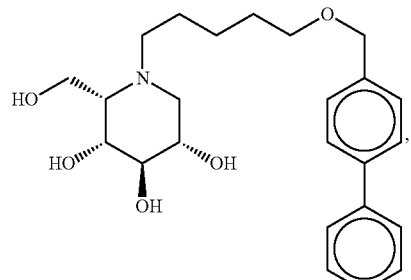
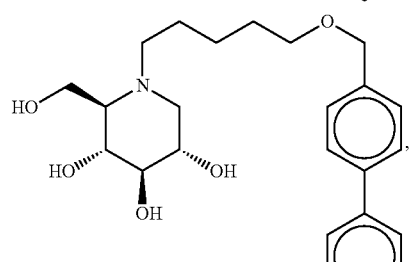
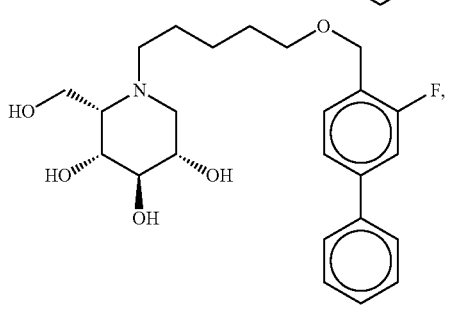
-continued
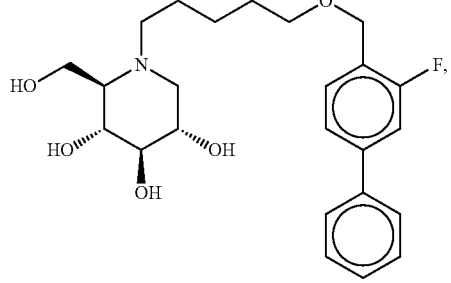
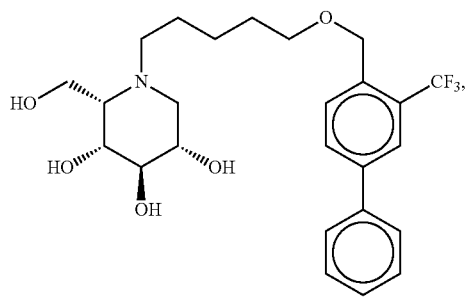
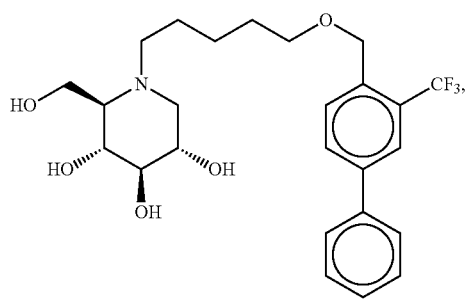
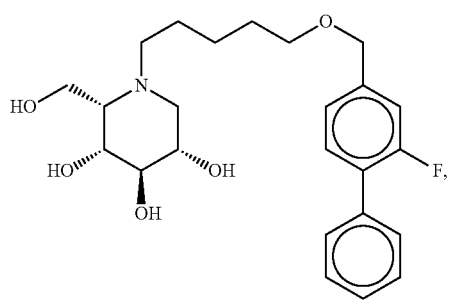
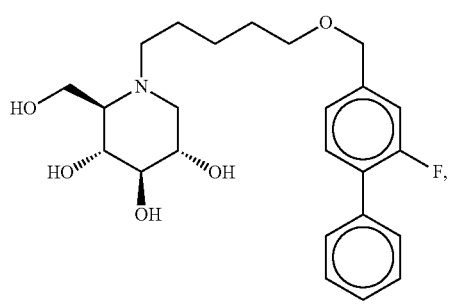

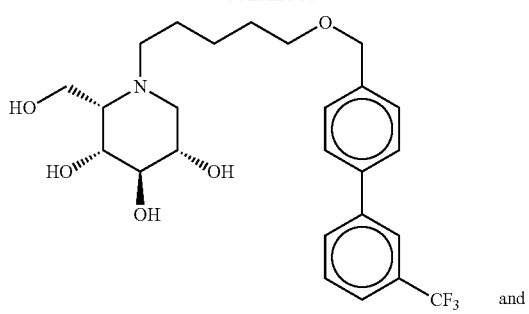

and

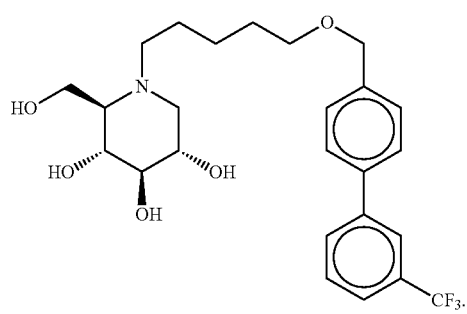

16. The method according to claim 9, wherein the compound is selected from the group consisting of

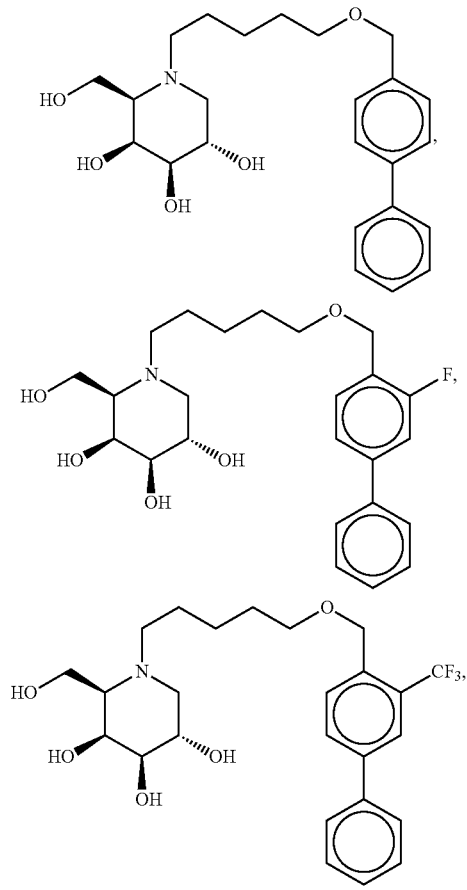

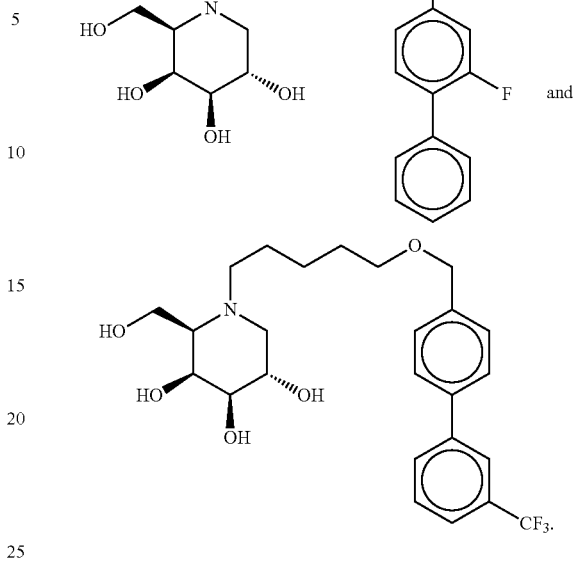

and

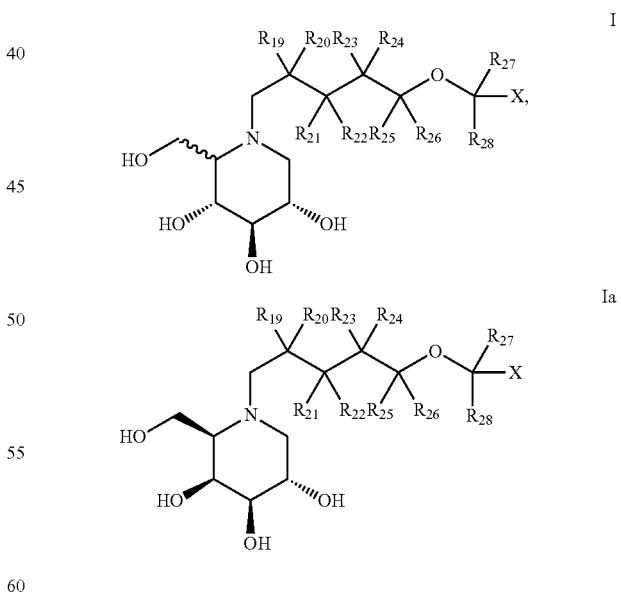

17. The method according to claim 9 comprising administering a pharmaceutical composition which comprises the compound in combination with a pharmaceutically acceptable excipient.

18. A method of inhibiting neutral glucosylceramidase (GBA2) in a subject having a disorder characterized by glycosphingolipid accumulation and over-activity of GBA2, comprising administering to the subject a GBA2-inhibiting compound of structure I or Ia:

wherein:
  each of $R_{19}$-$R_{26}$ is independently selected from H, F, Me or Et;
  $R_{27}$ and $R_{28}$ is independently selected from the group consisting of H, F, $CF_3$ and $C_1$-$C_8$ linear or branched alkyl;

X is

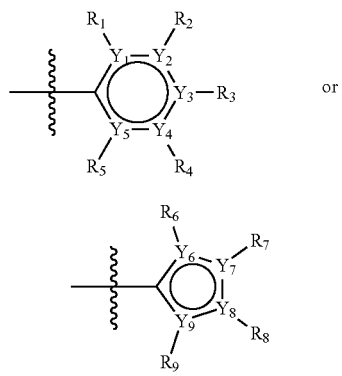

wherein
- $Y_1$-$Y_5$ are independently selected from the group of C and N-atoms provided that not more than two of $Y_1$-$Y_5$ are a N-atom, and provided that if one or two of $Y_1$-$Y_5$ is a N-atom, the R-group attached to that N-atom is void;
- $Y_6$-$Y_9$ are independently selected from the group of C-, S-, N- and O-atoms and comprise at least one of an S-, N- or O-atom, provided that $Y_6$-$Y_9$ comprises at most one S-atom, at most one N-atom and/or at most one O-atom, and provided that if one of $Y_6$-$Y_9$ is a S- or O-atom, the R-group attached to any S-, N- and/or O-atom is void, and provided that if none of $Y_6$-$Y_9$ is a S- or O-atom, the R-group attached to any N-atom is selected from the group consisting of H, $C_1$-$C_8$ linear or branched alkyl, IV and V, and provided that O and S-atoms are not concomitantly present;
- one of $R_1$-$R_9$ is

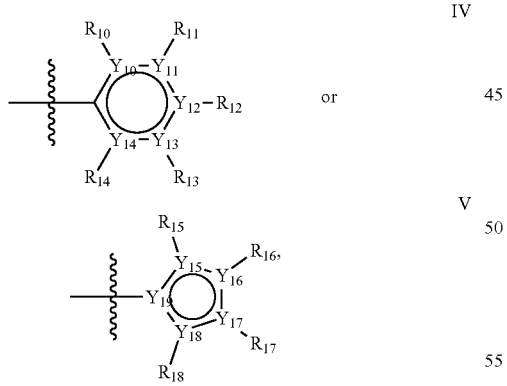

and the remaining of $R_1$-$R_9$ are independently selected from the group consisting of H, F, Cl, Br, I, CN, $CF_3$, $C_1$-$C_8$ linear or branched alkyl and $C_1$-$C_8$ linear or branched oxyalkyl;
wherein
- $Y_{10}$-$Y_{14}$ are independently selected from the group of C- and N-atoms provided that not more than two of $Y_{10}$-$Y_{14}$ are a N-atom, and provided that if one or two of $Y_{10}$-$Y_{14}$ is a N-atom, the R-group attached to that N-atom is void;
- $Y_{15}$-$Y_{18}$ are independently selected from the group of C-, S-, N- and O-atoms and $Y_{19}$ is selected from the group consisting of a C-atom and a N-atom, provided that $Y_{15}$-$Y_{19}$ comprises at most one S-atom, at most one N-atom and/or at most one O-atom, provided that if one of $Y_{15}$-$Y_{19}$ is a S- or O-atom, the group attached to any S-, N and/or O-atom is void, and provided that if none of $Y_{15}$-$Y_{19}$ is a S- or O-atom, the group attached to any N-atom is selected from the group consisting of H or $C_1$-$C_8$ linear or branched alkyl, and provided that O and S-atoms are not concomitantly present;
- $R_{10}$-$R_{18}$ are independently selected from the group consisting of H, F, Cl, Br, I, CN, $CF_3$, $C_1$-$C_8$ linear or branched alkyl or $C_1$-$C_8$ linear or branched oxyalkyl, and/or wherein two of $R_{10}$-$R_{18}$ form a linear or branched fused alkylene or alkylenedioxy ring on two adjacent atoms of $Y_{10}$-$Y_{18}$;

or a pharmaceutically acceptable salt thereof, in an amount effective to inhibit GBA2 in the subject.

19. The method according to claim 18, wherein X=

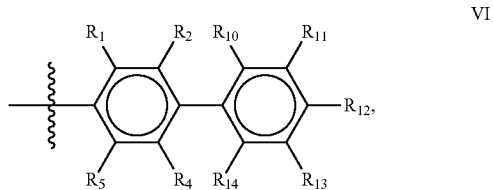

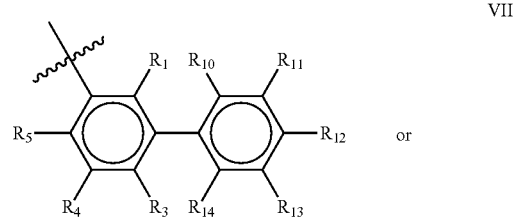

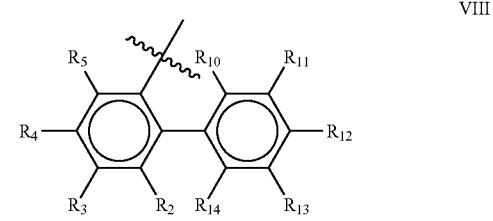

wherein each of the group consisting of $R_1$-$R_4$ are independently selected from the group consisting of H, F, Cl, Br, I, CN, $CF_3$, and $C_1$-$C_8$ linear or branched alkyl, and $R_{10}$-$R_{14}$ are independently selected from the group consisting of H, F, Cl, Br, I, CN, $CF_3$, and $C_1$-$C_8$ linear or branched alkyl and/or wherein two of the group consisting of $R_{10}$-$R_{14}$ form a linear or branched fused alkylene or alkylenedioxy ring on two adjacent atoms.

20. The method according to claim 18, wherein $R_{27}$ is H and $R_{28}$ is methyl.

21. The method according to claim 18, wherein the iminosugar moiety has the L-ido configuration IX:

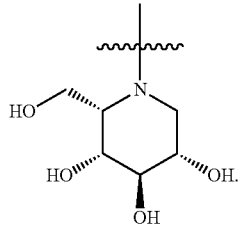
IX
22. The method according to claim 18, wherein the iminosugar moiety has the D-gluco configuration XI:
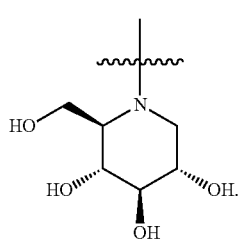
XI
23. The method according to claim 18, wherein the compound is selected from the group consisting of
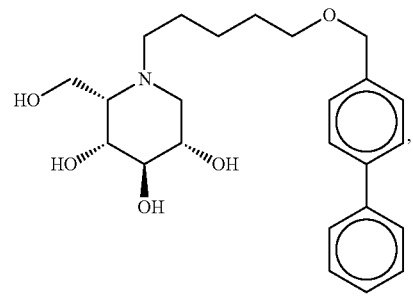
,
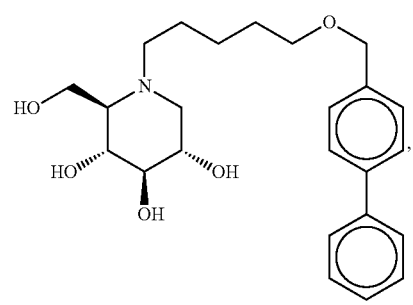
,
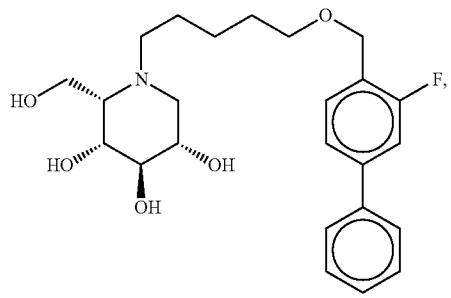
,
-continued
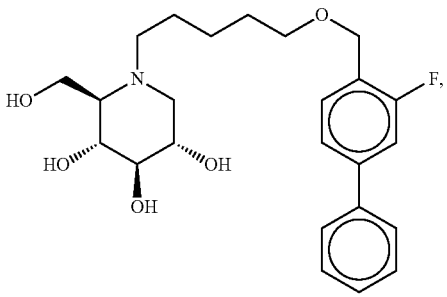
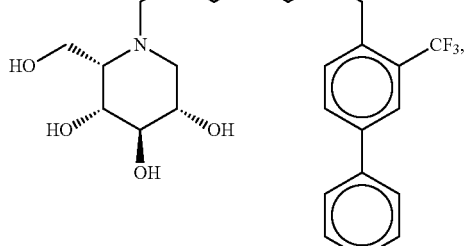
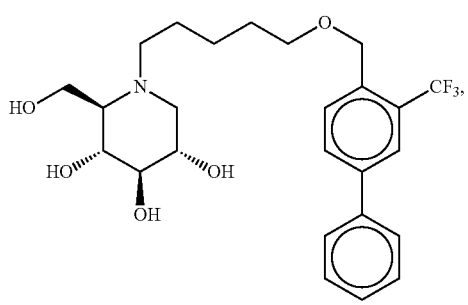
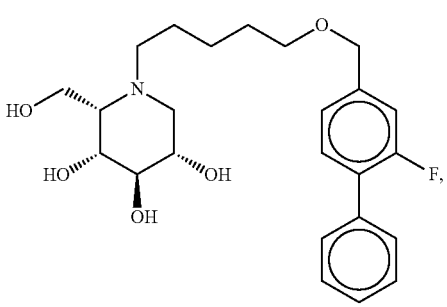
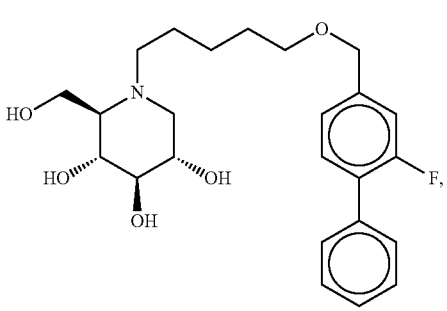

127
-continued
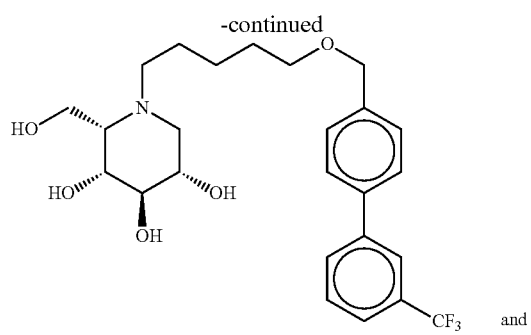
and
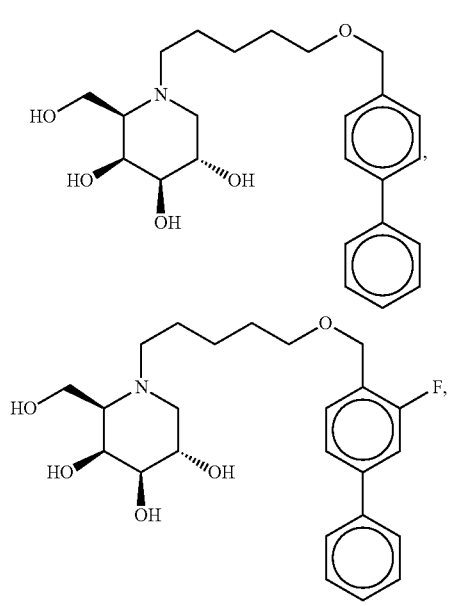
24. The method according to claim 18, wherein the compound is selected from the group consisting of
128
-continued
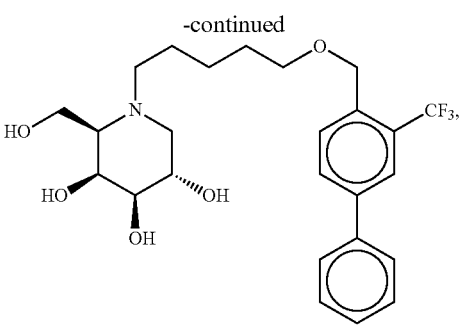
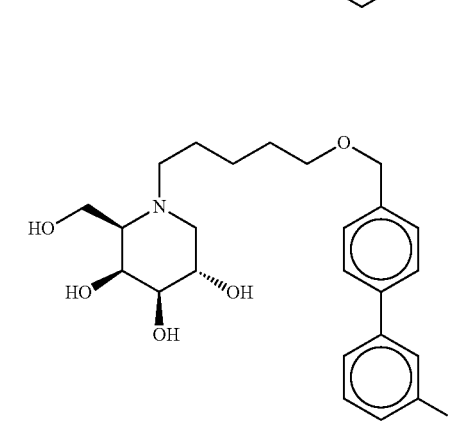
25. The method according to claim 18, comprising administering a pharmaceutical composition which comprises the compound in combination with a pharmaceutically acceptable excipient.
* * * * *